(12) United States Patent
Tilton et al.

(10) Patent No.: US 6,878,861 B2
(45) Date of Patent: Apr. 12, 2005

(54) ACYL COENZYME A THIOESTERASES

(75) Inventors: Gregory B. Tilton, Pullman, WA (US); Jay M. Shockey, Pullman, WA (US); John A. Browse, Pullman, WA (US)

(73) Assignee: Washington State University Research Foundation, Pullman, WA (US)

(*) Notice: Subject to any disclaimer, the term of this patent is extended or adjusted under 35 U.S.C. 154(b) by 0 days.

(21) Appl. No.: 09/906,408

(22) Filed: Jul. 16, 2001

(65) Prior Publication Data
US 2003/0028915 A1 Feb. 6, 2003

Related U.S. Application Data

(60) Provisional application No. 60/220,028, filed on Jul. 21, 2000.

(51) Int. Cl.[7] .................... C12N 15/82; A01H 5/00
(52) U.S. Cl. .................... 800/298; 800/281; 435/6; 435/7.4; 536/23.2
(58) Field of Search .................. 800/298, 281; 435/6, 7.4, 69.1, 419, 471, 468, 252.3; 536/23.2, 23.6

(56) References Cited

U.S. PATENT DOCUMENTS

| | | | |
|---|---|---|---|
| 4,657,760 A | 4/1987 | Kung et al. .................... 424/85 |
| 4,683,195 A | 7/1987 | Mullis et al. .................... 435/6 |
| 4,683,202 A | 7/1987 | Mullis .......................... 435/91 |
| 4,940,838 A | 7/1990 | Schilperoort et al. ......... 800/205 |
| 4,965,188 A | 10/1990 | Mullis et al. .................... 435/6 |
| 5,096,815 A | 3/1992 | Ladner et al. ............. 435/69.1 |
| 5,173,410 A | 12/1992 | Ahlquist ...................... 435/91 |
| 5,198,346 A | 3/1993 | Ladner et al. ............. 435/69.1 |
| 5,223,409 A | 6/1993 | Ladner et al. ............. 435/69.7 |
| 5,324,637 A | 6/1994 | Thompson et al. ......... 435/68.1 |
| 5,352,605 A | 10/1994 | Fraley et al. ............. 435/240.4 |
| 5,500,360 A | 3/1996 | Ahlquist et al. ......... 435/172.3 |
| 5,501,967 A | 3/1996 | Offringa et al. ......... 435/172.3 |
| 5,584,807 A | 12/1996 | McCabe ...................... 604/71 |
| 5,589,616 A | 12/1996 | Hoffman .................... 800/205 |
| 5,608,153 A | 3/1997 | Ueyanagi ...................... 73/1 |
| 5,733,731 A | 3/1998 | Schatz et al. .................. 435/6 |
| 5,767,363 A | 6/1998 | De Silva et al. ............ 800/205 |
| 5,811,238 A | 9/1998 | Stemmer et al. .............. 435/6 |
| 5,824,877 A | 10/1998 | Hinchee et al. ............. 800/205 |
| 5,830,721 A | 11/1998 | Stemmer et al. ......... 435/172.1 |
| 5,837,458 A | 11/1998 | Minshull et al. .............. 435/6 |
| 5,846,795 A | 12/1998 | Ahlquist et al. ......... 435/172.3 |
| 5,866,785 A | 2/1999 | Donson et al. ............. 800/205 |
| 5,891,840 A | 4/1999 | Cady et al. .................... 514/2 |
| 5,965,794 A | 10/1999 | Turpen ....................... 800/288 |
| 5,977,438 A | 11/1999 | Turpen et al. .............. 800/288 |
| 5,981,839 A | 11/1999 | Knauf et al. ............... 800/287 |
| 6,051,757 A | 4/2000 | Barton et al. .............. 800/294 |
| 6,063,947 A | 5/2000 | DeBonte et al. ............ 554/223 |

FOREIGN PATENT DOCUMENTS

| | | |
|---|---|---|
| EP | 1 033 405 A | 9/2000 |
| WO | WO 90/02909 | 3/1990 |
| WO | WO 92/09690 | 6/1992 |
| WO | WO 95/14098 | 5/1995 |
| WO | WO 98/06831 | 2/1998 |
| WO | WO 02/04648 | 1/2002 |

OTHER PUBLICATIONS

Chen et al, Accesson AI999643, Sep. 8, 1999.*
De Luca V, AgBiotech News and Information vol. 5, No. 6:225N–229N, 1993.*
Broun et al, Science 282: 131–133, Nov. 13, 1998.*
Van de Loo et al, PNAS USA, vol. 22:6743–6747, Jul. 1995.*
Anderson and Young (1985) Quantitative Filter Hybridisation, in *Nucleic Acid Hybridisation: a practical approach* (eds: B.D. Harnes, S.J. Higgins; Oxford).
Barbas et al. (1992) PNAS 89:4457–4461.
Ben–Bassat et al. (1987) J. Bacteriol. 169:751–757.
Bidney et al., (1992) Plant Molec. Biol. 18:301–313.
Caldwell and Joyce (1992) PCR Methods Appl. 2:28–33.
Cannon et al. (1990) Plant Mol. Biol. 15:39–47.
Caruthers et al. (1980) Nuc. Acids Res. Symp. Ser., 7:215–233.
Ch'ng et al., (1989) Proc. Natl. Acad. Sci. USA 86:10006–10010.
Chow and Kempe (1981) Nuc. Acids Res., 9:2807–2817.
Clackson et al., (1991) Nature, 352:624–628.
Coombs (1994) *Dictionary of Biotechnoogy* (Stockton Press; New York, NY). This reference is a book and is not being provided at this time. If the Examiner requests this reference it will be provided.
Crameri et al. (1996) Nat. Biotech., 14:315–19.
Crameri et al. (1997) Nat. Biotech., 15:436–38.
Crea and Horn (1980) Nuc. Acids Res., 9:2331.
Creighton (1983) *Proteins. Structures, and Molecular Principles* W H Freeman and Co.; New York, N.Y.).
Cwirla et al. (1990) PNAS 87:6378–6382.
Davis et al. (1986) *Basic Methods in Molecular Biology* (Elsevier, New York, N.Y.).
Devlin et al. (1990) Science 249:404–406, 1990.
Dieffenbach and Gs Dvekler (1995) *PCR Primer, a Laboratory Manual* (Cold Spring Harbor Press; Plainview, NY). This reference is a book and is not being provided at this time. If the Examiner requests this reference it will be provided.

(Continued)

Primary Examiner—Elizabeth F. McElwain
(74) Attorney, Agent, or Firm—Medlen & Carroll, LLP

(57) ABSTRACT

The present invention provides compositions and methods related to acyl-coenzyme A thioesterases. In particular, the present invention is related to plant acyl-coenzyme A thioesterases. The present invention encompasses both native and recombinant wild-type forms of the enzymes, as well as mutant and variant forms, some of which possess altered characteristics relative to the wild-type enzyme. The present invention also relates to methods of using acyl-CoA thioesterases, including altered expression in transgenic plants and expression in prokaryotes and cell culture systems.

9 Claims, 10 Drawing Sheets

OTHER PUBLICATIONS

Eckert and Kunkel (1991) PCR Methods Appl., 1:17–24.
Garbarino and Belknap (1994) Plant Mol. Biol. 24:119–127.
Griffths et al. (1993) EMBO J., 12:725–734.
Gueguen et al. (2000) J Biol Chem. 275(7): 5016–25.
Hooykas–Van Slogteren et al., (1984) Nature 311:763–764.
Ike et al. (1983) Nucleic Acid Res. 11:477.
Itakura et al. (1981) *Recombinant DNA, Proc 3rd Cleveland Sympos. Macromol.* (Walton, ed.; Elsevier; Amsterdam) pp. 273–289.
Itakura et al. (1984) Annu. Rev. Biochem. 53:323.
Klee et al., (1987) Ann Rev. Plant Phys. 38:467–486.
Leung et al. (1989) Technique, 1:11–15.
Maniatis et al., (1987) Science 236:1237.
Marks et al. (1992) J. Biol. Chem., 267:16007–16010, 1992.
Matteucci and Caruthers (1980) Tetrahedron Lett., 21:719.
Miller et al. (1990) PNAS 84:2718–1722.
Moore and Arnold (1996) Nat. Biotech.:14, 458–67.
Mullis, KB et al., (1986) *Cold Spring Harbor Symposia, vol. LI,* pp. 263–273.
Napoli et al. (1990) Plant Cell 2:279–289.
Narang (1983) Tetrahedron 39:39.
Nielsen et al., (1993) Anticancer Drug Des., 8:53–63.
Poupon et al. (1999) J. Biol. Chem., 274:19188–19194.
Roberge et al., (1995) Science 269:202–204.
Roberts et al. (1992) PNAS 89:2429–2433.
Sambrook, et al. (1989) *Molecular Cloning: A Laboratory Manual, 2nd ed.* (Cold Spring Harbor Laboratory Press; New York, NY) pp. 16.7–16.8.
Sambrook, supra, at 16.6–16.7.
Scott et al. (1980) Science 249:386–390, 1980.
Shahla et al. (1987) Plant Molec. Biol. 8:291–298.
Sheehy et al. (1988) Proc. Natl. Acad Sci USA 85:8805–8809.
Smith et al. (1990) Mol. Gen. Genetics 224:477–481.
Smith (1994) Nature, 370:324–25.
Stemmer (1994) Nature, 370:398–91.
Stemmer (1994) Proc. Natl. Acad. Sci. USA, 91, 10747–51.
Stryer ed. (1981) *Biochemistry, 2nd ed* (WH Freeman and Co.) pp. 17–21.
van der Krol et al. (1988) Biotechniques 6:958–976.
van der Krol et al. (1990) Plant Cell 2:291–299.
Voss, et al. (1986) Trends Biochem. Sci., 11:287.
Zeng (1998) Biotechniques, 25:206–208.
Zhang et al. (1997) Proc. Natl. Acad. Sci. USA, 94:4504–09.
Zhao and Arnold (1997) Nuc. Acids. Res., 25:1307–08.
Block, MA et al. (1983) J Biol Chem 258(21): 13281–13286.
Hellyer, A et al. (1992) Plant Mol Biol 20(5): 763–780.
Larson, JD and Kolattukudy, PE (1985) Arch Biochem Biophys 237(1):27–37.
Murphy, DJ et al. (1984) Eur J Biochem 142(1): 43–48.
Tilton, G et al. (2000) Biochem Soc Trans 28(6): 946–947.
Jones, JM et al. (1999) J Biol Chem 274(14): 9216–9223.
Chang C–C et al. (1999) J Cell Sci 112(10): 1579–1590.
Ohlrogge, JB et al. (1978) Arch Biochem Biophys 189(2):382–391.
Safford, R et al., (1993) Transgenic Research 2(4): 191–198.
"Sequence of BAC Tin6 from *Arabidopsis thalina* chromosome 1, complete sequence." Database EMBL [Online] Dabase accession No. AC009273 (Aug. 13, 1999).
"884 AT–NHC *Arabidopsis thaliana* cDNA clone B119XP, mRNA sequence." Database EMBL [Online] Database accession No. T04836 (1993–08030).
"*Arabidopsis thaliana* DNA chromosome 4, contig fragment No. 2" Database EMBL [Online] Database accession No. AL161472 (Mar. 16, 2000).
"F6N23.3 Protein (Putative Acetyl COA Thioesterase)." Database Swissprot [Online] Database accession No. 065260 (Aug. 1, 1998).
"F6N23.2 Protein (Predicted Protein with Unknown Function)." Database Swissprot [Online] Database accession No. 065260 (Aug. 1, 1998).
"s190f03.yl Gm0c1037 Glycine max cDNA clone Genome Systems Clone Ed: Gm–c1037–1302 5' similar to TR:065261 065261 F6N23.3 Protein. ; mRNA sequence." Database EMBL [Online] Database accession No. AW781751 (May 14, 2000).
"7011501781 *A. thaliana,* Ohio State clone set *Arabidopsis thaliana* cDNA clone 7011501781, mRNA sequence." Database EMBL [Online] Database accession No. A1995096 (Sep. 9, 1999).
"701556839 *A. thaliana,* Columbia Col–0, rosette–3 *Arabidospsi thaliana* cDNA clone 701556839, mRNA sequence." Database EMBL [Online] Database accession No. AU999643 (Sep. 9, 1999).

* cited by examiner

FIGURE 1

```
   1  ATGAACACTG AATCAGTTGT CGAGTTCCTT GGGAATGTGA CCTTGTTGCA
  51  GCGGTTACCT AGTTCCTCTC TGAAGAGAAT CTCCGAAGTC GTTGTCTTCA
 101  AAGGTTATGA CAGAGGTGAT TATGTGGTTC GTGAAAATCA AAATGTGGAT
 151  GGAGTTTATT TTCTCTTGCA AGGACAGGCT CAGGTTCTGA GATCAGCCGG
 201  AGAGGAAAAC TATCAAGAGT CCCTTTGAA ACGATATGAT TTCTTCGGCC
 251  ATGGTATTTT CGGGGATGTT TACTCAGCAG ATGTTGTTGC TGTGACAGAG
 301  CTTACCTGCT TGCTGTTGAT GTCTGATCAT CGTGCTTTAC TTGAAATAAA
 351  GTCAGTCTCG GATTCAGATA AGGAACGCTG TCTTGTGGAA GACATACTAT
 401  ATCTAGAACC ATTAGATTTG AATGTATACC GGGGGTTCAC CCCACCTAAT
 451  GCTCCAACCT ATGGAAAGGT TTATGGAGGG CAATTAGTTG GACAGGCACT
 501  TGCCGCAGCA TCAAAAACTG TTGAAACTAT GAAGATAGTC CATAATTTTC
 551  ATTGCTATTT CCTTCTTGTT GGAGATATAA ATATTCCCAT CATATATGAT
 601  GTTAACCGCT TACGTGACGG CAACAACTTT GCCACCAGAA GTGTAGATGC
 651  TAGACAGAAA GGAAAAACTA TATTCACCTT GTTCGCGTCA TTTCAGAAAA
 701  AGCAACAAGG TTTTATTCAC CAGGAGTCGA CCATGCCTCA TACACCAGCT
 751  CCTGAAACGC TTCTACCAAG GGAGGAGATG CTTAACGGC TTGTTACTGA
 801  GCCTCTGCTA CCTAGGGATT ACCGAAACCA AGTTGCAACT GAAATTAGTG
 851  TTCCATTCCC TATAGATATT CGATTTGTG AGCCAAATCG TTCCACTAAA
 901  CAGAATAAGT CTCCTCCAAG ACTAAAATAT TGGTTTAGAG CAAAGGGAAA
 951  ACTTTCTGAT GATGATCAAG CTTTGCACAG ATGTGTGGTT GCATTTGCTT
1001  CCGATTTGAT ATTCGCCACT ATCAGTTTAA ACCCTCACCG GAGAGAGGGC
1051  ATGAGTGTAG CTGCTCTTAG CCTGGACCAC TCGATGTGGT TCCACCGACC
1101  TGTAAGAGCA GATGATTGGT TGTTGTTTGT GATAGTGAGT CCAACTGCGA
1151  CCGAAAGCCG CGGTTTTGCA ACTGGCAAAA TGTTCAACAG AAAGGGAGAG
1201  CTGGTGGTAT CATTGACGCA AGAAGCTGTG TTAAGAGAAG CTGTGACTAT
1251  TAAGCCATCC TTCGGGGCCA AGCTATGA
```

FIGURE 2

```
   1 ATGAACACCG AGTCAGTTGT CGAGTTCCTT GGAAACGTCC CTTTACTCCA
  51 GAAATTACCG AGCTCTTCTC TGAAGAAAAT TGCTCAAGTT GTTGTGCCGA
 101 AACGTTACGG GAAAGGGGAT TATGTGGTTC GTGAAGATCA AACTTGGGAT
 151 GGATGTTATT TTATTTTGCA AGGAGAGGCT CAGGTTTCCG GACCAGACGA
 201 AGAAGATAAC CGTTCCGAAT TCCTCTTGAA ACAGTATGAT TACTTCGGCG
 251 TTGGTTTATC TGGGAACGTT CATTCAGCAG ACATTGTTGC TATGTCCCAG
 301 CTTACGTGTT TGGTGTTGCC GCGTGATCAC TGTCATTTGC TTGAGACTAA
 351 TTCCATCTGG CAATCGGATA CGTCACTTGA CAAATGCTCT TTAGTGGAAC
 401 GCATTTTGCA ACTCGACCCT TTAGAATTGA ATATCTTCAG GGGGATCACA
 451 CTACCTGATG CTCCTATATT TGGAAAGGTT TTTGGAGGAC AATTTGTCGG
 501 ACAGGCTCTT GCTGCGGCGT CAAAAACTGT TGATTTTCTC AAGGTCGTCC
 551 ACAGTTTACA CTCCTATTTT CTTCTCGTTG AGATATTGA CATCCCCATT
 601 ATTTATCAAG TTCACCGCAT ACGTGATGGG AACAACTTTG CCACCCGAAG
 651 AGTTGATGCA GTACAGAAAG GAAATATCAT ATTCATCTTG CTGGCATCAT
 701 TTCAGAAAGA ACAACAAGGA TTTGAGCACC AGGAGTCAAC CATGCCCTCT
 751 GTACCAGATC CTGATACGCT TCTATCACTG GAGGAGTTGC GTGAAAGCCG
 801 TATAACTGAT CCTCATTTAC CGAGGAGTTA TCGGAACAAA GTTGCAACTA
 851 GAAACTTTGT TCCATGGCCT ATAGAGATTC GATTTGTGA GCCCAGCAAT
 901 TCAACAAATC AGACAAAGTC TCCTCCGAGA TTGAACTATT GGTTTAGAGC
 951 AAAGGGAAGG CTTTCTGATG ATCAAGCTTT GCACCGATGT GTCGTTGCAT
1001 TTGCCTCGGA TTTAATATTT TGTGGTGTTG GTTTGAACCC TCACCGGAGA
1051 AAAGGGGTGA ATCCGCCGC ACTTAGCCTG GACCATGCGA TGTGGTTTCA
1101 CCGACCTCTA AGAGCCGACG AGTGGTTGCT CTATGTGATT GTGAGTCCAA
1151 CTGCGCATGA GACCCGTGGT TTTGTGACTG GTCAAATGTT CAACAGGAAA
1201 GGAGAGCTGG TTGTATCATT AACGCAAGAG GCCCTATTAA GAGAGGCTAG
1251 ACCTCCAAAA CCCTCCGGCA CGTCGAAGCT CTGA
```

FIGURE 3

```
   1  ATGAATTCCC CAAGACCCAT CTCCGTCGTC TCCACCTTCG CTTCACCATC
  51  CTCCACCTCT GACCCAACCC GAAAACCCTT AAGCTTATGG CCAGGTATGT
 101  ACCATTCACC TGTCACCACC GCTCTTTGGG AAGCCAGATC CAAAATCTTC
 151  GAATCTCTTC TCGATCCTCC TAAAGACGCT CCACCACAGA GCCAGCTTCT
 201  CACCAGAACT CCTTCTCATA GCCGTACCAC CATTTCTAC CCTTTCTCCA
 251  CTGATTTCAT TCTCAGAGAG CAATACAGAG ATCCTTGGAA CGAGGTCCGT
 301  ATCGGATCT TGCTCGAAGA TCTCGATGCT TTAGCCGGCA CTATCTCCGT
 351  CAAGCATTGT TCTGATGATG ATAGTACAAC GAGGCCACTC TTGCTTGTTA
 401  CAGCTTCTGT TCATAAGATT GTCTTAAAGA AGCCGATTTG TGTCGACATT
 451  GATCTCAAGA TTGTTGCTTC TGTCATTTGG GTTGGTCGTT CATCTATCGA
 501  GATTCAACTC GAAGTTATGC AATCCGAATT GAAAGATGTC AAGGCTTCTT
 551  CAGATTCTGT TGCTTTAACT GCAAATTTCA TTTTGTGGC GCGTGATTCT
 601  AAGACTGGTA AAGCTGCTCC TATCAACCGT CTTTCTCCTG AAACCGAGGT
 651  TGAGAAACTT CTCTTTGAGG AAGCTGAAGC TAGGAATAAC TTAAGGAAGA
 701  AGAAGAGAGG AGGTGACAGA AGGGAATTTG ATCACGGGGA GTGTAAGAAG
 751  CTTGAGGCTT GGTTGGCTGA AGGAAGGATT TTCTCTGACA TGCCAGCTCT
 801  TGCTGACAGA AACAGCATTC TTCTTAAAGA CACTCGTCTT GAGAATTCGC
 851  TGATATGCCA ACCGCAGCAG AGGAACATCC ATGGTAGGAT CTTTGGAGGG
 901  TTTTTAATGC ATAGAGCATT TGAGTTGGCT TTCTCTACTG CTTATACGTT
 951  TGCGGGTCTA GTGCCTTACT TCTTAGAAGT TGATCACGTC GATTTCCTAA
1001  GACCGGTGGA CGTCGGGGAT TTCTTACGTT TCAAATCCTG TGTTCTTTAC
1051  ACTCAACTGG ATAAACAGGA TTGTCCGCTC ATCAATATCG AAGTTGTTGC
1101  TCATGTTACA AGTCCAGAGA TTCGCTCCAG TGAGGTTTCA AATACATTCT
1151  ACTTCAAGTT CACTGTAAGG CCAGAGGCAA AGGCCAGAAA CAATGGGTTT
1201  AAACTTCGAA ATGTAGTTCC TGCCACAGAG GAAGAAGCTC GTCATATCCT
1251  CGAGCGCATG GATGCAGAAG CTTTGAAGTC AAGCAAACAA CAATGTGTAG
1301  GCACAATTCT TCAGTAA
```

FIGURE 4

```
   1  ATGAGATCTT CAGCGGGAAA GCTTCTCTCC CATTCTCTAC GGAGAAACCG
  51  CGGGAAACTT GGTGATGGAT TTTGGATTCC GGCTACGAGG TCTCAGAAGA
 101  TGTGGAATTC GACGGTACCG TCAGATGAAA ATCCTGATCA AAATTCGATC
 151  GATGCAGGAT CTTCAATGCG GAAACCAATT AGCTTATGGC CTGGAATGTA
 201  TCATTCTCCG GTGACTAATG CGCTTTGGGA AGCTCGTCGT AATATGTTCG
 251  AAATTCCTAC CGGAGACGAC GCTTCTCAGT CAAAATTGAC GGCTAAATCT
 301  CCGTCTCGAA GCCGAACGTC AATTCTCTAT AAGTTTTCTT CTGATTTTGT
 351  TCTTCGAGAA CAATATAGGA ATCCTTGGAA TGAGATTCGT ACTGGTAAAT
 401  TGGTTGAAGA TCTTGACGCT CTTGCTGGAA CCATCTCCTT CAAGCATTGT
 451  GGTGGTGACA GCAGTGCGAG ATCGATGATT TTGGTGACTG CTTCAGTGGA
 501  TAGGATTATC ATGAAAAGAC CTATTCGTGT AGATACTGAC CTTAGTATAG
 551  TTGGTGCTGT TACATGGGTT GGTAGATCAT CCATGGAGAT GCAATTACAA
 601  GTACTCCAAA TTCAAGATAC CAACAACTCC TCTGAGTCGG TTGCCCTTGA
 651  AGCAAACTTT ACATTCGTGG CTCGGGATGC TCAGACAGGC AAGTCAGCTC
 701  CAATTAACCA AGTCGTGCCA GAAACTGAGC ATGAAAAATT TCTGTGGAAA
 751  GAGGCAGAAG AGAGGAACAA ACTACGAAAA CAAAAGAGAG CACAGGGTAA
 801  AGAAGAGCAT GAGAAGTTGA AGGACTTAGA GAGGCTAAAT GAGTTATTAG
 851  CAGAAGGACG AGTATTCCTG GACATGCCAG CTCTTGCAGA TCGGAACAGC
 901  ATCCTAATTA AGGATACTTC CCATGAAAAC TCATTGATCT GCCAGCCACA
 951  GCAACGAAAT ATTCATGGCA GAATTTTTGG AGGCTTCTTG ATGCGCAAAG
1001  CTTTTGAGTT GGCTTTCTCC AATGCTTACA CCTTCGCTGG GGTTTCACCA
1051  CGTTTTCTCG AAGTTGATCG CGTCGATTTT ATCAAACCAG TGGATGTTGG
1101  AAATTTCCTT CGTTTCAAGT CACGCGTATT GTACACAGAA GCAACCAGTT
1151  CAGCTGAACC GCTGATAAAC ATCGAGGTTG TAGCTCATGT TACAAGTCCA
1201  GAGCTCAGAT CCAGCGAAGT CTCCAACAGG TTTTACTTCA CCTTCAGTGT
1251  GAGACCTGAG GCCATGAAAG ATGGATTGAA AATAAGAAAT GTGGTTCCAG
1301  CAACAGAAGA AGAAGCTAGA AGAGTGATCG AGCGCATGGA CGCAGAGAGA
1351  CCCATCTCAT TGCCTTGA
```

```
  1  MNTESVVEFL GNVTLLQRLP SSSLKRISEV VVFKGYDRGD YVVRENQNVD
 51  GVYFLLQGQA QVLRSAGEEN YQEFPLKRYD FFGHGIFGDV YSADVVAVTE
101  LTCLLLMSDH RALLEIKSVS DSDKERCLVE DILYLEPLDL NVYRGFTPPN
151  APTYGKVYGG QLVGQALAAA SKTVETMKIV HNFHCYFLLV GDINIPIIYD
201  VNRLRDGNNF ATRSVDARQK GKTIFTLFAS FQKKQQGFIH QESTMPHTPA
251  PETLLPREEM LERLVTEPLL PRDYRNQVAT EISVPFPIDI RFCEPNRSTK
301  QNKSPPRLKY WFRAKGKLSD DDQALHRCVV AFASDLIFAT ISLNPHRREG
351  MSVAALSLDH SMWFHRPVRA DDWLLFVIVS PTATESRGFA TGKMFNRKGE
401  LVVSLTQEAV LREAVTIKPS FGAKL
```

B

```
  1  MNTESVVEFL GNVPLLQKLP SSSLKKIAQV VVPKRYGKGD YVVREDQTWD
 51  GCYFILQGEA QVSGPDEEDN RSEFLLKQYD YFGVGLSGNV HSADIVAMSQ
101  LTCLVLPRDH CHLLETNSIW QSDTSLDKCS LVERILQLDP LELNIFRGIT
151  LPDAPIFGKV FGGQFVGQAL AAASKTVDFL KVVHSLHSYF LLVGDIDIPI
201  IYQVHRIRDG NNFATRRVDA VQKGNIIFIL LASFQKEQQG FEHQESTMPS
251  VPDPDTLLSL EELRESRITD PHLPRSYRNK VATRNFVPWP IEIRFCEPSN
301  STNQTKSPPR LNYWFRAKGR LSDDQALHRC VVAFASDLIF CGVGLNPHRR
351  KGVKSAALSL DHAMWFHRPL RADEWLLYVI VSPTAHETRG FVTGQMFNRK
401  GELVVSLTQE ALLREARPPK PSGTSKL
```

```
  1  MNSPRPISVV STFASPSSTS DPTRKPLSLW PGMYHSPVTT ALWEARSKIF
 51  ESLLDPPKDA PPQSQLLTRT PSHSRTTIFY PFSTDFILRE QYRDPWNEVR
101  IGILLEDLDA LAGTISVKHC SDDDSTTRPL LLVTASVHKI VLKKPICVDI
151  DLKIVASVIW VGRSSIEIQL EVMQSELKDV KASSDSVALT ANFIFVARDS
201  KTGKAAPINR LSPETEVEKL LFEEAEARNN LRKKKRGGDR REFDHGECKK
251  LEAWLAEGRI FSDMPALADR NSILLKDTRL ENSLICQPQQ RNIHGRIFGG
301  FLMHRAFELA FSTAYTFAGL VPYFLEVDHV DFLRPVDVGD FLRFKSCVLY
351  TQLDKQDCPL INIEVVAHVT SPEIRSSEVS NTFYFKFTVR PEAKARNNGF
401  KLRNVVPATE EEARHILERM DAEALKSSKQ QCVGTILQ
```

B

```
  1  MRSSAGKLLS HSLRRNRGKL GDGFWIPATR SQKMWNSTVP SDENPDQNSI
 51  DAGSSMRKPI SLWPGMYHSP VTNALWEARR NMFEIPTGDD ASQSKLTAKS
101  PSRSRTSILY KFSSDFVLRE QYRNPWNEIR TGKLVEDLDA LAGTISFKHC
151  GGDSSARSMI LVTASVDRII MKRPIRVDTD LSIVGAVTWV GRSSMEMQLQ
201  VLQIQDTNNS SESVALEANF TFVARDAQTG KSAPINQVVP ETEHEKFLWK
251  EAEERNKLRK QKRAQGKEEH EKLKDLERLN ELLAEGRVFL DMPALADRNS
301  ILIKDTSHEN SLICQPQQRN IHGRIFGGFL MRKAFELAFS NAYTFAGVSP
351  RFLEVDRVDF IKPVDVGNFL RFKSRVLYTE ATSSAEPLIN IEVVAHVTSP
401  ELRSSEVSNR FYFTFSVRPE AMKDGLKIRN VVPATEEEAR RVIERMDAER
451  PISLP
```

ACYL COENZYME A THIOESTERASES

This application claims priority from provisional application U.S. Ser. No. 60/220,028, filed on Jul. 21, 2000.

FIELD OF THE INVENTION

The present invention provides compositions and methods related to acyl-coenzyme A thioesterases. In particular, the present invention is related to plant acyl coenzyme A thioesterases.

BACKGROUND OF THE INVENTION

Acyl coenzyme A (acyl-CoA) thioesterases (ACHs) are enzymes that cleave thioester bonds between CoA and a fatty acyl group. These enzymes, also referred to as acyl-CoA hydrolases, have been identified in all animal and bacterial organisms studied to date, including *E. coli* and humans. Eukaryotic cells contain various isoforms of these enzymes, which are located in various organelles, most notably mitochondria, peroxisomes, and the endoplasmic reticulum, as well as the cytosol. Although their true physiological role is not currently understood, studies conducted in yeast have indicated that deletion of the peroxisomal form leads to decreased growth when oleic acid is provided as the carbon source. Other studies in rats indicate that other isoforms exhibit increased expression under conditions where fatty acids are being broken down (e.g., during fasting periods). Overall, the experimental evidence gathered to date indicates that these enzymes have a role in lipid oxidation and may be involved in regulation of the CoA pool within cells. Thus, there remains a need for purified forms of these enzymes, as well as nucleic and polypeptide sequences, such that the function of these enzymes can be further elucidated and methods developed for regulation of fatty acid metabolism.

SUMMARY OF THE INVENTION

The present invention provides compositions and methods related to acyl-coenzyme A thioesterases. In particular, the present invention is related to plant acyl coenzyme A thioesterases.

The present invention provides compositions comprising an isolated nucleic acid sequence selected from the group consisting of SEQ ID NO:1, SEQ ID NO:2, SEQ ID NO:3, and SEQ ID NO:4. The present invention also provides an isolated nucleic acid sequence encoding a protein comprising an amino acid sequence selected from the group consisting of SEQ ID NO:5, SEQ ID NO:6, SEQ ID NO:7, and SEQ ID NO:8. The present invention also provides an isolated nucleic acid sequence that hybridizes under conditions of medium to high stringency to a nucleic acid sequence selected from the group consisting of SEQ ID NO:1, SEQ ID NO:2, SEQ ID NO:3, and SEQ ID NO:4.

In some embodiments of the present invention, the nucleic acid sequences described above are operably linked to a heterologous promoter. In further embodiments, the sequences described above are contained within a vector. In still further embodiments, the vectors are within a host cell. The present invention is not limited to any particular host cell. Indeed, a variety of host cells are contemplated, including, but not limited to, prokaryotic cells, eukaryotic cells, plant tissue cells, and cells in planta.

The present invention further provides methods for altering the phenotype of a plant comprising providing a vector comprising a nucleic acid sequence as described above, and plant tissue, and transfecting the plant with the vector under conditions such that the protein is expressed.

The present invention also provides methods for assaying acyl-CoA thioesterase activity comprising providing a nucleic acid sequence as described above, expressing the nucleic acid sequence under conditions such that a protein is produced, and assaying the activity of the protein.

The present invention also provides methods to alter the phenotype of a plant, comprising providing a vector comprising an antisense sequence corresponding to a nucleic acid sequence as described above, and a plant tissue, and transfecting the plant tissue with the vector under conditions such that the antisense sequence is expressed and wherein the activity of an acyl-CoA thioesterase is down-regulated as compared to wild-type plants.

The present invention further provides nucleic acid sequences having one or more plant acyl-CoA thioesterase motifs, wherein the motif is a cGMP binding domain. In some embodiments, the motif is selected from the group consisting of SEQ ID NO:11 and SEQ ID NO:12.

The present invention also provides a host cell comprising a nucleic acid selected from the group consisting of SEQ ID NO:1, SEQ ID NO:2, SEQ ID NO:3, SEQ ID NO:4, and sequences that hybridize under conditions of medium to high stringency to a nucleic acid sequence selected from the group consisting of SEQ ID NO:1, SEQ ID NO:2, SEQ ID NO:3, and SEQ ID NO:4, wherein the nucleic acid sequence is operably linked to an exogenous promoter. In other embodiments, the present inventions provides a transgenic plant comprising a nucleic acid sequence selected from the group consisting of SEQ ID NO:1, SEQ ID NO:2, SEQ ID NO:3, and SEQ ID NO:4 and sequences that hybridize under conditions of medium to high stringency to a nucleic acid sequence selected from the group consisting of SEQ ID NO:1, SEQ ID NO:2, SEQ ID NO:3, and SEQ ID NO:4, wherein the nucleic acid sequence is operably linked to an exogenous promoter. In additional embodiments, the present invention provides oil and seeds from such a transgenic plant.

The present invention also provides a nucleic acid encoding a plant acyl-CoA thioesterase, wherein the plant acyl-CoA thioesterase competes for binding to an acyl-CoA substrate with a protein encoded by a nucleic acid sequence selected from the group consisting of a nucleic acid sequence selected from the group consisting of SEQ ID NO:1, SEQ ID NO:2, SEQ ID NO:3, and SEQ ID NO:4.

The present invention also provides a composition comprising a first nucleic acid that inhibits the binding of at least a portion of a second nucleic acid to its complementary sequence, where the second nucleic acid sequence is selected from the group consisting of SEQ ID NO:1, SEQ ID NO:2, SEQ ID NO:3, and SEQ ID NO:4.

The present invention also provides a method for producing variants of acyl-CoA thioesterases comprising providing a nucleic acid sequence selected from the group consisting of SEQ ID NO:1, SEQ ID NO:2, SEQ ID NO:3, and SEQ ID NO: 4, mutagenizing the nucleic acid sequence, and screening the variant encoded by the mutagenized nucleic acid sequence for activity.

In other embodiments, the present invention provides compositions comprising purified acyl-CoA thioesterases comprising amino acid sequences SEQ ID NOs: 5–8, and portions thereof.

DESCRIPTION OF THE FIGURES

FIG. 1 shows the ACH1 cDNA sequence (SEQ ID NO:1).

FIG. 2 shows the ACH2 cDNA sequence (SEQ ID NO:2).

FIG. 3 shows the ACH4 cDNA sequence (SEQ ID NO:3).

FIG. 4 shows the ACH5 cDNA sequence (SEQ ID NO:4).

FIG. 5, Panel A shows the ACH1 peptide sequence (SEQ ID NO:5). The putative cGMP binding domain (SEQ ID NO:11) indicated by underlining.

FIG. 5, Panel B shows the ACH2 peptide sequence (SEQ ID NO:6). The putative cGMP binding domain (SEQ ID NO:12) indicated by underlining.

FIG. 6, Panel A shows the ACH4 peptide sequence (SEQ ID NO:7).

FIG. 6, Panel B shows the ACH5 peptide sequence (SEQ ID NO:8).

DESCRIPTION OF THE INVENTION

Figure 7:
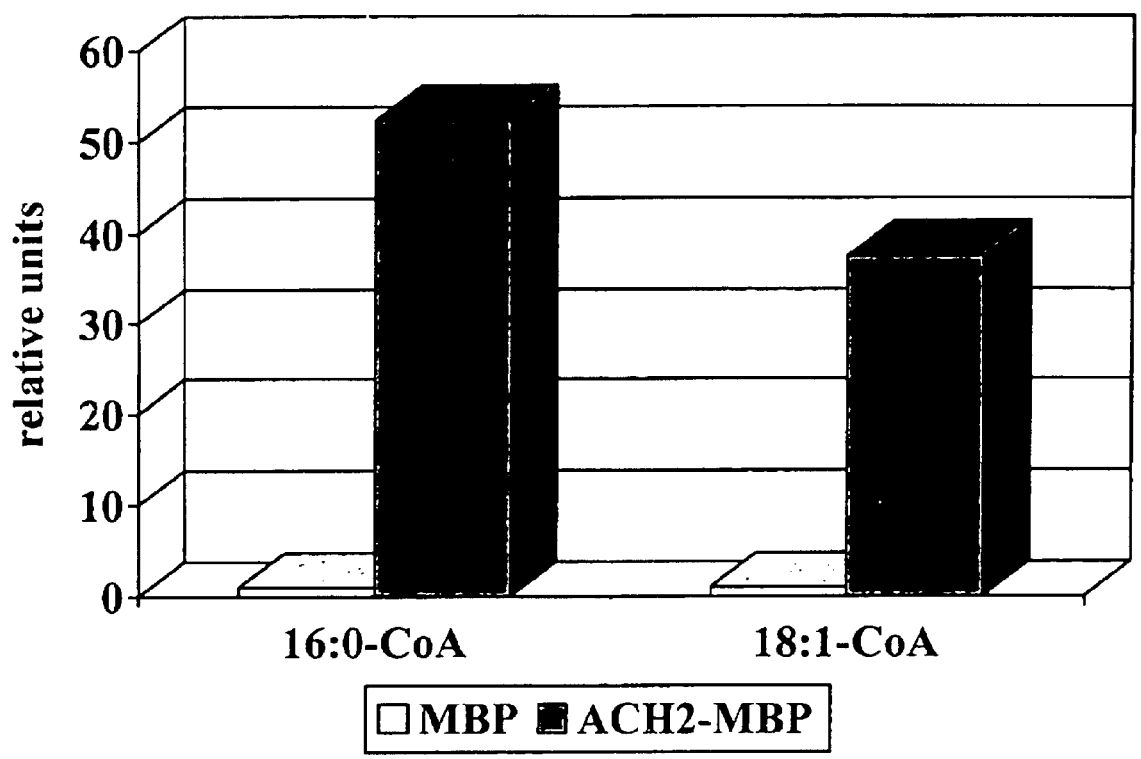
FIG. 7 shows a histogram showing the activity of ACH2-MBP and MBP.

The present invention provides compositions and methods related to acyl-coenzyme A thioesterases. In particular, the present invention is related to plant acyl-coenzyme A thioesterases. The present invention encompasses both native and recombinant wild-type forms of the enzymes, as well as mutant and variant forms, some of which possess altered characteristics relative to the wild-type enzyme. The present invention also relates to methods of using acyl-CoA thioesterases, including altered expression in transgenic plants and expression in prokaryotes and cell culture systems. After the "Definitions," the following Description of the Invention is divided into: I. Acyl-CoA Thioesterases; and II. Uses of Acyl-CoA Thioesterase Nucleic Acids and Polypeptides.

Definitions

To facilitate understanding of the invention, a number of terms are defined below.

The term "plant" as used herein refers to a plurality of plant cells which are largely differentiated into a structure that is present at any stage of a plant's development. Such structures include, but are not limited to, a fruit, shoot, stem, leaf, flower petal, etc. The term "plant tissue" includes differentiated and undifferentiated tissues of plants including, but not limited to, roots, shoots, leaves, pollen, seeds, tumor tissue and various types of cells in culture (e.g., single cells, protoplasts, embryos, callus, protocorm-like bodies, etc.). Plant tissue may be in planta, in organ culture, tissue culture, or cell culture.

"Oil-producing species" herein refers to plant species which produce and store triacylglycerol in specific organs, primarily in seeds. Such species include soybean (*Glycine max*), rapeseed and canola (including *Brassica napus* and *B. campestris*), sunflower (*Helianthus annus*), cotton (*Gossypium hirsutum*), corn (*Zea mays*), cocoa (*Theobroma cacao*), safflower (*Carthamus tinctorius*), oil palm (*Elaeis guineensis*), coconut palm (*Cocos nucifera*), flax (*Linum usitatissimum*), castor (*Ricinus communis*) and peanut (*Arachis hypogaea*). The group also includes non-agronomic species which are useful in developing appropriate expression vectors such as tobacco, rapid cycling Brassica species, and *Arabidopsis thaliana*, and wild species which may be a source of unique fatty acids.

As used herein, the terms "acyl-CoA thioesterase" and "acyl-CoA hydrolase" (ACH) are used interchangeably to refer to an enzymatic activity that catalyzes the hydrolysis of acyl-CoA, resulting in the formation of free fatty acid and reduced coenzyme A (CoA). The terms "plant acyl-CoA thioesterase" or "plant acyl-CoA hydrolase" refer to an acyl-CoA thioesterase derived from a plant. These terms encompass both acyl-CoA thioesterases that are identical to wild type plant acyl-CoA thioesterases and those that are derived from wild type plant acyl-CoA thioesterases (e.g., variants of plant acyl-CoA thioesterases or chimeric genes constructed with portions of plant acyl-CoA thioesterase coding regions).

As used herein, the term "acyl-CoA synthetase (ACS)" refers to an enzymatic activity that catalyzes the formation of an acyl-CoA from a free fatty acid and coenzyme A (CoA). As used herein, the term "plant acyl-CoA synthetase" refers to an acyl-CoA synthetase derived from a plant.

The term "gene" as used herein, refers to a DNA sequence that comprises control and coding sequences necessary for the production of a polypeptide or protein precursor. The polypeptide can be encoded by a full length coding sequence or by any portion of the coding sequence, as long as the desired protein activity is retained.

"Nucleoside," as used herein, refers to a compound consisting of a purine [guanine (G) or adenine (A)] or pyrimidine [thymine (T), uridine (U), or cytidine (C)] base covalently linked to a pentose, whereas "nucleotide" refers to a nucleoside phosphorylated at one of its pentose hydroxyl groups.

A "nucleic acid," as used herein, is a covalently linked sequence of nucleotides in which the 3' position of the pentose of one nucleotide is joined by a phosphodiester group to the 5' position of the pentose of the next, and in which the nucleotide residues (bases) are linked in specific sequence (i.e., a linear order of nucleotides). A "polynucleotide," as used herein, is a nucleic acid containing a sequence that is greater than about 100 nucleotides in length. An "oligonucleotide," as used herein, is a short polynucleotide or a portion of a polynucleotide. An oligonucleotide typically contains a sequence of about two to about one hundred bases. The word "oligo" is sometimes used in place of the word "oligonucleotide".

Nucleic acid molecules are said to have a "5'-terminus" (5' end) and a "3'-terminus" (3' end) because nucleic acid phosphodiester linkages occur to the 5' carbon and 3' carbon of the pentose ring of the substituent mononucleotides. The end of a nucleic acid at which a new linkage would be to a 5' carbon is its 5' terminal nucleotide. The end of a nucleic acid at which a new linkage would be to a 3' carbon is its 3' terminal nucleotide. A terminal nucleotide, as used herein, is the nucleotide at the end position of the 3'- or 5'-terminus.

DNA molecules are said to have "5' ends" and "3' ends" because mononucleotides are reacted to make oligonucleotides in a manner such that the 5' phosphate of one mononucleotide pentose ring is attached to the 3' oxygen of its neighbor in one direction via a phosphodiester linkage. Therefore, an end of an oligonucleotides referred to as the "5' end" if its 5' phosphate is not linked to the 3' oxygen of a mononucleotide pentose ring and as the "3' end" if its 3' oxygen is not linked to a 5' phosphate of a subsequent mononucleotide pentose ring.

"Nucleic acid sequence" as used herein refers to an oligonucleotide, nucleotide or polynucleotide, and fragments or portions thereof, and to DNA or RNA of genomic or synthetic origin which may be single- or double-stranded, and represent the sense or antisense strand. Similarly, "amino acid sequence" as used herein refers to a peptide or protein sequence. "Peptide nucleic acid" as used herein refers to an oligomeric molecule in which nucleosides are joined by peptide, rather than phosphodiester, linkages. These small molecules, also designated anti-gene agents, stop transcript elongation by binding to their complementary (template) strand of nucleic acid (Nielsen et al. (1993) Anticancer Drug Des., 8:53–63).

A "deletion" is defined as a change in either nucleotide or amino acid sequence in which one or more nucleotides or amino acid residues, respectively, are absent.

An "insertion" or "addition" is that change in a nucleotide or amino acid sequence which has resulted in the addition of one or more nucleotides or amino acid residues, respectively, as compared to, naturally occurring sequences.

A "substitution" results from the replacement of one or more nucleotides or amino acids by different nucleotides or amino acids, respectively.

As used herein, a nucleic acid sequence, even if internal to a larger oligonucleotide or polynucleotide, also may be said to have 5' and 3' ends. In either a linear or circular DNA molecule, discrete elements are referred to as being "upstream" or 5' of the "downstream" or 3' elements. This terminology reflects the fact that transcription proceeds in a 5' to 3' fashion along the DNA strand. Typically, promoter and enhancer elements that direct transcription of a linked gene are generally located 5' or upstream of the coding region. However, enhancer elements can exert their effect even when located 3' of the promoter element and the coding region. Transcription termination and polyadenylation signals are located 3' or downstream of the coding region.

The term "wild-type" when made in reference to a gene refers to a gene which has the characteristics of a gene isolated from a naturally occurring source. The term "wild-type" when made in reference to a gene product refers to a gene product which has the characteristics of a gene product isolated from a naturally occurring source. A wild-type gene is that which is most frequently observed in a population and is thus arbitrarily designated the "normal" or "wild-type" form of the gene. In contrast, the term "modified" or "mutant" when made in reference to a gene or to a gene product refers, respectively, to a gene or to a gene product which displays modifications in sequence and/or functional properties (i.e., altered characteristics) when compared to the wild-type gene or gene product. It is noted that naturally-occurring mutants can be isolated; these are identified by the fact that they have altered characteristics when compared to the wild-type gene or gene product.

The term "antisense" as used herein refers to a deoxyribonucleotide sequence whose sequence of deoxyribonucleotide residues is in reverse 5' to 3' orientation in relation to the sequence of deoxyribonucleotide residues in a sense strand of a DNA duplex. A "sense strand" of a DNA duplex refers to a strand in a DNA duplex which is transcribed by a cell in its natural state into a "sense mRNA." Thus an "antisense" sequence is a sequence having the same sequence as the non-coding strand in a DNA duplex. The term "antisense RNA" refers to a RNA transcript that is complementary to all or part of a target primary transcript or MRNA and that blocks the expression of a target gene by interfering with the processing, transport and/or translation of its primary transcript or mRNA. The complementarity of an antisense RNA may be with any part of the specific gene transcript (i.e., at the 5' non-coding sequence, 3' non-coding sequence, introns, or the coding sequence). Once an antisense RNA is introduced into a cell, this transcribed strand combines with natural mRNA produced by the cell to form duplexes. These duplexes then block either the further transcription of the mRNA or its translation. In this manner, mutant phenotypes may be generated. The term "antisense strand" is used in reference to a nucleic acid strand that is complementary to the "sense" strand. The designation (−) (i.e., "negative") is sometimes used in reference to the antisense strand, with the designation (+) sometimes used in reference to the sense (i.e., "positive") strand. In addition, as used herein, antisense RNA may contain regions of ribozyme sequences that increase the efficacy of antisense RNA to block gene expression. "Ribozyme" refers to a catalytic RNA and includes sequence-specific endoribonucleases. "Antisense inhibition" refers to the production of antisense RNA transcripts capable of preventing the expression of the target protein. Antisense DNA or RNA may be produced by any method, including synthesis by splicing the gene(s) of interest in a reverse orientation to a viral promoter which permits the synthesis of a coding strand.

As used herein, the term "overexpression" refers to the production of a gene product in transgenic organisms that exceeds levels of production in normal or non-transformed organisms. As used herein, the term "cosuppression" refers to the expression of a foreign gene which has substantial homology to an endogenous gene resulting in the suppression of expression of both the foreign and the endogenous gene. As used herein, the term "altered levels" refers to the production of gene product(s) in transgenic organisms in amounts or proportions that differ from that of normal or non-transformed organisms.

The term "recombinant" when made in reference to a DNA molecule refers to a DNA molecule which is comprised of segments of DNA joined together by means of molecular biological techniques. The term "recombinant" when made in reference to a protein or a polypeptide refers to a protein molecule which is expressed using a recombinant DNA molecule.

As used herein, the terms "restriction endonucleases" and "restriction enzymes" refer to bacterial enzymes, each of which cut double-stranded DNA at or near a specific nucleotide sequence.

The term "nucleotide sequence of interest" refers to any nucleotide sequence, the manipulation of which may be deemed desirable for any reason (e.g., confer improved qualities), by one of ordinary skill in the art. Such nucleotide sequences include, but are not limited to, coding sequences of structural genes (e.g., reporter genes, selection marker genes, oncogenes, drug resistance genes, growth factors, etc.), and non-coding regulatory sequences which do not encode an mRNA or protein product, (e.g., promoter sequence, polyadenylation sequence, termination sequence, enhancer sequence, etc.).

As used herein the term "coding region" when used in reference to structural gene refers to the nucleotide sequences which encode the amino acids found in the nascent polypeptide as a result of translation of a mRNA molecule. Typically, the coding region is bounded on the 5' side by the nucleotide triplet "ATG" which encodes the initiator methionine and on the 3' side by a stop codon (e.g., TAA, TAG, TGA). In some cases the coding region is also known to initiate by a nucleotide triplet "TTG".

As used herein, the terms "complementary" or "complementarity" when used in reference to polynucleotides refer to polynucleotides which are related by the base-pairing rules. For example, for the sequence 5'-AGT-3' is complementary to the sequence 5'-ACT-3'. Complementarity may be "partial," in which only some of the nucleic acids' bases are matched according to the base pairing rules. Or, there may be "complete" or "total" complementarity between the nucleic acids. The degree of complementarity between nucleic acid strands has significant effects on the efficiency and strength of hybridization between nucleic acid strands. This is of particular importance in amplification reactions, as well as detection methods which depend upon binding between nucleic acids.

A "complement" of a nucleic acid sequence as used herein refers to a nucleotide sequence whose nucleic acids show total complementarity to the nucleic acids of the nucleic acid sequence.

The term "homology" when used in relation to nucleic acids refers to a degree of complementarity. There may be partial homology or complete homology (i.e., identity). "Sequence identity" refers to a measure of relatedness between two or more nucleic acids or proteins, and is given as a percentage with reference to the total comparison length. The identity calculation takes into account those nucleotide or amino acid residues that are identical and in the same relative positions in their respective larger sequences. Calculations of identity may be performed by algorithms contained within computer programs such as "GAP" (Genetics Computer Group, Madison, Wis.) and "ALIGN" (DNAStar, Madison, Wis.). A partially complementary sequence is one that at least partially inhibits a completely complementary sequence from hybridizing to a target nucleic acid is referred to using the functional term "substantially homologous." The inhibition of hybridization of the completely complementary sequence to the target sequence may be examined using a hybridization assay (Southern or Northern blot, solution hybridization and the like) under conditions of low stringency. A substantially homologous sequence or probe will compete for and inhibit the binding (i.e., the hybridization) of a sequence which is completely homologous to a target under conditions of low stringency. This is not to say that conditions of low stringency are such that non-specific binding is permitted; low stringency conditions require that the binding of two sequences to one another be a specific (i.e., selective) interaction. The absence of non-specific binding may be tested by the use of a second target which lacks even a partial degree of complementarity (e.g., less than about 30% identity); in the absence of non-specific binding the probe will not hybridize to the second non-complementary target.

When used in reference to a double-stranded nucleic acid sequence such as a cDNA or genomic clone, the term "substantially homologous" refers to any probe which can hybridize to either or both strands of the double-stranded nucleic acid sequence under conditions of low stringency as described herein.

The art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions. The term "hybridization" as used herein includes "any process by which a strand of nucleic acid joins with a complementary strand through base pairing" (Coombs (1994) *Dictionary of Biotechnology*, Stockton Press, New York N.Y.).

As used herein, the term "$T_m$" is used in reference to the "melting temperature." The melting temperature is the temperature at which a population of double-stranded nucleic acid molecules becomes half dissociated into single strands. The equation for calculating the $T_m$ of nucleic acids is well known in the art. As indicated by standard references, a simple estimate of the $T_m$ value may be calculated by the equation: $T_m=81.5+0.41(\% \text{ G+C})$, when a nucleic acid is in aqueous solution at 1 M NaCl (See e.g., Anderson and Young (1985) Quantitative Filter Hybridisation, in *Nucleic Acid Hybridisation*). Other references include more sophisticated computations which take structural as well as sequence characteristics into account for the calculation of $T_m$.

"Stringency" typically occurs in a range from about $T_m-5°$ C. (5° C. below the $T_m$ of the probe) to about 20° C. to 25° C. below $T_m$. As will be understood by those of skill in the art, a stringent hybridization can be used to identify or detect identical polynucleotide sequences or to identify or detect similar or related polynucleotide sequences. "Stringency" when used in reference to nucleic acid hybridization typically occurs in a range from about $T_m-5°$ C. (5° C. below the $T_m$ of the probe) to about 20° C. to 25° C. below $T_m$.

Low stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.1% SDS, 5×Denhardt's reagent [50×Denhardt's contains per 500 ml: 5 g Ficoll (Type 400, Pharmacia), 5 g BSA (Fraction V; Sigma)] and 100_g/ml denatured salmon sperm DNA followed by washing in a solution comprising 5×SSPE, 0.1% SDS at 42° C. when a probe of about 500 nucleotides in length is employed.

High stringency conditions when used in reference to nucleic acid hybridization comprise conditions equivalent to binding or hybridization at 42° C. in a solution consisting of 5×SSPE (43.8 g/l NaCl, 6.9 g/l $NaH_2PO_4.H_2O$ and 1.85 g/l EDTA, pH adjusted to 7.4 with NaOH), 0.5% SDS, 5×Denhardt's reagent and 100_g/ml denatured salmon sperm DNA followed by washing in a solution comprising 0.1×SSPE, 1.0% SDS at 42° C. when a probe of about 500 nucleotides in length is employed.

When used in reference to nucleic acid hybridization the art knows well that numerous equivalent conditions may be employed to comprise either low or high stringency conditions; factors such as the length and nature (DNA, RNA, base composition) of the probe and nature of the target (DNA, RNA, base composition, present in solution or immobilized, etc.) and the concentration of the salts and other components (e.g., the presence or absence of formamide, dextran sulfate, polyethylene glycol) are considered and the hybridization solution may be varied to generate conditions of either low or high stringency hybridization different from, but equivalent to, the above listed conditions.

As used herein the term "hybridization complex" refers to a complex formed between two nucleic acid sequences by virtue of the formation of hydrogen bounds between complementary G and C bases and between complementary A and T bases; these hydrogen bonds may be further stabilized by base stacking interactions. The two complementary nucleic acid sequences hydrogen bond in an antiparallel configuration. A hybridization complex may be formed in solution (e.g., $C_0t$ or $R_0t$ analysis) or between one nucleic acid sequence present in solution and another nucleic acid sequence immobilized to a solid support (e.g., a nylon membrane or a nitrocellulose filter as employed in Southern and Northern blotting, dot blotting or a glass slide as employed in in situ hybridization, including FISH [fluorescent in situ hybridization]).

"Alternations in the polynucleotide" as used herein comprise any alteration in the sequence of polynucleotides encoding histidine kinase, including deletions, insertions, and point mutations that may be detected using hybridization assays. Included within this definition is the detection of alterations to the genomic DNA sequence which encodes histidine kinase (e.g., by alterations in pattern of restriction enzyme fragments capable of hybridizing to any sequence such as SEQ ID NOS:1–4, e.g., RFLP analysis, the inability of a selected fragment of any sequence to hybridize to a sample of genomic DNA, e.g., using allele-specific oligonucleotide probes, improper or unexpected hybridization, such as hybridization to a locus other than the normal chromosomal locus for the histidine kinase gene, e.g., using FISH to metaphase chromosomes spreads, etc.).

The term "derivative" as used herein refers to the chemical modification of a nucleic acid encoding acyl-CoA structures. Illustrative of such modifications would be replacement of hydrogen by an alkyl, acyl, or amino group. A nucleic acid derivative would encode a polypeptide which retains essential biological characteristics of naturally-occurring acyl-CoA thioesterase.

A "variant" in regard to amino acid sequences is used to indicate an amino acid sequence that differs by one or more amino acids from another, usually related amino acid. The variant may have "conservative" changes, wherein a substituted amino acid has similar structural or chemical properties (e.g., replacement of leucine with isoleucine). More rarely, a variant may have "non-conservative" changes, e.g., replacement of a glycine with a tryptophan. Similar minor variations may also include amino acid deletions or insertions (i.e., additions), or both. Guidance in determining which and how many amino acid residues may be substituted, inserted or deleted without abolishing biological or immunological activity may be found using computer programs well known in the art, for example, DNAStar software. Thus, it is contemplated that this definition will encompass variants of acyl-CoA thioesterases. Such variants can be tested in functional assays, such as growth inhibition assays.

As used herein the term "portion" in reference to an amino acid sequence or a protein (as in "a portion of an amino acid sequence") refers to fragments of that protein. The fragments may range in size from four amino acid residues to the entire amino acid sequence minus one amino acid. Thus, a protein "comprising at least a portion of an amino acid sequence encoding an acyl-CoA thioesterase," encompasses the full-length acyl-CoA thioesterase and fragments thereof.

Polypeptide molecules are said to have an "amino terminus" (N-terminus) and a "carboxy terminus" (C-terminus) because peptide linkages occur between the backbone amino group of a first amino acid residue and the backbone carboxyl group of a second amino acid residue. Typically, the terminus of a polypeptide at which a new linkage would be to the carboxy-terminus of the growing polypeptide chain, and polypeptide sequences are written from left to right beginning at the amino terminus.

As used herein, the term "host cell" refers to any cell capable of expressing a functional gene and/or gene product introduced from another cell or organism. This definition includes, but is not limited to E. coli and other cells used as expression vectors to produce acyl-CoA thioesterase, in particular plant acyl-CoA thioesterases.

As used herein, the term "fusion protein" refers to a chimeric protein containing the protein of interest (e.g., ACHs and fragments thereof) joined to an exogenous protein fragment (e.g., the fusion partner which consists of a non-ACH protein). The fusion partner may enhance the solubility of ACH protein as expressed in a host cell, may provide an affinity tag to allow purification of the recombinant fusion protein from the host cell or culture supernatant, or both. If desired, the fusion protein may be removed from the protein of interest (e.g., ACH or fragments thereof) by a variety of enzymatic or chemical means know to the art.

As used herein, the term "transit peptide" refers to the N-terminal extension of a protein that serves as a signal for uptake and transport of that protein into an organelle such as a plastid or mitochondrion.

The term "isolated" when used in relation to a nucleic or amino acid, as in "an isolated nucleic acid sequence" or "an isolated amino acid sequence" refers to a nucleic acid sequence or amino acid that is identified and separated from at least one contaminant nucleic acid or amino acid with which it is ordinarily associated in its natural source. Isolated nucleic acid is nucleic acid present in a form or setting that is different from that in which it is found in nature. In contrast, non-isolated nucleic acids are nucleic acids such as DNA and RNA which are found in the state they exist in nature. For example, a given DNA sequence (e.g., a gene) is found on the host cell chromosome in proximity to neighboring genes; RNA sequences, such as a specific mRNA sequence encoding a specific protein, are found in the cell as a mixture with numerous other mRNAs which encode a multitude of proteins. However, an isolated nucleic acid sequence comprising SEQ ID NO:1 includes, by way of example, such nucleic acid sequences in cells which ordinarily contain SEQ ID NO:1 where the nucleic acid sequence is in a chromosomal or extrachromosomal location different from that of natural cells, or is otherwise flanked by a different nucleic acid sequence than that found in nature. The isolated nucleic acid sequence may be present in single-stranded or double-stranded form. When an isolated nucleic acid sequence is to be utilized to express a protein, the nucleic acid sequence will contain at a minimum at least a portion of the sense or coding strand (i.e., the nucleic acid sequence may be single-stranded). Alternatively, it may contain both the sense and anti-sense strands (i.e., the nucleic acid sequence may be double-stranded).

As used herein, the term "purified" refers to molecules, either nucleic or amino acid sequences, that are removed from their natural environment, isolated or separated. An "isolated nucleic acid sequence" is therefore a purified nucleic acid sequence. "Substantially purified" molecules are at least 60% free, preferably at least 75% free, and more preferably at least 90% free from other components with which they are naturally associated.

As used herein, the terms "vector" and "vehicle" are used interchangeably in reference to nucleic acid molecules that transfer DNA segment(s) from one cell to another. Vectors may include plasmids, bacteriophages, viruses, cosmids, and the like.

The term "expression vector" or "expression cassette" as used herein refers to a recombinant DNA molecule containing a desired coding sequence and appropriate nucleic acid sequences necessary for the expression of the operably linked coding sequence in a particular host organism. Nucleic acid sequences necessary for expression in prokaryotes usually include a promoter, an operator (optional), and a ribosome binding site, often along with other sequences. Eukaryotic cells are known to utilize promoters, enhancers, and termination and polyadenylation signals.

The terms "targeting vector" or "targeting construct" refer to oligonucleotide sequences comprising a gene of interest flanked on either side by a recognition sequence which is capable of homologous recombination of the DNA sequence located between the flanking recognition sequences.

The terms "in operable combination," "in operable order," and "operably linked" as used herein refer to the linkage of nucleic acid sequences in such a manner that a nucleic acid molecule capable of directing the transcription of a given gene and/or the synthesis of a desired protein molecule is produced. The term also refers to the linkage of amino acid sequences in such a manner so that a functional protein is produced.

The term "selectable marker" as used herein, refer to a gene which encodes an enzyme having an activity that confers resistance to an antibiotic or drug upon the cell in which the selectable marker is expressed. Selectable markers may be "positive" or "negative." Examples of positive selectable markers include the neomycin phosphotrasferase (NPTII) gene which confers resistance to G418 and to kanamycin, and the bacterial hygromycin phosphotransferase gene (hyg), which confers resistance to the antibiotic hygromycin. Negative selectable markers encode an enzymatic activity whose expression is cytotoxic to the cell when grown in an appropriate selective medium. For example, the HSV-tk gene is commonly used as a negative selectable marker. Expression of the HSV-tk gene in cells grown in the presence of gancyclovir or acyclovir is cytotoxic; thus, growth of cells in selective medium containing gancyclovir or acyclovir selects against cells capable of expressing a functional HSV TK enzyme.

Transcriptional control signals in eukaryotes comprise "promoter" and "enhancer" elements. Promoters and enhancers consist of short arrays of DNA sequences that interact specifically with cellular proteins involved in transcription (Maniatis, et al., Science 236:1237, 1987). Promoter and enhancer elements have been isolated from a variety of eukaryotic sources including genes in yeast, insect, mammalian and plant cells. Promoter and enhancer elements have also been isolated from viruses and analogous control elements, such as promoters, are also found in prokaryotes. The selection of a particular promoter and enhancer depends on the cell type used to express the protein of interest. Some eukaryotic promoters and enhancers have a broad host range while others are functional in a limited subset of cell types (for review, see Voss, et al., Trends Biochem. Sci., 11:287, 1986; and Maniatis, et al., supra 1987).

The terms "promoter element," "promoter," or "promoter sequence" as used herein, refer to a DNA sequence that is located at the 5' end (i.e. precedes) the protein coding region of a DNA polymer. The location of most promoters known in nature precedes the transcribed region. The promoter functions as a switch, activating the expression of a gene. If the gene is activated, it is said to be transcribed, or participating in transcription. Transcription involves the synthesis of mRNA from the gene. The promoter, therefore, serves as a transcriptional regulatory element and also provides a site for initiation of transcription of the gene into mRNA.

Promoters may be tissue specific or cell specific. The term "tissue specific" as it applies to a promoter refers to a promoter that is capable of directing selective expression of a nucleotide sequence of interest to a specific type of tissue (e.g., seeds) in the relative absence of expression of the same nucleotide sequence of interest in a different type of tissue (e.g., leaves). Tissue specificity of a promoter may be evaluated by, for example, operably linking a reporter gene to the promoter sequence to generate a reporter construct, introducing the reporter construct into the genome of a plant such that the reporter construct is integrated into every tissue of the resulting transgenic plant, and detecting the expression of the reporter gene (e.g., detecting mRNA, protein, or the activity of a protein encoded by the reporter gene) in different tissues of the transgenic plant. The detection of a greater level of expression of the reporter gene in one or more tissues relative to the level of expression of the reporter gene in other tissues shows that the promoter is specific for the tissues in which greater levels of expression are detected. The term "cell type specific" as applied to a promoter refers to a promoter which is capable of directing selective expression of a nucleotide sequence of interest in a specific type of cell in the relative absence of expression of the same nucleotide sequence of interest in a different type of cell within the same tissue. The term "cell type specific" when applied to a promoter also means a promoter capable of promoting selective expression of a nucleotide sequence of interest in a region within a single tissue. Cell type specificity of a promoter may be assessed using methods well known in the art, e.g., immunohistochemical staining. Briefly, tissue sections are embedded in paraffin, and paraffin sections are reacted with a primary antibody which is specific for the polypeptide product encoded by the nucleotide sequence of interest whose expression is controlled by the promoter. A labeled (e.g., peroxidase conjugated) secondary antibody which is specific for the primary antibody is allowed to bind to the sectioned tissue and specific binding detected (e.g., with avidin/biotin) by microscopy.

Promoters may be constitutive or regulatable. The term "constitutive" when made in reference to a promoter means that the promoter is capable of directing transcription of an operably linked nucleic acid sequence in the absence of a stimulus (e.g., heat shock, chemicals, light, etc.). Typically, constitutive promoters are capable of directing expression of a transgene in substantially any cell and any tissue. Exemplary constitutive plant promoters include, but are not limited to 35S Cauliflower Mosaic Virus (CaMV 35S; see e.g., U.S. Pat. No. 5,352,605, incorporated herein by reference), mannopine synthase, octopine synthase (ocs), superpromoter (see e.g., WO 95/14098), and ubi3 (see e.g., Garbarino and Belknap (1994) Plant Mol. Biol. 24:119–127) promoters. Such promoters have been used successfully to direct the expression of heterologous nucleic acid sequences in transformed plant tissue.

In contrast, a "regulatable" promoter is one which is capable of directing a level of transcription of an operably linked nuclei acid sequence in the presence of a stimulus (e.g., heat shock, chemicals, light, etc.) which is different from the level of transcription of the operably linked nucleic acid sequence in the absence of the stimulus.

As used herein, the term "regulatory element" refers to a genetic element that controls some aspect of the expression of nucleic acid sequence(s). For example, a promoter is a regulatory element that facilitates the initiation of transcription of an operably linked coding region. Other regulatory elements include splicing signals, polyadenylation signals, termination signals, etc.

The enhancer and/or promoter may be "endogenous" or "exogenous" or "heterologous." An "endogenous" enhancer or promoter is one that is naturally linked with a given gene in the genome. An "exogenous" or "heterologous" enhancer or promoter is one that is placed in juxtaposition to a gene by means of genetic manipulation (i.e., molecular biological techniques) such that transcription of the gene is directed by the linked enhancer or promoter.

The presence of "splicing signals" on an expression vector often results in higher levels of expression of the recombinant transcript in eukaryotic host cells. Splicing signals mediate the removal of introns from the primary RNA transcript and consist of a splice donor and acceptor site (Sambrook, et al. (1989) *Molecular Cloning: A Laboratory Manual,* 2nd ed. (Cold Spring Harbor Laboratory Press, New York) pp. 16.7–16.8). A commonly used splice donor and acceptor site is the splice junction from the 16S RNA of SV40.

Efficient expression of recombinant DNA sequences in eukaryotic cells requires expression of signals directing the efficient termination and polyadenylation of the resulting transcript. Transcription termination signals are generally found downstream of the polyadenylation signal and are a few hundred nucleotides in length. The term "poly(A) site" or "poly(A) sequence" as used herein denotes a DNA sequence which directs both the termination and polyadenylation of the nascent RNA transcript. Efficient polyadenylation of the recombinant transcript is desirable, as transcripts lacking a poly(A) tail are unstable and are rapidly degraded. The poly(A) signal utilized in an expression vector may be "heterologous" or "endogenous." An endogenous poly(A) signal is one that is found naturally at the 3' end of the coding region of a given gene in the genome. A heterologous poly(A) signal is one which has been isolated from one gene and positioned 3' to another gene. A commonly used heterologous poly(A) signal is the SV40 poly (A) signal. The SV40 poly(A) signal is contained on a 237 bp BamHI/BclI restriction fragment and directs both termination and polyadenylation (Sambrook, supra, at 16.6–16.7).

The terms "infecting" and "infection" with a bacterium refer to co-incubation of a target biological sample, (e.g., cell, tissue, etc.) with the bacterium under conditions such that nucleic acid sequences contained within the bacterium are introduced into one or more cells of the target biological sample.

The term "Agrobacterium" refers to a soil-borne, Gram-negative, rod-shaped phytopathogenic bacterium which causes crown gall. The term "Agrobacterium" includes, but is not limited to, the strains *Agrobacterium tumefaciens*, (which typically causes crown gall in infected plants), and *Agrobacterium rhizogens* (which causes hairy root disease in infected host plants). Infection of a plant cell with Agrobacterium generally results in the production of opines (e.g., nopaline, agropine, octopine etc.) by the infected cell. Thus, Agrobacterium strains which cause production of nopaline (e.g., strain LBA4301, C58, A208) are referred to as "nopaline-type" Agrobacteria; Agrobacterium strains which cause production of octopine (e.g., strain LBA4404, Ach5, B6) are referred to as "octopine-type" Agrobacteria; and Agrobacterium strains which cause production of agropine (e.g., strain EHA105, EHA101, A281) are referred to as "agropine-type" Agrobacteria.

The terms "bombarding, "bombardment," and "biolistic bombardment" refer to the process of accelerating particles towards a target biological sample (e.g., cell, tissue, etc.) to effect wounding of the cell membrane of a cell in the target biological sample and/or entry of the particles into the target biological sample. Methods for biolistic bombardment are known in the art (e.g., U.S. Pat. No. 5,584,807, the contents of which are incorporated herein by reference), and are commercially available (e.g., the helium gas-driven microprojectile accelerator (PDS-1000/He, BioRad).

The term "microwounding" when made in reference to plant tissue refers to the introduction of microscopic wounds in that tissue. Microwounding may be achieved by, for example, particle bombardment as described herein.

The term "transfection" as used herein refers to the introduction of foreign DNA into eukaryotic cells. Transfection may be accomplished by a variety of means known to the art including calcium phosphate-DNA co-precipitation, DEAE-dextran-mediated transfection, polybrene-mediated transfection, electroporation, microinjection, liposome fusion, lipofection, protoplast fusion, retroviral infection, and biolistics.

The term "transgenic" when used in reference to a cell refers to a cell which contains a transgene, or whose genome has been altered by the introduction of a transgene. The term "transgenic" when used in reference to a tissue or to a plant refers to a tissue or plant, respectively, which comprises one or more cells that contain a transgene, or whose genome has been altered by the introduction of a transgene. Transgenic cells, tissues and plants may be produced by several methods including the introduction of a "transgene" comprising nucleic acid (usually DNA) into a target cell or integration of the transgene into a chromosome of a target cell by way of human intervention, such as by the methods described herein.

The term "transgene" as used herein refers to any nucleic acid sequence which is introduced into the genome of a cell by experimental manipulations. A transgene may be an "endogenous DNA sequence," or a "heterologous DNA sequence" (i.e., "foreign DNA"). The term "endogenous DNA sequence" refers to a nucleotide sequence which is naturally found in the cell into which it is introduced so long as it does not contain some modification (e.g., a point mutation, the presence of a selectable marker gene, etc.) relative to the naturally-occurring sequence. The term "heterologous DNA sequence" refers to a nucleotide sequence which is ligated to, or is manipulated to become ligated to, a nucleic acid sequence to which it is not ligated in nature, or to which it is ligated at a different location in nature. Heterologous DNA is not endogenous to the cell into which it is introduced, but has been obtained from another cell. Heterologous DNA also includes an endogenous DNA sequence which contains some modification. Generally, although not necessarily, heterologous DNA encodes RNA and proteins that are not normally produced by the cell into which it is expressed. Examples of heterologous DNA include reporter genes, transcriptional and translational regulatory sequences, selectable marker proteins (e.g., proteins which confer drug resistance), etc.

The term "foreign gene" refers to any nucleic acid (e.g., gene sequence) which is introduced into the genome of a cell by experimental manipulations and may include gene sequences found in that cell so long as the introduced gene contains some modification (e.g., a point mutation, the presence of a selectable marker gene, etc.) relative to the naturally-occurring gene.

The term "transformation" as used herein refers to the introduction of a transgene into a cell. Transformation of a cell may be stable or transient. The term "transient transformation" or "transiently transformed" refers to the introduction of one or more transgenes into a cell in the absence of integration of the transgene into the host cell's genome. Transient transformation may be detected by, for example, enzyme-linked immunosorbent assay (ELISA) which detects the presence of a polypeptide encoded by one or more of the transgenes. Alternatively, transient transformation may be detected by detecting the activity of the protein (e.g., _-glucuronidase) encoded by the transgene. The term "transient transformant" refers to a cell which has transiently incorporated one or more transgenes. In contrast, the term "stable transformation" or "stably transformed" refers to the introduction and integration of one or more transgenes into the genome of a cell. Stable transformation of a cell may be detected by Southern blot hybridization of genomic DNA of the cell with nucleic acid sequences which are capable of binding to one or more of the transgenes. Alternatively, stable transformation of a cell may also be detected by the polymerase chain reaction of genomic DNA of the cell to amplify transgene sequences. The term "stable transformant" refers to a cell which has stably integrated one or more transgenes into the genomic DNA. Thus, a stable transformant is distinguished from a transient transformant in that, whereas genomic DNA from the stable transformant contains one or more transgenes, genomic DNA from the transient transformant does not contain a transgene.

The term "amplification" is defined as the production of additional copies of a nucleic acid sequence and is generally carried out using polymerase chain reaction technologies well known in the art (Dieffenbach and G S Dvekler (1995) *PCR Primer, a Laboratory Manual*, Cold Spring Harbor Press, Plainview N.Y.). As used herein, the term "polymerase chain reaction" ("PCR") refers to the methods disclosed in U.S. Pat. Nos. 4,683,195, 4,683,202 and 4,965,188, all of which are incorporated herein by reference, which describe a method for increasing the concentration of a segment of a target sequence in a mixture of genomic DNA without cloning or purification. This process for amplifying the target sequence consists of introducing a large excess of two oligonucleotide primers to the DNA mixture containing the desired target sequence, followed by a precise sequence of thermal cycling in the presence of a DNA polymerase. The two primers are complementary to their respective strands of the double stranded target sequence. To effect amplification, the mixture is denatured and the primers then annealed to their complementary sequences within the target molecule. Following annealing, the primers are extended with a polymerase so as to form a new pair of complementary strands. The steps of denaturation, primer annealing and polymerase extension can be repeated many times (i.e., denaturation, annealing and extension constitute one "cycle"; there can be numerous "cycles") to obtain a high concentration of an amplified segment of the desired target sequence. The length of the amplified segment of the desired target sequence is determined by the relative positions of the primers with respect to each other, and therefore, this length is a controllable parameter. By virtue of the repeating aspect of the process, the method is referred to as the "polymerase chain reaction" (hereinafter "PCR"). Because the desired amplified segments of the target sequence become the predominant sequences (in terms of concentration) in the mixture, they are said to be "PCR amplified."

With PCR, it is possible to amplify a single copy of a specific target sequence in genomic DNA to a level detectable by several different methodologies (e.g., hybridization with a labeled probe; incorporation of biotinylated primers followed by avidin-enzyme conjugate detection; and/or incorporation of $^{32}$P-labeled deoxyribonucleotide triphosphates, such as dCTP or dATP, into the amplified segment). In addition to genomic DNA, any oligonucleotide sequence can be amplified with the appropriate set of primer molecules. In particular, the amplified segments created by the PCR process itself are, themselves, efficient templates for subsequent PCR amplifications. Amplified target sequences may be used to obtain segments of DNA (e.g., genes) for the construction of targeting vectors, transgenes, etc.

As used herein, the term "sample template" refers to a nucleic acid originating from a sample which is analyzed for the presence of "target". In contrast, "background template" is used in reference to nucleic acid other than sample template, which may or may not be present in a sample. Background template is most often inadvertent. It may be the result of carryover, or it may be due to the presence of nucleic acid contaminants sought to be purified away from the sample. For example, nucleic acids other than those to be detected may be present as background in a test sample.

As used herein, the term "primer" refers to an oligonucleotide, whether occurring naturally (e.g., as in a purified restriction digest) or produced synthetically, which is capable of acting as a point of initiation of nucleic acid synthesis when placed under conditions in which synthesis of a primer extension product which is complementary to a nucleic acid strand is induced (i.e., in the presence of nucleotides, an inducing agent such as DNA polymerase, and under suitable conditions of temperature and pH). The primer is preferably single-stranded for maximum efficiency in amplification, but may alternatively be double-stranded. If double-stranded, the primer is first treated to separate its strands before being used to prepare extension products. Preferably, the primer is an oligodeoxyribonucleotide. The primer must be sufficiently long to prime the synthesis of extension products in the presence of the inducing agent. The exact lengths of the primers will depend on many factors, including temperature, source of primer and use of the method.

As used herein, the term "probe" refers to an oligonucleotide (i.e., a sequence of nucleotides), whether occurring naturally (e.g., as in a purified restriction digest) or produced synthetically, recombinantly or by PCR amplification, which is capable of hybridizing to another oligonucleotide of interest. A probe may be single-stranded or double-stranded. Probes are useful in the detection, identification and isolation of particular gene sequences. It is contemplated that the probe used in the present invention is labeled with any "reporter molecule," so that it is detectable in a detection system, including, but not limited to enzyme (i.e., ELISA, as well as enzyme-based histochemical assays), fluorescent, radioactive, and luminescent systems. It is not intended that the present invention be limited to any particular detection system or label. The terms "reporter molecule" and "label" are used herein interchangeably. In addition to probes, primers and deoxynucleoside triphosphates may contain labels; these labels may comprise, but are not limited to, $^{32}$P, $^{33}$P, $^{35}$S, enzymes, or fluorescent molecules (e.g., fluorescent dyes).

As used herein, the term "polymerase" refers to any polymerase suitable for use in the amplification of nucleic acids of interest. It is intended that the term encompass such DNA polymerases as Taq DNA polymerase obtained from *Thermus aquaticus*, although other polymerases, both thermostable and thermolabile are also encompassed by this definition.

As used herein, the terms "PCR product" and "amplification product" refer to the resultant mixture of compounds after two or more cycles of the PCR steps of denaturation, annealing and extension are complete. These terms encompass the case where there has been amplification of one or more segments of one or more target sequences.

As used herein, the term "nested primers" refers to primers that anneal to the target sequence in an area that is inside the annealing boundaries used to start PCR. (See, Mullis, KB et al. (1986) Cold Spring Harbor Symposia, Vol. LI, pp. 263–273). Because the nested primers anneal to the target inside the annealing boundaries of the starting primers, the predominant PCR-amplified product of the starting primers is necessarily a longer sequence, than that defined by the annealing boundaries of the nested primers.

The PCR-amplified product of the nested primers is an amplified segment of the target sequence that cannot, therefore, anneal with the starting primers.

As used herein, the term "amplification reagents" refers to those reagents (deoxyribonucleoside triphosphates, buffer, etc.), needed for amplification except for primers, nucleic acid template and the amplification enzyme.

The term "sample" as used herein refers to any type of material obtained from plants, humans or other animals (e.g., any bodily fluid or tissue), cell or tissue cultures, cell lines, or any in vitro culture. Indeed, the term "sample" as used herein is used in its broadest sense. A biological sample suspected of containing nucleic acid encoding acyl-CoA thioesterase may comprise a cell, chromosomes isolated from a cell (e.g., a spread of metaphase chromosomes), genomic DNA (in solution or bound to a solid support such as for Southern blot analysis), RNA (in solution or bound to a solid support such as for Northern blot analysis), cDNA (in solution or bound to a solid support) and the like. A sample suspected of containing a protein may comprise a cell, a portion of a tissue, an extract containing one or more proteins and the like.

As used herein, the term "eukaryote" refers to organisms distinguishable from "prokaryotes." It is intended that the term encompass all organisms with cells that exhibit the usual characteristics of eukaryotes such as the presence of a true nucleus bounded by a nuclear membrane, within which lie the chromosomes, the presence of membrane-bound organelles, and other characteristics commonly observed in eukaryotic organisms. Thus, the term includes, but is not limited to such organisms as plants, fungi, protozoa, and animals (e.g., humans).

As used herein, the term "antimetabolite" refers to any substance with a close structural resemblance to another, essential substance (i.e., metabolite) that is required for normal physiologic function. Typically, antimetabolites exert their effects by interfering with the utilization of the essential metabolite.

I. Acyl-CoA Thioesterases

Acyl-CoA thioesterases (ACHS) catalyze the following general reaction:

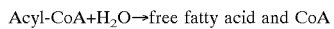

Acyl-CoA+H$_2$O→free fatty acid and CoA wherein acyl-CoA is hydrolyzed to free fatty acid and CoA. These reactions are important in lipid metabolism. For example, previous studies have shown that there is an acyl-CoA thioesterase that resides in the inner envelope of the chloroplast membrane of peas (Andrews and Keegstra, 1983), although the protein sequence was never discovered, nor was the gene for this thioesterase ever isolated. During the development of the present invention, genes were identified that code for putative peroxisomal and mitochondrial acyl-CoA thioesterases. Taken together, these enzymes have the capability of regulating acyl-CoA traffic and usage by removing, through hydrolysis, specific acyl-CoAs from the lipid metabolism pathways. Although an understanding of the mechanism is not necessary in order to make and use the present invention, it is believed that this acyl-CoA thioesterase play a role in determining the acyl-CoA molecules that leave the chloroplast. Chloroplasts typically produce and export 16 and 18 carbon acyl-CoAs. It is contemplated that if an irregular acyl-CoA is produced, the acyl-CoA thioesterase cleaves the CoA, preventing the export of this fatty acid by acyl-CoA and thus its incorporation into storage lipids. Eliminating the "proofreading activity" is contemplated as being important in applications involving plants that produce and store irregular fatty acids. However, it is not necessary to understand the mechanisms involved in this process in order to make and use the present invention.

The present invention provides four acyl-CoA thioesterase genes, designated "ACH1," "ACH2," "ACH4," and "ACH5." All of these genes were identified based upon their amino acid homology to reported acyl-CoA thioesterases; however, the genes of the present invention possess unusual amino sequences. Based upon amino acid homology analysis, it appears that these four genes are members of two classes of acyl-CoA thioesterases in Arabidopsis, These two classes are very different, as there is only about 30% identity between them.

The first class of acyl-CoA thioesterases contains genes encoding ACH1 and ACH2, which were found to be 68.7% identical to each other. These two proteins appear to be localized in peroxisomes of plants since the carboxy termini end either "AKL" or "SKL," both of which are consequence sequences for peroxisomal targeting (see FIG. 5, panel A). Both proteins also possess a unique amino-terminus sequence which is not observed in any other known acyl-CoA thioesterase (see FIG. 5, panel A). This amino-terminus sequence contains a putative cGMP binding domain (which is boxed and highlighted in FIG. 5, panel A), which has not been identified in any other known acyl-CoA thioesterase. The presence of a cGMP binding site suggests that these enzymes are likely to be controlled through signaling cascades. It is contemplated that these enzymes are involved in lipid oxidation.

The second class contains genes encoding ACH4 and ACH5, which were found to be 57.8% identical to each other, and 66.7% similar to each other, where similarity refers to amino acids with similar chemical characteristics, such as hydrophobicity, hydrophyllicity, etc. These two proteins appear to be localized to the mitochondria. These genes were identified by their amino acid homology to a rat mitochondrial acyl-CoA thioesterase gene. Furthermore, ACH4 and ACH5 each possess a unique amino terminus sequence, which is contemplated to correspond to a mitochondrial transit peptide, as mitochondrial targeting sequences are generally not conserved. Moreover, these proteins were not imported into chloroplasts, ruling out the possibility that the N-termini correspond to plastid targeting signals. Since there is no lipid oxidation that occurs in plant mitochondria, it is contemplated that these enzymes play a role in the plant mitochondrial lipid synthesis pathway that has recently been characterized (Gueguen et al. 2000). Experiments to determine the localization of these proteins fused to green fluorescent protein indicate that these fusion proteins ultimately end up in the mitochondria.

Thus, it is contemplated that these genes will find use in the development of plants containing specialized fatty acid compositions. Each of these genes is discussed in further detail below.

A. Class 1: Putative Peroxisomal Enzymes

1. ACH1

ACH1 was identified using an Arabidopsis database and shows high homology to a human acyl-CoA thioesterase (HIV1 Nef-associated acyl-CoA thioesterase). Portions of ACH1 cDNA were subcloned using a cDNA library as a template for RT-PCR reactions. Initially, the 5' and 3' ends of the gene were not identified due to the weak homology between these regions of the gene and other thioesterases. In addition, there appeared to be cDNAs of two different sizes. The discovery of an additional predicted open reading frame (ORF) positioned very closely to what had been considered the ACH1 start codon resulted in the identification of the 5' end much further upstream than originally thought. This region had gone unobserved as it bore no resemblance to other known acyl-CoA thioesterases. This extra bit of sequence, which corresponded to two extra exons of coding region, allowed the identification of cDNA clones in the database that encoded the entire ACH1 cDNA. Two clones were identified, one of which was shorter than the other and had an internal nonsense codon. The longer clone was designated as the true ACH1 cDNA. This cDNA is shown in FIG. 1 (SEQ ID NO:1), while the peptide sequence is shown in FIG. 5, Panel A (SEQ ID NO:5). FIG. 5, Panel A also indicates the putative cGMP binding domain (shown boxed and highlighted). This region has not been identified in other known acyl-CoA thioesterases.

Importantly, the C-terminus of the putative protein was "AKL," a consensus sequence for targeting to the peroxisome. The extra portion at the N-terminus bore a weak homology to cyclic-GMP (cGMP) binding proteins, indicating that the enzyme is likely to be controlled through signaling cascades. Reverse transcriptase-polymerase chain reaction (RT-PCR) was used to demonstrate the presence of mRNA in various tissues (according to protocols designed by GIBCO). Indeed, ACH1 mRNA was found to be expressed in all tissues analyzed, including dry seed, root, leaf, rosette leaves, total aerials, and siliques. RNA blot analysis showed that ACH1 is constitutively expressed at equal levels, in all tissues examined, including rosette leaves, leaves, young flowers, old flowers, and siliques.

Subsequent expression studies, in which the gene was over-expressed in *E. coli* indicated that the gene product could be successfully over-expressed, but apparently only in insoluble form. Moreover, no increased acyl-CoA thioesterase activity was observed in cell lysates, which suggests that the produced protein is likely to be improperly folded under the over-expression conditions utilized in these experiments.

At least one mutant Arabidopsis line carrying a T-DNA insertion in the ACH1 gene has been identified; mutant seeds are germinated and grown, and the effects of the mutation on plant morphological, physiological, and biochemical characteristics are evaluated. It is contemplated that, because there appears to be at least one additional acyl-CoA thioesterase in this class, the mutant plants will not be significantly different from wild-type plants. However, it is anticipated that the mutants can be crossed with a plant carrying a T-DNA insertion in the ACH2 gene, thus completely removing the activity of the enzymes of this class. This will be useful for further evaluating the function of these genes in vivo.

2. ACH2

As with ACH1, ACH2 was first identified using the human acyl-CoA thioesterase as a search tool in the Arabidopsis database. Although the full-length gene was not identified in this way, an expressed sequence tag (EST) was identified that corresponded to about 250 base pairs (bp) of the ACH2 cDNA. Using primers based on this sequence, a genomic PCR product was generated for use in screening a genomic library for the full-length gene. Subsequently, a genomic clone was isolated from a genomic phage library and sequenced. As was observed for ACH1, RNA blot hybridization indicated that ACH2 was constitutively expressed in all tissues examined.

Also as was observed for ACH1, it was recognized that the ACH2 gene had more in its 5' coding region than was originally expected. Analysis of the putative gene product revealed a protein that was 68.7% identical to ACH1, and had a consensus sequence for targeting to the peroxisome (i.e., SKL at the C-terminus). Full-length cDNA was then cloned using the RT-PCR product. As the RT-PCR seemed to be prone to mistakes, it took some time and effort to find a clone with the correct sequence. Only RT-PCR products using rosette leaf mRNA as a template yielded a product with the correct sequence. The cDNA sequence is shown in FIG. 2 (SEQ ID NO:2), while the peptide sequence is shown in FIG. 5, Panel B (SEQ ID NO:6). FIG. 5, Panel B also indicates the putative cGMP binding domain (shown boxed and highlighted). This region has not been identified in other known acyl-CoA thioesterases.

In fact, for a period of time, a sequence initially thought to be a third isoform of ACH1 and ACH2 was identified. However, once the entire gene was sequenced, it was determined that the sequence was identical to ACH2

Subsequent expression studies of ACH2, in which the gene was over-expressed as a fusion product, indicted that the gene product could be successfully over-expressed. The protein was over-expressed as both a fusion product with MBP and as a fusion product with a six histidine tag. Both fusion products were soluble, and both possessed acyl-CoA thioesterase activity, demonstrating that the gene product is an acyl-CoA thioesterase.

At least one mutant Arabidopsis line carrying a T-DNA insertion has been identified; mutant seeds are germinated and grown, and the effects of the mutation on plant morphological, physiological, and biochemical characteristics are evaluated. It is contemplated that, because there appears to be at least one additional acyl-CoA thioesterase in this class, the mutant plants will not be significantly different from wild-type plants. However, it is anticipated that the mutants can be crossed with a plant carrying a T-DNA insertion in the ACH1 gene, thus completely removing the activity of the enzymes of this class. This will be useful for further evaluating the function of these genes in vivo.

B. Class 2: Putative Mitochondrial Enzymes

1. ACH4

This gene was identified based upon its homology to a rat mitochondrial acyl-CoA thioesterase. The full-length gene was in the Arabidopsis database, but it was not originally possible to identify the exact positions of the 3' and 5' ends of the gene. Attempts to isolate the ACH4 cDNA from a lambda-PRL library and screens for a T-DNA mutant were unsuccessful. In view of these failures, a cDNA sequence obtained from Genome Systems, Inc. was sequenced. Sequencing provided the putative 5' end of the gene. The putative protein product is homologous to other known acyl-CoA thioesterases, with the exception of the N-terminus. Thus, it is contemplated that this sequence corresponds to a transit peptide which is most likely mitochondrial. Mitochondrial target sequences are generally not conserved, and thus are variable. The cDNA sequence is shown in FIG. 3 (SEQ ID NO:3), while the peptide sequence is shown in FIG. 6, Panel A (SEQ ID NO:7).

The localization of ACH4 is determined from several approaches. In vitro experiments indicated that ACH4 was not imported into chloroplasts. Based on its homology to mitochondrial homologues in other organisms, it is very likely localized to the mitochondria. Thus, in vivo experiments to determine the sub-cellular location of ACH4 with an ACH4-green fluorescent protein (GFP) construct indicate that ACH4 is ultimately localized to the mitochondria.

2. ACH5

The ACH5 genomic sequence was also identified using the Arabidopsis database. Interestingly, although a portion of the cDNA was cloned during the development of the present invention, initial work with this gene had failed to identify the 5' region. However, Genefinder was used to predict a protein product from the ACH5 gene that appeared to be correct. RT-PCR was subsequently used to amplify the putative full-length cDNA. Sequencing was then conducted on the full-length cDNA, which codes for a protein that is nearly identical to the one initially predicted by Genefinder, with the exception of a small region positioned towards the C-terminus. The cDNA sequence is shown in FIG. 4 (SEQ ID NO:4), while the peptide sequence is shown in FIG. 6, Panel B (SEQ ID NO:8).

The activity of a fusion protein, ACH5-6His, which was over-expressed in *E. coli*, was assayed in the soluble extract of lysed cells. The extract from cells expressing the fusion protein displayed an acyl-CoA thioesterase activity about 5 times greater than that observed in control cells, indicating that the gene product is an acyl-thioesterase.

Localization studies in vitro indicated that, as with ACH4, ACH5 was not imported into chloroplasts, indicating that its unique N-terminus played some other role than a plastid targeting signal. Due to its homology with other mitochondrial acyl-CoA thioesterases from other organisms, it is believed that the N-terminus serves as a mitochondrial targeting signal. Thus, in vivo experiments with an ACH5-green fluorescent protein (GFP) fusion protein construct indicate that the fusion protein is ultimately localized to the mitochondria. Thus, these results indicate that ACH5 is localized in the mitochondria, as is ACH4.

Although a T-DNA mutant plant was identified with a T-DNA insertion in the ACH5 gene, there was no visible phenotype associated with this mutant. Experiments to further characterize the function of these enzymes include the transformation of this T-DNA mutant with antisense constructs for ACH4. It is anticipated that such constructs will have varying and detrimental effects on the transformed plants.

C. Genetic Family Tree

The unique feature of ACH1 and ACH2 that sets them apart from other acyl-CoA thioesterases previously reported is a 120 amino acid extension at the N-terminus, as described above. Although all forms of life have enzymes that are homologous to ACH1 and ACH2, it appears that only plants have enzymes with this unique N-terminal extension. This was determined by searching public databases and looking for sequences similar to those of ACH1 and ACH2. Gene sequences coding for enzymes similar to ACH1 and ACH2, with the heretofore-undescribed N-terminal region, can be found in wheat, tomato, soybean, maize, rice, medicago, barley, and potato. The BLAST server at NCBI failed to find any of these other plant sequences, but they can be found by performing BLAST searches with the TIGR Gene Indices. As noted above, the N-terminal extension bears some homology to cyclic-nucleotide binding domains that bind cyclic-AMP (cAMP) or cyclic-GMP (cGMP).

Predicted amino acid sequences of these other ACH proteins were compared, and used as the basis to construct a phylogenetic tree (G. Tilton, manuscript in preparation).

D. Summary

Thus, the present invention provides nucleic acids encoding plant ACHs (e.g., SEQ ID NOs: 1–4). Other embodiments of the present invention provide nucleic acid sequences that are capable of hybridizing to SEQ ID NOs: 1–4 under conditions of high to low stringency. In some embodiments, the hybridizing nucleic acid sequence encodes a protein that retains at least one biological activity of the naturally occurring ACH from which it is derived. In preferred embodiments, hybridization conditions are based on the melting temperature ($T_m$) of the nucleic acid binding complex and confer a defined "stringency" as explained above.

In other embodiments of the present invention, variants of the disclosed ACHs are provided. In preferred embodiments, variants result from mutation, (i.e., a change in the nucleic acid sequence) and generally produce altered mRNAs or polypeptides whose structure or function may or may not be altered. Any given gene may have none, one, or many variant forms. Common mutational changes that give rise to variants are generally ascribed to deletions, additions or substitutions of nucleic acids. Each of these types of changes may occur alone, or in combination with the others, and at the rate of one or more times in a given sequence.

It is contemplated that is possible to modify the structure of a peptide having an activity (e.g., ACH activity) for such purposes as increasing synthetic activity or altering the affinity of the ACH for a particular substrate. Such modified peptides are considered functional equivalents of peptides having an activity of an ACH as defined herein. A modified peptide can be produced in which the nucleotide sequence encoding the polypeptide has been altered, such as by substitution, deletion, or addition. In some preferred embodiments of the present invention, the alteration increases synthetic activity or alters the affinity of the ACH for a particular substrate. In particularly preferred embodiments, these modifications do not significantly reduce the synthetic activity of the modified enzyme. In other words, construct "X" can be evaluated according to the following protocol in order to determine whether it is a member of the genus of modified or variant ACHs of the present invention as defined functionally, rather than structurally. In preferred embodiments, the activity of variant ACHs is evaluated using the ACH activity assay described herein at Example 4.

Moreover, as described above, variant forms of ACHs are also contemplated as being equivalent to those peptides and DNA molecules that are set forth in more detail herein. For example, it is contemplated that isolated replacement of a leucine with an isoleucine or valine, an aspartate with a glutamate, a threonine with a serine, or a similar replacement of an amino acid with a structurally related amino acid (i.e., conservative mutations) will not have a major effect on the biological activity of the resulting molecule. Accordingly, some embodiments of the present invention provide variants of ACHs disclosed herein containing conservative replacements. Conservative replacements are those that take place within a family of amino acids that are related in their side chains. Genetically encoded amino acids can be divided into four families: (1) acidic (aspartate, glutamate); (2) basic (lysine, arginine, histidine); (3) non-polar (alanine, valine, leucine, isoleucine, proline, phenylalanine, methionine, tryptophan); and (4) uncharged polar (glycine, asparagine, glutamine, cysteine, serine, threonine, tyrosine). Phenylalanine, tryptophan, and tyrosine are sometimes classified jointly as aromatic amino acids. In similar fashion, the amino acid repertoire can be grouped as (1) acidic (aspartate, glutamate); (2) basic (lysine, arginine, histidine), (3) aliphatic (glycine, alanine, valine, leucine, isoleucine, serine, threonine), with serine and threonine optionally be grouped separately as aliphatic-hydroxyl; (4) aromatic (phenylalanine, tyrosine, tryptophan); (5) amide (asparagine, glutamine); and (6) sulfur-containing (cysteine and methionine) (e.g., Stryer ed., *Biochemistry*, pg. 17–21, 2nd ed, W H Freeman and Co., 1981). Whether a change in the amino acid sequence of a peptide results in a functional homolog can be readily determined by assessing the ability of the variant peptide to function in a fashion similar to the wild-type protein. Peptides having more than one replacement can readily be tested in the same manner.

More rarely, a variant includes "nonconservative" changes (e.g., replacement of a glycine with a tryptophan). Analogous minor variations can also include amino acid deletions or insertions, or both. Guidance in determining which amino acid residues can be substituted, inserted, or deleted without abolishing biological activity can be found using computer programs (e.g., LASERGENE software, DNASTAR Inc., Madison, Wis.).

As described in more detail below, variants may be produced by methods such as directed evolution or other techniques for producing combinatorial libraries of variants, described in more detail below. In still other embodiments of the present invention, the nucleotide sequences of the present invention may be engineered in order to alter an ACH coding sequence including, but not limited to, alterations that modify the cloning, processing, localization, secretion, and/or expression of the gene product. For example, mutations may be introduced using techniques that are well known in the art (e.g., site-directed mutagenesis to insert new restriction sites, alter glycosylation patterns, or change codon preference, etc.).

In some embodiments, the present invention provides ACH polypeptides (e.g., SEQ ID NOs: 5–8). In other embodiments, the present invention provides unique cGMP-binding domains associated with ACH1 and ACH2 (i.e., SEQ ID NOS:11 and 12). Still further embodiments of the present invention provide fragments, fusion proteins or functional equivalents of ACHs. In still other embodiments of the present invention, nucleic acid sequences corresponding to a selected ACH may be used to generate recombinant DNA molecules that direct the expression of an ACH and variants in appropriate host cells. In some embodiments of the present invention, the polypeptide may be a naturally purified product, while in other embodiments it may be a product of chemical synthetic procedures, and in still other embodiments it may be produced by recombinant techniques using a prokaryotic or eukaryotic host cell (e.g., by bacterial cells in culture). In other embodiments, the polypeptides of the invention may also include an initial methionine amino acid residue.

In one embodiment of the present invention, due to the inherent degeneracy of the genetic code, DNA sequences other than SEQ ID NOs: 1–4 or 11–12, encoding substantially the same or a functionally equivalent amino acid sequence, may be used to clone and express an ACH. In general, such nucleic acid sequences hybridize to SEQ ID NOs: 1–4, as well as SEQ ID NOS:11–12, under conditions of high to low stringency as described above. As will be understood by those of skill in the art, it may be advantageous to produce ACH-encoding nucleotide sequences possessing non-naturally occurring codons. Therefore, in some preferred embodiments, codons preferred by a particular prokaryotic or eukaryotic host are selected, for example, to increase the rate of ACH expression or to produce recombinant RNA transcripts having desirable properties, such as increased synthetic activity or altered affinity of the ACH for a particular substrate.

II. Uses of ACH Polynucleotides and Polypeptides

1. Vectors for Expression of ACHs

In some embodiments of the present invention, the ACH nucleic acids are used to construct vectors for the expression of ACH polypeptides. Accordingly, the nucleic acids of the present invention may be employed for producing polypeptides by recombinant techniques. Thus, for example, the nucleic acid may be included in any one of a variety of expression vectors for expressing a polypeptide.

In some embodiments of the present invention, vectors are provided for the transfection of plant hosts to create transgenic plants. In general, these vectors comprise an ACH nucleic acid (e.g., SEQ ID NOs: 1–4) operably linked to a promoter and other regulatory sequences (e.g., enhancers, polyadenylation signals, etc.) required for expression in a plant. The ACH nucleic acid can be oriented to produce sense or antisense transcripts, depending on the desired use. In some embodiments, the promoter is a constitutive promoter (e.g., superpromoter or 35S promoter). In other embodiments, the promoter is a seed specific promoter (e.g., phaseolin promoter [See e.g., U.S. Pat. No. 5,589,616, incorporated herein by reference], napin promoter [See e.g., U.S. Pat. No. 5,608,152, incorporated herein by reference], or acyl-CoA carrier protein promoter [See e.g., U.S. Pat. No. 5,767,363, incorporated herein by reference]).

In some preferred embodiments, the vector is adapted for use in an Agrobacterium mediated transfection process (See e.g., U.S. Pat. Nos. 5,981,839; 6,051,757; 5,981,840; 5,824,877; and 4,940,838; all of which are incorporated herein by reference). Construction of recombinant Ti and Ri plasmids in general follows methods typically used with the more common bacterial vectors, such as pBR322. Additional use can be made of accessory genetic elements sometimes found with the native plasmids and sometimes constructed from foreign sequences. These may include but are not limited to structural genes for antibiotic resistance as selection genes.

There are two systems of recombinant Ti and Ri plasmid vector systems now in use. The first system is called the "cointegrate" system. In this system, the shuttle vector containing the gene of interest is inserted by genetic recombination into a non-oncogenic Ti plasmid that contains both the cis-acting and trans-acting elements required for plant transformation as, for example, in the pMLJ1 shuttle vector and the non-oncogenic Ti plasmid pGV3850. The second system is called the "binary" system in which two plasmids are used; the gene of interest is inserted into a shuttle vector containing the cis-acting elements required for plant transformation. The other necessary functions are provided in trans by the non-oncogenic Ti plasmid as exemplified by the pBIN19 shuttle vector and the non-oncogenic Ti plasmid PAL4404. Some of these vectors are commercially available.

It may be desirable to target the nucleic acid sequence of interest to a particular locus on the plant genome. Site-directed integration of the nucleic acid sequence of interest into the plant cell genome may be achieved by, for example, homologous recombination using Agrobacterium-derived sequences. Generally, plant cells are incubated with a strain of Agrobacterium which contains a targeting vector in which sequences that are homologous to a DNA sequence inside the target locus are flanked by Agrobacterium transfer-DNA (T-DNA) sequences, as previously described (U.S. Pat. No. 5,501,967, the entire contents of which are herein incorporated by reference). One of skill in the art knows that homologous recombination may be achieved using targeting vectors which contain sequences that are homologous to any part of the targeted plant gene, whether belonging to the regulatory elements of the gene, or the coding regions of the gene. Homologous recombination may be achieved at any region of a plant gene so long as the nucleic acid sequence of regions flanking the site to be targeted is known.

The nucleic acids of the present invention may also be utilized to construct vectors derived from plant (+) RNA viruses (e.g., brome mosaic virus, tobacco mosaic virus, alfalfa mosaic virus, cucumber mosaic virus, tomato mosaic virus, and combinations and hybrids thereof). Generally, the inserted ACH polynucleotide can be expressed from these vectors as a fusion protein (e.g., coat protein fusion protein) or from its own subgenomic promoter or other promoter. Methods for the construction and use of such viruses are described in U.S. Pat. Nos. 5,846,795; 5,500,360; 5,173,410; 5,965,794; 5,977,438; and 5,866,785, all of which are incorporated herein by reference.

Alternatively, vectors can be constructed for expression in hosts other plants (e.g., prokaryotic cells such as *E. coli*, yeast cells, C. elegans, and mammalian cell culture cells). In some embodiments of the present invention, vectors include, but are not limited to, chromosomal, nonchromosomal and synthetic DNA sequences (e.g., derivatives of SV40, bacterial plasmids, phage DNA; baculovirus, yeast plasmids, vectors derived from combinations of plasmids and phage DNA, and viral DNA such as vaccinia, adenovirus, fowl pox virus, and pseudorabies). Large numbers of suitable vectors that are replicable and viable in the host are known to those of skill in the art, and are commercially available. Any other plasmid or vector may be used as long as they are replicable and viable in the host.

In some preferred embodiments of the present invention, bacterial expression vectors comprise an origin of replication, a suitable promoter and optionally an enhancer, and also any necessary ribosome binding sites, polyadenylation sites, transcriptional termination sequences, and 5' flanking nontranscribed sequences. Promoters useful in the present invention include, but are not limited to, retroviral LTRs, SV40 promoter, CMV promoter, RSV promoter, *E. coli* lac or trp promoters, phage lambda $P_L$ and $P_R$ promoters, T3, SP6 and T7 promoters. In other embodiments of the present invention, recombinant expression vectors include origins of replication and selectable markers, (e.g., tetracycline or ampicillin resistance in *E. coli*, or neomycin phosphotransferase gene for selection in eukaryotic cells).

2. Expression of ACHs in Transgenic Plants

Vectors described above can be utilized to express the ACHs of the present invention in transgenic plants. A variety of methods are known for producing transgenic plants.

In some embodiments, Agrobacterium mediated transfection is utilized to create transgenic plants. Since most dicotyledonous plant are natural hosts for Agrobacterium, almost every dicotyledonous plant may be transformed by Agrobacterium in vitro. Although monocotyledonous plants, and in particular, cereals and grasses, are not natural hosts to Agrobacterium, work to transform them using Agrobacterium has also been carried out (Hooykas-Van Slogteren et al., (1984) Nature 311:763–764). Plant genera that may be transformed by Agrobacterium include Arabidopsis, Chrysanthemum, Dianthus, Gerbera, Euphorbia, Pelaronium, Jpomoea, Passiflora, Cyclamen, Malus, Prunus, Rosa, Rubus, Populus, Santalum, Allium, Lilium, Narcissus, Ananas, Arachis, Phaseolus and Pisum.

For transformation with Agrobacterium, disarmed Agrobacterium cells are transformed with recombinant Ti plasmids of *Agrobacterium tumefaciens* or Ri plasmids of *Agrobacterium rhizogenes* (such as those described in U.S. Pat. No. 4,940,838, the entire contents of which are herein incorporated by reference). The nucleic acid sequence of interest is then stably integrated into the plant genome by infection with the transformed Agrobacterium strain. For example, heterologous nucleic acid sequences have been introduced into plant tissues using the natural DNA transfer system of *Agrobacterium tumefaciens* and *Agrobacterium rhizogenes* bacteria (for review, see Klee et al., (1987) Ann. Rev. Plant Phys. 38:467–486).

There are three common methods to transform plant cells with Agrobacterium: The first method is by co-cultivation of Agrobacterium with cultured isolated protoplasts. This method requires an established culture system that allows culturing protoplasts and plant regeneration from cultured protoplasts. The second method is by transformation of cells or tissues with Agrobacterium. This method requires (a) that the plant cells or tissues can be transformed by Agrobacterium and (b) that the transformed cells or tissues can be induced to regenerate into whole plants. The third method is by transformation of seeds, apices or meristems with Agrobacterium. This method requires micropropagation.

One of skill in the art knows that the efficiency of transformation by Agrobacterium may be enhanced by using a number of methods known in the art. For example, the inclusion of a natural wound response molecule such as acetosyringone (AS) to the Agrobacterium culture has been shown to enhance transformation efficiency with *Agrobacterium tumefaciens* (Shahla et al., (1987) Plant Molec. Biol. 8:291–298). Alternatively, transformation efficiency may be enhanced by wounding the target tissue to be transformed. Wounding of plant tissue may be achieved, for example, by punching, maceration, bombardment with microprojectiles, etc. (See e.g., Bidney et al., (1992) Plant Molec. Biol. 18:301–313).

In still further embodiments, the plant cells are transfected with vectors via particle bombardment (i.e., with a gene gun). Particle mediated gene transfer methods are known in the art, are commercially available, and include, but are not limited to, the gas driven gene delivery instrument described in McCabe, U.S. Pat. No. 5,584,807, the entire contents of which are herein incorporated by reference. This method involves coating the nucleic acid sequence of interest onto heavy metal particles, and accelerating the coated particles under the pressure of compressed gas for delivery to the target tissue.

Other particle bombardment methods are also available for the introduction of heterologous nucleic acid sequences into plant cells. Generally, these methods involve depositing the nucleic acid sequence of interest upon the surface of small, dense particles of a material such as gold, platinum, or tungsten. The coated particles are themselves then coated onto either a rigid surface, such as a metal plate, or onto a carrier sheet made of a fragile material such as mylar. The coated sheet is then accelerated toward the target biological tissue. The use of the flat sheet generates a uniform spread of accelerated particles which maximizes the number of cells receiving particles under uniform conditions, resulting in the introduction of the nucleic acid sample into the target tissue.

Plants, plant cells and tissues transformed with a heterologous nucleic acid sequence of interest are readily detected using methods known in the art including, but not limited to, restriction mapping of the genomic DNA, PCR-analysis, DNA—DNA hybridization, DNA-RNA hybridization, DNA sequence analysis and the like.

Additionally, selection of transformed plant cells may be accomplished using a selection marker gene. It is preferred, though not necessary, that a selection marker gene be used to select transformed plant cells. A selection marker gene may confer positive or negative selection.

A positive selection marker gene may be used in constructs for random integration and site-directed integration. Positive selection marker genes include antibiotic resistance genes, and herbicide resistance genes and the like. In one embodiment, the positive selection marker gene is the NPTII gene which confers resistance to geneticin (G418) or kanamycin. In another embodiment the positive selection marker gene is the HPT gene which confers resistance to hygromycin. The choice of the positive selection marker gene is not critical to the invention as long as it encodes a functional polypeptide product. Positive selection genes known in the art include, but are not limited to, the ALS gene (chlorsulphuron resistance), and the DHFR-gene (methothrexate resistance).

A negative selection marker gene may also be included in the constructs. The use of one or more negative selection marker genes in combination with a positive selection marker gene is preferred in constructs used for homologous recombination. Negative selection marker genes are generally placed outside the regions involved in the homologous recombination event. The negative selection marker gene serves to provide a disadvantage (preferably lethality) to cells that have integrated these genes into their genome in an expressible manner. Cells in which the targeting vectors for homologous recombination are randomly integrated in the genome will be harmed or killed due to the presence of the negative selection marker gene. Where a positive selection marker gene is included in the construct, only those cells having the positive selection marker gene integrated in their genome will survive.

The choice of the negative selection marker gene is not critical to the invention as long as it encodes a functional polypeptide in the transformed plant cell. The negative selection gene may for instance be chosen from the aux-2 gene from the Ti-plasmid of Agrobacterium, the tk-gene from SV40, cytochrome P450 from *Streptomyces griseolus*, the Adh-gene from Maize or Arabidopsis, etc. Any gene encoding an enzyme capable of converting a substance which is otherwise harmless to plant cells into a substance which is harmful to plant cells may be used.

It is contemplated that the ACH polynucleotides of the present invention may be utilized to either increase or decrease the level of ACH mRNA and/or protein in transfected cells as compared to the levels in wild-type cells. Accordingly, in some embodiments, expression in plants by the methods described above leads to the overexpression of ACH in transgenic plants, plant tissues, or plant cells. The present invention is not limited to any particular mechanism. Indeed, an understanding of a mechanism is not required to practice the present invention. However, it is contemplated that overexpression of the ACH polynucleotides of the present invention will overcome limitations in the accumulation of fatty acids in oilseeds.

In other embodiments of the present invention, the ACH polynucleotides are utilized to decrease the level of ACH protein or mRNA in transgenic plants, plant tissues, or plant cells as compared to wild-type plants, plant tissues, or plant cells. One method of reducing ACH expression utilizes expression of antisense transcripts. Antisense RNA has been used to inhibit plant target genes in a tissue-specific manner (e.g., van der Krol et al. (1988) Biotechniques 6:958–976). Antisense inhibition has been shown using the entire cDNA sequence as well as a partial cDNA sequence (e.g., Sheehy et al. (1988) Proc. Natl. Acad. Sci. USA 85:8805–8809; Cannon et al., (1990) Plant Mol. Biol. 15:39–47). There is also evidence that 3' non-coding sequence fragment and 5' coding sequence fragments, containing as few as 41 basepairs of a 1.87 kb cDNA, can play important roles in antisense inhibition (Ch'ng et al., (1989) Proc. Natl. Acad. Sci. USA 86:10006–10010).

Another method of reducing ACH expression utilizes the phenomenon of cosuppression or gene silencing (See e.g., U.S. Pat. No. 6,063,947, incorporated herein by reference). The phenomenon of cosuppression has also been used to inhibit plant target genes in a tissue-specific manner. Cosuppression of an endogenous gene using a full-length cDNA sequence as well as a partial cDNA sequence (730 bp of a 1770 bp cDNA) are known (e.g., Napoli et al. (1990) Plant Cell 2:279–289; van der Krol et al. (1990) Plant Cell 2:291–299; Smith et al. (1990) Mol. Gen. Genetics 224:477–481).

3. Other Host Cells and Systems for Production of ACHs

The present invention also contemplates that the vectors described above can be utilized to express plant ACH genes and variants in prokaryotic and eukaryotic cells. In some embodiments of the present invention, the host cell can be a prokaryotic cell (e.g., a bacterial cell). Specific examples of host cells include, but are not limited to, *E. coli, Salmonella typhimurium, Bacillus subtilis*, and various species within the genera Pseudomonas, Streptomyces, and Staphylococcus. The constructs in host cells can be used in a conventional manner to produce the gene product encoded by the recombinant sequence. In some embodiments, introduction of the construct into the host cell can be accomplished by any suitable method known in the art (e.g., calcium phosphate transfection, DEAE-Dextran mediated transfection, or electroporation (e.g., Davis et al. (19896) asic *Methods in Molecular Biology*). Alternatively, in some embodiments of the present invention, the polypeptides of the invention can be synthetically produced by conventional peptide synthesizers.

In some embodiments of the present invention, following transformation of a suitable host strain and growth of the host strain to an appropriate cell density, the selected promoter is induced by appropriate means (e.g., temperature shift or chemical induction), and the host cells are cultured for an additional period. In other embodiments of the present invention, the host cells are harvested (e.g., by centrifugation), disrupted by physical or chemical means, and the resulting crude extract retained for further purification. In still other embodiments of the present invention, microbial cells employed in expression of proteins can be disrupted by any convenient method, including freeze-thaw cycling, sonication, mechanical disruption, or use of cell lysing agents.

It is not necessary that a host organism be used for the expression of the nucleic acid constructs of the invention. For example, expression of the protein encoded by a nucleic acid construct may be achieved through the use of a cell-free in vitro transcription/translation system. An example of such a cell-free system is the commercially available TnT™ Coupled Reticulocyte Lysate System (Promega; this cell-free system is described in U.S. Pat. No. 5,324,637, hereby incorporated by reference).

4. Purification of ACHs

The present invention also provides methods for recovering and purifying ACHs from native and recombinant cell cultures including, but not limited to, ammonium sulfate precipitation, anion or cation exchange chromatography, phosphocellulose chromatography, hydrophobic interaction chromatography, affinity chromatography, hydroxylapatite chromatography and lectin chromatography. In other embodiments of the present invention, protein refolding steps can be used as necessary, in completing configuration of the mature protein. In still other embodiments of the present invention, high performance liquid chromatography (HPLC) can be employed as one or more purification steps.

In other embodiments of the present invention, the nucleic acid construct containing DNA encoding the wild-type or a variant ACH further comprises the addition of exogenous sequences (i.e., sequences not encoded by the ACH coding region) to either the 5' or 3' end of the ACH coding region to allow for ease in purification of the resulting polymerase protein (the resulting protein containing such an affinity tag is termed a "fusion protein"). Several commercially available expression vectors are available for attaching affinity tags (e.g., an exogenous sequence) to either the amino or carboxy-termini of a coding region. In general these affinity tags are short stretches of amino acids that do not alter the characteristics of the protein to be expressed (i.e., no change to enzymatic activities results).

For example, the pET expression system (Novagen) utilizes a vector containing the T7 promoter operably linked to a fusion protein with a short stretch of histidine residues at either end of the protein and a host cell that can be induced to express the T7 DNA polymerase (i.e., a DE3 host strain). The production of fusion proteins containing a histidine tract is not limited to the use of a particular expression vector and host strain. Several commercially available expression vectors and host strains can be used to express protein sequences as a fusion protein containing a histidine tract (e.g., the pQE series [pQE-8, 12, 16, 17, 18, 30, 31, 32, 40, 41, 42, 50, 51, 52, 60 and 70] of expression vectors (Qiagen) used with host strains M15[pREP4] [Qiagen] and SG13009 [pREP4] [Qiagen]) can be used to express fusion proteins containing six histidine residues at the amino-terminus of the fusion protein). Additional expression systems which utilize other affinity tags are known to the art.

Once a suitable nucleic acid construct has been made, the ACH may be produced from the construct. The examples below and standard molecular biological teachings known in the art enable one to manipulate the construct by a variety of suitable methods.

5. Deletion Mutants of ACHs

The present invention further provides fragments of ACHs. In some embodiments of the present invention, when expression of a portion of an ACH is desired, it may be necessary to add a start codon (ATG) to the oligonucleotide fragment containing the desired sequence to be expressed. It is well known in the art that a methionine at the N-terminal position can be enzymatically cleaved by the use of the enzyme methionine aminopeptidase (MAP). MAP has been cloned from *E. coli* (Ben-Bassat et al., J. Bacteriol. 169:751–757, 1987) and *S. typhimurium*, and its in vitro activity has been demonstrated on recombinant proteins (Miller et al., PNAS 84:2718–1722, 1990). Therefore, removal of an N-terminal methionine, if desired, can be achieved either in vivo by expressing such recombinant polypeptides in a host producing MAP (e.g., *E. coli* or CM89 or *S. cerevisiae*), or in vitro by use of purified MAP. It is contemplated that ACH deletion mutants will be screened for activity as described above.

6. Use of ACH Nucleic Acids in Directed Evolution

It is contemplated that the ACH nucleic acids (e.g., SEQ ID NOs: 1–4, and 11–12) can be utilized as starting nucleic acids for directed evolution. These techniques can be utilized to develop ACH variants having desirable properties such as increased synthetic activity or altered affinity for a particular fatty acid substrate.

In some embodiments, artificial evolution is performed by random mutagenesis (e.g., by utilizing error-prone PCR to introduce random mutations into a given coding sequence). The critical feature of this method is that the frequency of mutation must be finely tuned. As a general rule, beneficial mutations are rare, while deleterious mutations are common. This is because the combination of a deleterious mutation and a beneficial mutation often results in an inactive enzyme. The ideal number of base substitutions for targeted gene is usually between 1.5 and 5 (Moore and Arnold (1996) Nat. Biotech.: 14, 458–67; Leung et al, (1989) Technique, 1:11–15; Eckert and Kunkel (1991) PCR Methods Appl., 1:17–24; Caldwell and Joyce (1992) PCR Methods Appl., 2:28–33; and Zhao and Arnold (1997) Nuc. Acids. Res., 25:1307–08). After mutagenesis, the resulting clones are selected for desirable activity (e.g., screened for ACH activity as described above). Successive rounds of mutagenesis and selection are often necessary to develop enzymes with desirable properties. It should be noted that only the useful mutations are carried over to the next round of mutagenesis.

In other embodiments of the present invention, the polynucleotides of the present invention are used in gene shuffling or sexual PCR procedures (e.g., Smith (1994) Nature, 370:324–25; U.S. Pat. Nos. 5,837,458; 5,830,721; 5,811, 238; 5,733,731; all of which are herein incorporated by reference). Gene shuffling involves random fragmentation of several mutant DNAs followed by their reassembly by PCR into full length molecules. Examples of various gene shuffling procedures include, but are not limited to, assembly following DNAse treatment, the staggered extension process (STEP), and random priming in vitro recombination. In the DNAse mediated method, DNA segments isolated from a pool of positive mutants are cleaved into random fragments with DNAseI and subjected to multiple rounds of PCR with no added primer. The lengths of random fragments approach that of the uncleaved segment as the PCR cycles proceed, resulting in mutations in present in different clones becoming mixed and accumulating in some of the resulting sequences. Multiple cycles of selection and shuffling have led to the functional enhancement of several enzymes (Stemmer (1994) Nature, 370:398–91; Stemmer (1994) Proc. Natl. Acad. Sci. USA, 91, 10747–51; Crameri et al (1996) Nat. Biotech., 14:315–19; Zhang et al. (1997) Proc. Natl. Acad. Sci. USA, 94:4504–09; and Crameri et al (1997) Nat. Biotech., 15:436–38).

In some embodiments of the combinatorial mutagenesis approach of the present invention, the amino acid sequences for a population of ACH homologs or other related proteins are aligned, preferably to promote the highest homology possible. Such a population of variants can include, for example, ACH homologs from one or more species, or ACH homologs from the same species but which differ due to mutation. Amino acids appearing at each position of the aligned sequences are selected to create a degenerate set of combinatorial sequences.

In a preferred embodiment of the present invention, the combinatorial ACH library is produced by way of a degenerate library of genes encoding a library of polypeptides including at least a portion of potential ACH-protein sequences. For example, a mixture of synthetic oligonucleotides are enzymatically ligated into gene sequences such that the degenerate set of potential ACH sequences are expressible as individual polypeptides, or alternatively, as a set of larger fusion proteins (e.g., for phage display) containing the set of ACH sequences therein.

There are many ways in which the library of potential ACH homologs can be generated from a degenerate oligonucleotide sequence. In some embodiments, chemical synthesis of a degenerate gene sequence is carried out in an automatic DNA synthesizer, and the synthetic genes are ligated into an appropriate gene for expression. The purpose of a degenerate set of genes is to provide, in one mixture, all of the sequences encoding the desired set of potential ACH sequences. The synthesis of degenerate oligonucleotides is well known in the art (e.g., Narang, Tetrahedron 39:39, 1983; Itakura et al., Recombinant DNA, Proc 3rd Cleveland Sympos. Macromol., Walton, ed., Elsevier, Amsterdam, pp 273–289, 1981; Itakura et al., Annu. Rev. Biochem. 53:323, 1984; Itakura et al., Science 198:1056, 1984; and Ike et al., Nucleic Acid Res. 11:477, 1983). Such techniques have been employed in the directed evolution of other proteins (e.g., Scott et al., Science 249:386–390, 1980; Roberts et al., PNAS 89:2429–2433, 1992; Devlin et al., Science 249: 404–406, 1990; Cwirla et al., PNAS 87: 6378–6382, 1990; as well as U.S. Pat. Nos. 5,223,409, 5,198,346, and 5,096,815, each of which is incorporated herein by reference).

A wide range of techniques are known in the art for screening gene products of combinatorial libraries generated by point mutations, and for screening cDNA libraries for gene products having a particular property of interest. Such techniques are generally adaptable for rapid screening of gene libraries generated by the combinatorial mutagenesis of ACH homologs. The most widely used techniques for screening large gene libraries typically comprise cloning the gene library into replicable expression vectors, transforming appropriate cells with the resulting library of vectors, and expressing the combinatorial genes under conditions such that detection of a desired activity facilitates relatively easy isolation of the vector encoding the gene whose product was detected. The illustrative assays described below are amenable to high through-put analysis as necessary to screen large numbers of degenerate sequences created by combinatorial mutagenesis techniques.

In some embodiments of the present invention, the gene library is expressed as a fusion protein on the surface of a viral particle. For example, foreign peptide sequences can be expressed on the surface of infectious phage in the filamentous phage system, thereby conferring two significant benefits. First, since these phage can be applied to affinity matrices at very high concentrations, a large number of phage can be screened at one time. Second, since each infectious phage displays the combinatorial gene product on its surface, if a particular phage is recovered from an affinity matrix in low yield, the phage can be amplified by another round of viral replication. The group of almost identical *E. coli* filamentous phages M13, fd, and fl are most often used in phage display libraries, as either of the phage gIII or gVIII coat proteins can be used to generate fusion proteins without disrupting the ultimate packaging of the viral particle (e.g., WO 90/02909; WO 92/09690; Marks et al, J. Biol. Chem., 267:16007–16010, 1992; Griffths et al., EMBO J., 12:725–734, 1993; Clackson et al., Nature, 352:624–628, 1991; and Barbas et al., PNAS 89:4457–4461, 1992).

In another embodiment of the present invention, the recombinant phage antibody system (e.g., RPAS, Pharmacia Catalog number 27-9400-01) is modified for use in expressing and screening ACH combinatorial libraries. The pCANTAB 5 phagemid of the RPAS kit contains the gene encoding the phage gill coat protein. In some embodiments of the present invention, the ACH combinatorial gene library is cloned into the phagemid adjacent to the gIII signal sequence such that it will be expressed as a gIII fusion protein. In other embodiments of the present invention, the phagemid is used to transform competent *E. coli* TG1 cells after ligation. In still other embodiments of the present invention, transformed cells are subsequently infected with M13KO7 helper phage to rescue the phagemid and its candidate ACH gene insert. The resulting recombinant phage contain phagemid DNA encoding a specific candidate ACH-protein and display one or more copies of the corresponding fusion coat protein. In some embodiments of the present invention, the phage-displayed candidate proteins that are capable of, for example, binding a particular acyl-CoA, are selected or enriched by panning. The bound phage is then isolated, and if the recombinant phage express at least one copy of the wild type gIII coat protein, they will retain their ability to infect *E. coli*. Thus, successive rounds of reinfection of *E. coli* and panning greatly enriches for ACH homologs, which are then screened for further biological activities.

In light of the present disclosure, other forms of mutagenesis generally applicable will be apparent to those skilled in the art in addition to the aforementioned rational mutagenesis based on conserved versus non-conserved residues. For example, ACH homologs can be generated and screened using, for example, alanine scanning mutagenesis, linker scanning mutagenesis, or saturation mutagenesis.

7. Chemical Synthesis of ACH Polypeptides

In an alternate embodiment of the invention, the coding sequence of an ACH is synthesized, whole or in part, using chemical methods well known in the art (e.g., Caruthers et al., Nuc. Acids Res. Symp. Ser., 7:215–233, 1980; Crea and Horn, Nuc. Acids Res., 9:2331, 1980; Matteucci and Caruthers, Tetrahedron Lett., 21:719, 1980; and Chow and Kempe, Nuc. Acids Res., 9:2807–2817, 1981). In other embodiments of the present invention, the protein itself is produced using chemical methods to synthesize either a full-length ACH amino acid sequence or a portion thereof. For example, peptides can be synthesized by solid phase techniques, cleaved from the resin, and purified by preparative high performance liquid chromatography (e.g., Creighton, *Proteins Structures and Molecular Principles*, W H Freeman and Co, New York N.Y., 1983). In other embodiments of the present invention, the composition of the synthetic peptides is confirmed by amino acid analysis or sequencing (e.g., Creighton, supra).

Direct peptide synthesis can be performed using various solid-phase techniques (Roberge et al., Science 269:202–204, 1995) and automated synthesis may be achieved, for example, using ABI 431 A Peptide Synthesizer (Perkin Elmer) in accordance with the instructions provided by the manufacturer. Additionally, the amino acid sequence of ACH or any part thereof, may be altered during direct synthesis and/or combined using chemical methods with other sequences to produce a variant polypeptide.

Experimental

The following examples are provided in order to demonstrate and further illustrate certain preferred embodiments and aspects of the present invention and are not to be construed as limiting the scope thereof.

In the experimental disclosure which follows, the following abbreviations apply: 0° C. (degrees Centigrade); rpm (revolutions per minute); BSA (bovine serum albumin); $H_2O$ (water); HCl (hydrochloric acid); aa (amino acid); bp (base pair); kb (kilobase pair); kD (kilodaltons); gm (grams); $\mu$g (micrograms); mg (milligrams); ng (nanograms); $\mu$l (microliters); ml (milliliters); mm (millimeters); nm (nanometers); $\mu$m (micrometer); M (molar); mM (millimolar); $\mu$M(micromolar); U (units); V (volts); MW (molecular weight); sec (seconds); min(s) (minute/minutes); hr(s) (hour/hours); $MgCl_2$ (magnesium chloride); NaCl (sodium chloride); $OD_{280}$ (optical density at 280 nm); $OD_{600}$ (optical density at 600 nm); PAGE (polyacrylamide gel electrophoresis); PBS (phosphate buffered saline [150 mM NaCl, 10 mM sodium phosphate buffer, pH 7.2]); BCS (biodegradable counting scintillant); PCR (polymerase chain reaction); PEG (polyethylene glycol); PMSF (phenylmethylsulfonyl fluoride); RT-PCR (reverse transcription PCR); SDS (sodium dodecyl sulfate); Tris (tris (hydroxymethyl)aminomethane); w/v (weight to volume); v/v (volume to volume); Amersham (Amersham Life Science, Inc. Arlington Heights, Ill.); ICN (ICN Pharmaceuticals, Inc., Costa Mesa, Calif.); ATCC (American Type Culture Collection, Rockville, Md.); Bio-Rad (BioRad, Richmond, Calif.); GIBCO (Life Technologies, Inc., Gaithersburg, Md.); Invitrogen (Invitrogen Corp., San Diego, Calif.); Promega (Promega Corp., Madison, Wis.); New England Biolabs (New England Biolabs, Inc., Beverly, Mass.); Novagen (Novagen, Inc., Madison, Wis.); Pharmacia (Pharmacia, Inc., Piscataway, N.J.); Sigma (Sigma Chemical Co., St. Louis, Mo.); and Stratagene (Stratagene Cloning Systems, La Jolla, Calif.).

EXAMPLE 1

Primers Used in PCRs

The following Table lists the primers used in the various PCRs conducted during the development of the present invention.

TABLE 1

Primers Used in Amplification of ACH

| Primer Name | Sequence (5' to 3') | SEQ ID NO: | Use |
|---|---|---|---|
| For ACH1 | | | |
| ACH1-3 | GGAAGACATACTATATCTAG | SEQ ID NO:13 | Used to amplify the first partial cDNA for ACH1 |
| ACH1-4 | GTACCTCTCCCTTTCTGTTG | SEQ ID NO:14 | |
| ACH1-Lncol | CATGAACACTGAATCAGTTGTCG | SEQ ID NO:15 | Used to amplify the first full-length cDNA for sticky-end insertion into pET-24d at an NcoI site and an XhoI site |
| ACH1-Sncol | AACACTGAATCAGTTGTCGAG | SEQ ID NO:16 | |
| ACH1-LxhoI | TCGAGGGCTTCATAGCTTGGCC | SEQ ID NO:17 | |
| ACH1-SxhoI | GGGCTTCATAGCTTGGCCCC | SEQ ID NO:18 | |
| ACH1-NdeI 5' | ATCCGGTAAGTACTCATATGAACACTGAATCAG | SEQ ID NO:19 | Used to characterize ACH1 protein by amplifying ACH1 |
| AHC1 Xhis ext 3' | ATCCTATGGCTTCACTCGAGCTTGGCCCCGAAG | SEQ ID NO:20 | cDNA by PCR from existing cDNA clones |
| GSP1-1 | ACCCAAGCAGTACACACATTCAAGTACA | SEQ ID NO:21 | Used to screen T-DNA mutant Arabidopsis populations for |
| GSP1-4 | CGTCGTTAACCTGTAAAATGAACCACTG | SEQ ID NO:22 | ACH1 knock out mutant |
| For ACH2 | | | |
| b1193 | ACCGACCCTCTAAGAGCC | SEQ ID NO:23 | Used to amplify a portion of the ACH2 gene and cDNA; genomic PCR fragment used as a probe to screen a genomic library |
| b1195 | TGATCTTTTTATTCGTCG | SEQ ID NO:24 | |
| ACH2-5P | CGCCATGAACACCGAGTCAG | SEQ ID NO:25 | Used to amplify the first full-length cDNA |
| ACH2-3P | GAGCCATTCAGAGCTTCGACG | SEQ ID NO:26 | |
| ACH2-SXbaIMBP3' | ATCAGAGCTTCGACGTGCC | SEQ ID NO:27 | Used to create sticky-end PCR products for putting ACH2 into pMAL-c2G, a maltose-binding protein fusion expression vector |
| ACH2-LXbaIMBP3' | CTAGATCAGAGCTTCGACGTG | SEQ ID NO:28 | |
| ACH2-SEcoRIMBP5' | CATGAACACCGAGTCAGTTG | SEQ ID NO:29 | |
| ACH2-LEcoRIMBP5' | AATTCATGAACACCGAGTCAG | SEQ ID NO:30 | |
| GSP2-2 | ATTAAGTAGGAGGAAAATCCATCGTGACAG | SEQ ID NO:31 | Used to screen T-DNA mutant Arabidopsis populations for |
| GSP2-3 | CGAGAAGAAATCACAGAATTGCTCAGATTAC | SEQ ID NO:32 | ACH2 knock out mutant |
| For ACH4 | | | |
| ACH4-3 | CCAGGTATGTACCATTCACCTG | SEQ ID NO:33 | Used to amplify the first partial cDNA |
| ACH4-4 | GATATGACGAGCTTCTTCCTCTG | SEQ ID NO:34 | |
| ACH4LecoRi | AATTATGAATTCCCCAAGAC | SEQ ID NO:35 | Used to amplify the sticky-end products for inserting ACH4 into a GFP fusion expression vector |

TABLE 1-continued

Primers Used in Amplification of ACH

| Primer Name | Sequence (5' to 3') | SEQ ID NO: | Use |
|---|---|---|---|
| ACH4sEcoRi | ATGAATTCCCCAAGACCC | SEQ ID NO:36 | |
| ACH4LbamHI | GATCCTGAAGAATTGTGCC | SEQ ID NO:37 | |
| ACH4SBamHI | CTGAAGAATTGTGCCTAC | SEQ ID NO:38 | |
| | | For ACH5 | |
| ACH5LEcoRi | AATTATGAGATCTTCAGCGGG | SEQ ID NO:39 | Used to amplify the sticky-end products for inserting ACH5 into a GFP fusion expression vector |
| ACH5LEcoRI | ATGAGATCTTCAGCGGGA | SEQ ID NO:40 | |
| ACH5LBamHI | GATCAGGCAATGAGATGGG | SEQ ID NO:41 | |
| ACH5SBamHI | AGGCAATGAGATGGGTCTC | SEQ ID NO:42 | |
| ACH5-5P | ATGAGATCTTCAGCGGGAAAG | SEQ ID NO:43 | Amplified first full-length cDNA |
| ACH5-4 | TCAAGGCAATGAGATGGGTC | SEQ ID NO:44 | |
| GSP5-5 | ACTAGGCACTACTTAGGCAGGAATGAAAG | SEQ ID NO:45 | Used to screen T-DNA mutant Arabidopsis populations for ACH5 knock out mutant |
| GSP5-6 | TCTATCACAGAGGGAAAGAATGATCAAAC | SEQ ID NO:46 | |

EXAMPLE 2

Acyl-CoA Thioesterase (ACH) Assay

In this Example, the methods used to determine Acyl-CoA thioesterase activity in vitro are described. Two different assays have been utilized. In one, enzyme activity is determined from the amount of labeled fatty acid released from radiolabeled acyl-CoA. In the other, enzyme activity is determined from the amount of free CoA released from acyl-CoA by detecting the presence of free thiols.
Detection of Labeled Free Fatty Acids In these assays, radiolabeled acyl-CoA is used as a substrate in which the [$^{14}$C] label is on the fatty acid portion of the molecule, and the enzyme activity is measured by the amount of labeled free fatty acid released by the action of the enzyme. Typically, the acyl group is palmitoyl-CoA (16:0 Co-A) or oleoyl-CoA (18:1-CoA). Because the reaction pH must be below 9, as a pH above this level causes base-catalyzed hydrolysis of the substrate, in most experiments the enzyme activity is measured between pH 7 and 9. The reactions are conducted at room temperature. The reaction volume is generally kept from about 32 µl to 100 µl. Although the reaction times may vary, typical incubation times are 10–15 minutes, which is sufficient for even small amounts of protein.

The protein solution to be assayed, which can be purified protein over-expressed in E. coli or unpurified protein in a plant extract or a plant subfraction, such as purified chloroplasts, is brought to the desired volume with buffer (20 mM Tris-HCl, pH 7.2, 200 mM NaCl and 1 mM EDTA). The reaction is initiated by adding the substrate to the solution, typically to a total volume of 32 µl, and the reaction mixture is incubated at room temperature for the desired period of time. The reaction is terminated by adding 100 µl of 90% isopropanol/10% acetic. The free fatty acids are extracted by adding 900 µl hexane to the solution, vortexing thoroughly to mix the solution, and allowing the hexane to separate from the aqueous phase. An 850 µl aliquot of the hexane phase is added to 3 ml BCS, and the amount of radioactivity determined in a scintillation counter.

The level of acyl-CoA thioesterase activity is determined by the amount of radioactivity that is found in the hexane phase. As the enzyme cleaves fatty acyl-CoAs, the free fatty acids that are released become insoluble in the aqueous reaction mixture and move into the hydrophobic hexane phase when it is added. Unhydrolyzed acyl-CoA remains in the aqueous reaction mixture.
Detection of Free Thiols In this assay, the enzyme activity is measured as the amount of free CoA released by the action of the enzyme; free CoA is detected by the presence of free thiols in solution. When the thioester bond linking the Coenzyme A and the fatty acid is cleaved, the free thiol created on the Coenzyme A can be detected in the presence of 5,5'-Dithio-bis-(2nitrobenzoic acid), also called DTNB or Ellman's reagent, by measuring the absorbance at 412 nm. This assay has been commonly used for characterization of acyl-CoA thioesterases from other species.

The following conditions are typically used in this assay:

| Reagent | Amount (µl) | Final concentration | |
|---|---|---|---|
| Acyl-CoA (0.1 mM) | 180 | 20 µM | The substrates used in |
| BSA (1 mg/ml) | 180 | 200 µg/ml | these assays are fatty |
| DTNB (1 mM) | 180 | 200 µM | acyl-CoA molecules |
| Kpi, 50 mM, pH 8.0 | 357 | | which vary from 10- to |
| Enzyme (1 µg/ml) | | | 20-carbon in length |

The acyl-CoA thioesterase activity assays were all done in 1.5 ml disposable cuvettes using an HP Diode Array Spectrophotometer and observing the change in absorbance of the assay mixture at 412 nm. A 'zero' cuvette was first created by adding all of the reagents together except for the enzyme. The spectrophotometer was zeroed using this blank cuvette. For enzymatic assay reactions, all of the reagents except for the enzyme and 100 ul of the buffer were mixed in the cuvette; sufficient buffer and enzyme for 4 assays (400 ul and 12 ul, respectively) were mixed together in a separate tube. Readings were taken from the cuvette without the enzyme at 412 nm and at one second intervals for approximately 10 seconds before 103 ul of the buffer/enzyme mixture was added to the reaction cuvette. Additional readings were then taken at one second intervals for a total of 60 seconds. The specific activity of the enzyme was determined by observing the change in absorbance at 412 nm and using the molar extinction coefficient of DTNB ($1.36 \times 10^4$ $M^{-1}cm^{-1}$). Each assay was repeated three times.

Measuring the enzyme activity of acyl-CoA thioesterase is difficult because the acyl-CoA molecules exhibit substrate inhibition, presumably due to their detergent-like characteristics. The concentration at which the acyl-CoA molecules begin to inhibit the thioesterase activity of acyl-CoA thioesterase is different depending on the chain length and saturation level of the fatty acid moiety. Longer chain-lengths have a greater inhibitory capacity, which drops as double bonds are introduced in the fatty acid portion.

The BSA concentration also has a significant effect on the enzyme activity; these effects vary, depending upon the substrate fatty acid. Therefore, two different conditions were used during these assays. The first set of conditions maintained a constant BSA concentration for every substrate tested (200:g/ml BSA and 20:M substrate). The second set of conditions utilized the optimal BSA concentration for each substrate; the optimal BSA concentrations were determined in an assay as described above, but in one-third the volume, or 300:1. The optimization assays were conducted in a 96-well plate format using a plate reader that measured the change in absorbance of the assay mixture at 412 nm. In these assays, the substrate was kept constant at 20:M acyl-CoA, and the BSA concentration varied to determine the concentration at which the enzyme was most active for each substrate. Once this was determined, the enzyme assays were conducted in the 900:1 format under 'optimal' BSA conditions.

EXAMPLE 3

Cloning and Characterization of ACH1

In this Example, experiments to clone and characterize ACH1 are described.

In the cloning experiments, primers were developed from the genomic sequence to amplify a portion of the full-length cDNA from size-selected cDNA libraries of 1–2 and 2–3 kb were used. These PCRs resulted in products of two different sizes from the different libraries. This suggested that differential splicing of the mRNA for ACH1 occurs. The partial cDNAs were subcloned into pGEM-T-Easy (Promega), a T-overhang vector, using the manufacturer's instructions. These partial cDNAs represented the thioesterase portion of the protein, but the true 5' end, which encodes the additional N-terminal region remained unidentified at this point.

The discovery of an additional predicted open reading frame (ORF) positioned very closely to what had been considered the ACH1 start codon resulted in the identification of the 5' end much further upstream than originally thought. This region had gone unobserved as it bore no resemblance to other known acyl-CoA thioesterases. This extra bit of sequence, which corresponded to two extra exons of coding region, allowed the identification of cDNA clones in the database that encoded the entire ACH1 cDNA. Two clones were identified, one of which was shorter than the other and had an internal nonsense codon. These clones, obtained from the AIMS database, consisted of the ACH1 cDNA sequence in pZL 1, a cloning vector provided by Gibco. The designation of the sequence that corresponds to the full-length sequence is "GSDB:S: 174537|H3694|H36947|15076 Lambda-PRL2 *Arabidopsis thaliana*, cDNA clone 181C20T7, length=633." The designation of the sequence of the shorter clone is "GSDB:S: 174253|H37158|H37158|15287 Lambda-PRL2 *Arabidopsis thaliana*, cDNA clones 184P8T7, length=343." The longer clone was determined to be the true ACH1 cDNA. This cDNA is shown in FIG. 1 (SEQ ID NO:1).

Genefinder was also used in an effort to discover plant acyl-CoA thioesterase genes. However, Genefinder missed some of the splice sites in the gene, so that the true amino acid sequence was initially ambiguous. It remains impossible to determine the entire correct cDNA sequence of a plant acyl-CoA thioesterase gene by searching in any database with other known acyl-CoA thioesterase, as the inventors have discovered that plant acyl-CoA thioesterases possess an additional unique amino terminal sequence. However, it was possible to determine that the two predicted protein regions (as described above) were part of the same protein, after it was observed that they were positioned very closely together and because it is unlikely to have two separate genes positioned so closely together. By searching the Arabidopsis database with one of the regions, it was possible to identify two cDNA sequences that had been deposited. After obtaining these sequences and sequencing them, the true sequence of ACH1 was determined.

ACH1 Cloning and Overexpression

The full-length cDNA (i.e., SEQ ID NO:1) was used as a template to make sticky-ended PCR products, as known in the art (See e.g., Zeng (1998) Biotechnology, 25:206–208), which allows the creation of an insert that has overhanging sticky-ends, without need of using any restriction enzymes. Briefly, this was accomplished by amplifying two separate PCR products that were identical except at the 5' and 3' ends. One PCR product was longer at the 5' end, corresponding to a sticky-end overhang that results when a restriction enzyme of choice cleaves a DNA strand. The other PCR product was similarly longer at the 3' end, corresponding to a sticky-end overhang that would be created by a different restriction enzyme when it cleaves a DNA strand. The two PCR products were mixed together, denatured at high temperature, and then reannealed as the temperature was slowly dropped. Thus, 25% of the reannealed product so formed have the correct 5' and 3' overhangs for cloning into a vector that has been treated with restriction enzymes corresponding to the sticky-end overhangs (See e.g., FIG. 1 of Zeng, supra). After the product was annealed, a vector cut with the appropriate restriction enzymes (New England Biolabs) and treated with calf intestinal phosphatase to prevent self-ligation was added. The reannealed sticky-end PCR product was then ligated into the vector using New England Biolabs T4 DNA ligase and buffer. Subsequently, an aliquot of the mixture (usually 15 μl of the ligation reaction) were used to transform a cloning strain of *E. coli* to produce large amounts the DNA.

In order to characterize ACH1 further, it was desirable to over-express the protein in a host cell; the over-expressed protein could then be analyzed, as by purification and activity assays. To that end, the sticky-ended PCR products were put into pET-24d obtained from Novagen, using New England Biolabs cloning tools (e.g., buffer, ligase, etc.). This was determined to correspond to the native sequence without any additional amino acids. The expression vector (pET-24d/ACH1) was transformed into DH10B (for cloning purposes) and later into BL-21 Gold (Stratagene) (for over-expression). The BL-21 host was used as it provides tight control over "leaky" expression. The expression vector resulted in over-expression of the inserted gene; however, initial attempts to purify the over-expressed protein from this vector, either by itself or with the addition of a tag of six histidines, were unsuccessful. It was subsequently determined that it was necessary to remove a stop codon, and the experiments were repeated as described below.

ACH 1 was then over-expressed as a fusion protein with six histidine tags (ACH1/6His) from a second vector. In order to characterize the ACH1 protein, the ACH1 cDNA was amplified by PCR from existing cDNA clones using the following primers:
ACH1 NdeI 5': ATCCGGTAAGTACTCATATGAACACT-GAATCAG (SEQ ID NO:19) ACH1 Xhis ext 3': ATC-CTATGGCTTCACTCGAGCTTGGCCCCGAAG (SEQ ID NO:20)

The product of this PCR reaction, which contained restriction sites NdeI at the 5' end and Xho I at the 3' end, was cloned into the pET-24c (Invitrogen) vector in-frame with a 6-histidine tag. The stop codon of the cDNA was deleted so that the protein would terminate with a series of six histidines coded by the vector. This vector, designated ACH1-6His/pET-24c was then introduced into BL-21 Gold (DE3) E. coli chemically competent cells (Stratagene) using methods known in the art.

Cells were grown in liquid culture at 37° C. to an optical density at 600 nm of 0.5–0.6, then cooled to room temperature. IPTG was added to a final concentration of 800 uM and the cells were shaken at 300 rpm overnight at room temperature. The cells were then collected by centrifugation and frozen overnight at −20° C. or frozen in liquid nitrogen. After thawing, the cells were resuspended in 1×Binding Buffer (all buffers used in this purification process were made according to instructions in the Novagen His-Bind Kit manual except that the buffers were pH 6.0 and not pH 7.9). The resuspended cells were lysed by sonication and subsequently centrifuged at 20,000×g for 30 min to separate the insoluble and soluble cell fractions.

The soluble ACH1/6His was subsequently purified using Ni2+ affinity column chromatography according to the protocols outlined by Novagen. However, ACH1/6His was not purified using this technique, because the protein appeared to be present only in insoluble inclusion bodies.

The entire expression and purification process was repeated, except that the induced cells were shaken overnight at 4° C. rather than at room temperature. Growing the cells at the lower temperature was an attempt to solve possible folding problems that the over-expressed protein might be experiencing at higher temperatures. However, this attempt at obtaining more soluble protein was also unsuccessful.

Activity of ACH1

The activity of the over-expressed ACH1 protein, which was expressed as a fusion protein with a 6 histidine tag as described above, was assayed for acyl-CoA thioesterase by utilizing radiolabeled acyl-CoA substrates, as described previously. The enzyme source was cell lysate prepared from the transfected cells. However, the activity of the lysate from cells over-expressing ACH1 was no greater than the level of activity in cells transfected with a control plasmid.

Isolation of ACH1 Mutant Arabidopsis

A population of thousands of Arabidopsis lines that carry random genomic T-DNA insertions, housed at the University of Wisconsin, was screened for ACH1 mutants. Using PCR, it is possible to screen through the thousands of plants in order to find a single line that carries a T-DNA insertion in the gene of interest. Primers were constructed that would be appropriate for screening the DNA collection for an ACH1 mutant, in accordance with the recommendations of the Arabidopsis Knockout Facility. The following primer sequences were used for the screening:
GSP1-1: ACCCAAGCAGTACACACATTCAAGTACA (SEQ ID NO:21)
GSP1-4: CGTCGTTAACCTGTAAAATGAACCACTG (SEQ ID NO:22)

These primers were provided to the Knock Out facility at Wisconsin where they were used for screening the ALPHA population of mutants (which are the kanamycin-resistant lines). PCR reactions conducted at Wisconsin were screened by Southern blotting in order to identify pools of DNA that contained DNA from an ACH1 knockout plant. The primary screen indicated that there existed at least two ACH1 T-DNA mutants, one in pool #7 and one in pool #9. This screen involved Southern blotting the PCR reactions sent from Wisconsin, which was performed with a DIG-labeled probe (Boehringer Mannheim) following the manufacturers instructions for probe construction and probing techniques. The template for the probe was the genomic fragment amplified by GSP1-1 and GSP1-4.

The secondary screen involved another round of PCR reactions, run at Wisconsin with DNA subpools of the primary pools. This revealed that the mutant in pool #7 was in subpool #57, and the mutant in pool #9 was in subpool #81. Seed pools for these two subpools were ordered from the Arabidopsis Biological Resource Center. Following the protocols designed by the Knockout Facility, these seed pools were screened by PCR. A mutant was eventually identified in seed pool 2003 of the subpool #81. The T-DNA insertion is located at bp 1746 of the ACH1 gene in the $9^{th}$ exon. The other mutation in subpool #57, in which the T-DNA is inserted at bp 813 in the $5^{th}$ exon; the seed pool has not yet been identified.

The mutant plants are then grown, and the plants evaluated for the effect of the mutation on the plant. The effect of the mutation is assessed in germinating seedlings, in growing and mature plants, and in flower and seed development. The assessment includes evaluation of phenotypic appearance, growth rate (as determined by parameters such as dry matter accumulation), time to reach different developmental stages, seed set and viability, and biochemical analyses which include lipid and fatty acid analysis of various plant tissues. Since there appears to be a second ACH homolog in the putative peroxisomal class of ACHs, it is anticipated that ACH1 mutants will not be significantly different from wild-type plants if the two genes in this class serve the same function. However, it is anticipated that these mutants can be crossed with a plant carrying a T-DNA insertion in the ACH2 gene, thus completely removing the activity of the enzymes of this class. This will be useful for further evaluating the function of these genes in vivo. Any effects of this mutant may be ascribed to the function of the ACH1.

EXAMPLE 4

Cloning and Characterization of ACH2

In this Example, experiments to clone and characterize ACH2 are described.

Cloning

Searching the Arabidopsis database with a homologous protein (e.g., E. coli TesB or human HIV-1 Nef-associated thioesterase) revealed a small portion of the A CH2 cDNA. Two sequences were identified in the Arabidopsis database that showed high homology with acyl-CoA thioesterase from other organisms. ACH2 was identified as one of these sequences. This sequence was designated as "GSDB:S:3285641|T04836|T04836|884 AT-NHC *Arabidopsis thaliana* cDNA clone B119XP, length=478." The alignment of *E. coli* TesB (228 to 283) (SEQ ID NO:9) and the putative ACH2 sequence (81 to 248) (SEQ ID NO:10) is shown below.

contained a 1 bp mistake. It is contemplated that these small mistakes will find use, in that they provide different sequences from the native cDNA, but would result in only small changes at the protein level. Based on these sequencing results, the pGEM-T/ACH2(rosette) vector was used to

```
                Alignment of E. coli TesB and Putative ACH2 Sequence

TesB  TIDHSMWFHRPFNLNEWLLYSVESTSASSARGFVRGEFYTQDGVLVASTVQEGVMR (SEQ ID NO:9)

++DH+MWF P +EWLLY+S+A RGFV G+++G L V S QE++R

ACH2  SLDHAMWFTDPLRADEWLLYVIVSPTAHETRGFVTGQMFNRKGELVVSLTQEALLR (SEQ ID NO:10)
```

Initially, this was the only cDNA sequence available, although there was also a genomic clone that contained all but one end of the complete gene. However, the presence of this genomic clone was initially unrecognized, because of poor quality sequencing data that had been submitted for the clone (F21N11-Sp6 IGF *Arabidopsis thaliana* genomic clone F32N11, genomic survey sequence). The cDNA clone that was in the database turned out to be only the last 250 bp of the ACH2 cDNA. Using this sequence, primers were produced to amplify a 500 bp genomic fragment which was then used to screen an Arabidopsis genomic library for the ACH2 gene. A screen conducted using X1-1 Blue MRA P2 cells (Stratagene), according to the manufacturer's instructions, resulted in the isolation of a lambda FIX clone that carried the ACH2 gene.

This gene was sequenced by starting at the known region and walking toward the 5' end using methods known in the art. Sequencing was considered to be complete when all of the sequence had been identified which was homologous to ACH1. By comparing the ACH1 cDNA sequence to the ACH2 genomic sequence, the exons of the ACH2 gene were predicted. Primers for the predicted 5' and 3' ends of the cDNA were developed in order to amplify a full-length cDNA from Arabidopsis total RNA using Superscript One-Step RT-PCR System (Gibco). Using poly-A RNA prepared from various tissues, full-length cDNAs were successfully amplified. Full-length cDNA amplified from leaf poly-A RNA was then ligated into pGEM-T Easy and the vector was used to transform DH10B *E. coli* cells, using methods known in the art.

After sequencing the ACH2 cDNA amplified from leaf poly-A RNA, it was determined that there was a 1 bp difference between that sequence and the genomic DNA. As the genomic sequence was viewed as being more accurate, the root cDNA was subcloned into pGEM-T Easy and the vector used to transform DH10B cells, in order to determine whether it contained the correct sequence. Sequencing of this product indicated that it contained errors as well, although they were different from the errors observed in the leaf cDNA. This indicated that the Superscript Reverse Transcriptase used to amplify the cDNA from the poly-A RNA was possibly faulty (i.e., by putting random errors throughout the PCR product).

The remaining ACH2 cDNAs from various tissues (dry seed, rosette leaves, total aerial, and silique tissues) were subcloned into pGEM T-Easy. Instead of transforming all of these pGEM-T Easy/ACH2 ligations into DH10B cells, these cDNAs were directly sequenced. Sequencing indicated that the cDNA amplified from the rosette leaf poly-A RNA had the correct sequence (SEQ ID NO:2) when compared to the ACH2 genomic sequence. The total aerial ACH2 cDNA transform DH10B cells. After the clones were sequenced, it was determined that there was a 4 bp insertion introduced into the cDNA sequenced. This insertion was not present when the PCR products were directly sequenced, but appeared following subcloning into the vector. This puzzling development indicated that the correct ACH2 cDNA sequence remained to be identified and cloned.

To create sticky-end products for subcloning ACH2 into pET-24d with a 6-His tag in frame, the cDNA amplified from the rosette leaf poly-A RNA was used as a template. DH10B cells were transformed with the resultant plasmid. One clone was identified with a single bp change that caused no change at the amino acid level.

ACH2 was over-expressed as two fusion proteins: a fusion with a maltose-binding protein (MBP) in *E. coli* (ACH2/MBP) and as a fusion protein with six histidine residues (ACH2/6His), as described below. Both proteins were then assayed for acyl-CoA activity, also as described below.

Overexpression and Purification of ACH2/MBP

The ACH2-6HIS/pET-24d plasmid (as described below) was used as a template to create sticky-end products and introduce ACH2 into pMAL-c2G (New England Biolabs) (i.e., a maltose-binding protein expression vector). This vector was introduced into XL-1 Blue cells (Stratagene) and then into BL-21 Gold (DE3) cells. Because the host cells may contain endogenous acyl-CoA thioesterase activity, *E. coli* cells expressing only the MBP were used as a control for purification and characterization of the exogenous Arabidopsis ACH2. The cells were lysed and the soluble portion was separated from the insoluble portion by centrifugation. The ACH2-MBP fusion protein and the MBP protein were then purified by passing the soluble extracts over amylose columns. Amylose binds MBP, while contaminating proteins pass through the column. Both ACH2-MBP and MBP were purified to nearly 90% purity in this way.

Overexpression and Purification of ACH2/6His

The stop codon of the ACH2 coding region was removed so that it could be cloned into the pET-24d plasmid in-frame with a string of six histidine residues. The string of histidines allows for subsequent purification of ACH2 using Ni2+ affinity chromatography.

The pET-24d plasmid (Novagen) containing the ACH2 coding region was introduced into chemically competent B1-21 GOLD (DE3) *E. coli* cells (Stratagene) using techniques known in the art.

The cells were grown in LB Medium until they reached an optical density between 0.5–0.6. They were then cooled to room temperature, and protein over-expression initiated by adding IPTG to a final concentration of 800:M. The cells were grown overnight at room temperature, shaking at 300 rpm. The cells were then collected by centrifuged, and either frozen slowly overnight at −20° C. or frozen instantly with liquid nitrogen. The frozen cells were resuspended in 1×Binding Buffer (all buffers used in this purification process were made according to instructions in the Novagen His-Bind Kit manual except that the buffers were made at pH 6.0 and not 7.9). The resuspended cells were lysed by sonication and subsequently centrifuged at 20,000×g for 30 min to separate the insoluble and soluble cell fractions.

The soluble ACH2/6His was subsequently purified using Ni2+ affinity column chromatography according to the protocols outlined by Novagen. This protocol allowed for nearly complete purification of the ACH2/6His protein from other *E. coli* proteins.

Activity of ACH2

ACH2 was over-expressed as two fusion proteins: a fusion with a maltose-binding protein (MBP) in *E. coli* (ACH2/MBP), and a fusion protein with six histidine residues (ACH2/6His). Both proteins were assayed for acyl-CoA activity.

Both ACH2/MBP and MBP were over-expressed and purified as described above. The purified MBP control was important because although the MBP has no inherent acyl-CoA thioesterase activity, some *E. coli* thioesterases may contaminate both purified proteins. Assaying the purified MBP protein for acyl-CoA thioesterase activity was conducted in order to determine how much of the total activity was due to contaminating *E. coli* proteins. This "background" activity was then subtracted from the total acyl-CoA thioesterase activity of the ACH2-MBP purified protein in order to determine how much activity is due solely to ACH2-MBP.

The purified protein samples were assayed for acyl-CoA thioesterase activity essentially as described above with radiolabeled acyl-CoA as a substrate; 0.5 μg of total protein (determined using the Bradford assay, as known in the art) were incubated with either radiolabeled 16:0-CoA or radiolabeled 18:0 Co-A. The reaction mixture included buffer containing 20 mM Tris-HCl, pH 7.2, 200 mM NaCl, and 1 mM EDTA in a total volume of 32 μl; there were also trace amounts of maltose, which was used to elute the proteins off of the amylose column. The assays were incubated at room temperature for 25 minutes, then stopped by the addition of 100 μl of 90% isopropanol/10% acetic acid. 900 μl of hexane were added, and the mixture vortexed and then briefly centrifuged to separate the hexane phase from the aqueous phase. An 800 μl aliquot was removed from the hexane phase and added to 3 ml BCS, and the amount of radioactivity determined in a scintillation counter.

The results, as shown in FIG. 7, indicate that purified ACH2-MBP was 39 times more active than the purified MBP with 16:0 CoA as the substrate, and 37.2 times more active with 18:0 CoA as the substrate. Thus, these results demonstrate that ACH2-MBP functions as an acyl-CoA thioesterase.

ACH2/6His was over-expressed and purified as described above, and then assayed for acyl-CoA activity by measuring the amount of free CoA released, essentially as described previously. The enzyme activity was measured with both standard BSA concentrations, and with optimal BSA concentrations for different substrates. The optimal BSA concentrations are as follows:

| Substrate | Optimal BSA Concentration (μg/ml) |
|---|---|
| 10:0-CoA | 0 |
| 12:0-CoA | 0 |
| 14:0-CoA | 60 |
| 16:0-CoA | 170 |
| 16:1-CoA | 100 |
| 18:0-CoA | 320 |
| 18:1-CoA | 250 |
| 18:2-CoA | 120 |

Figure 8A:
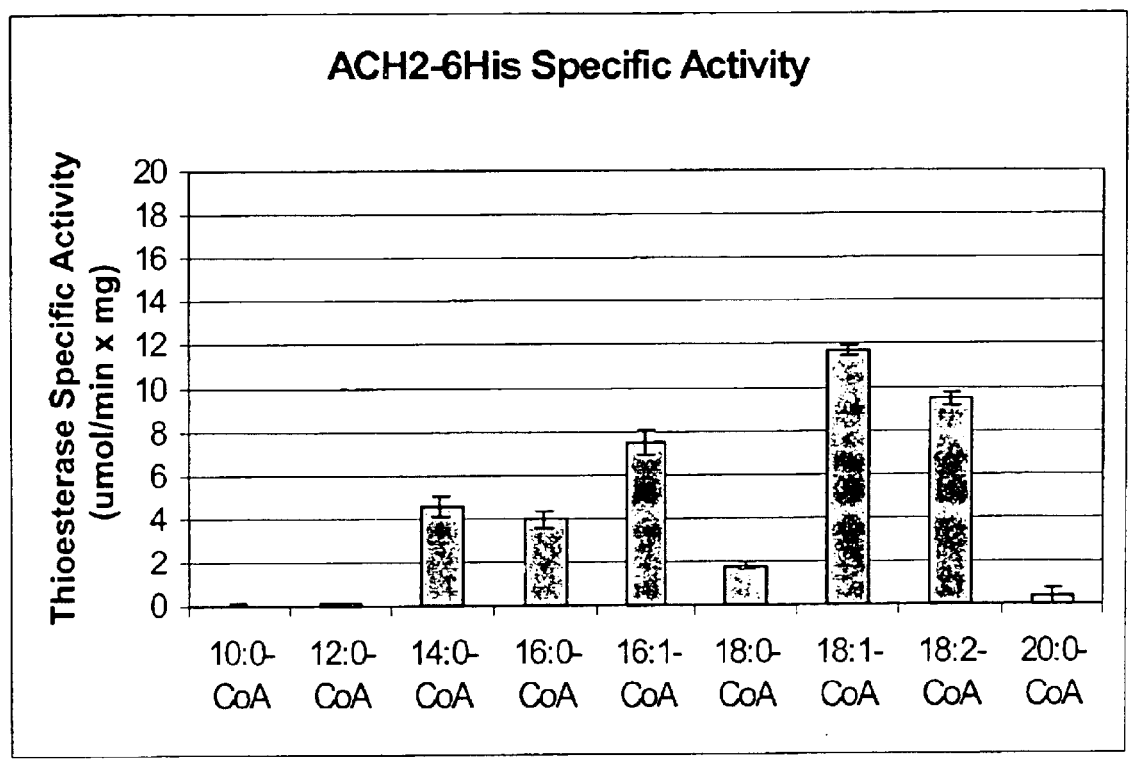
FIG. 8 shows a histogram of the activity of ACH2/6 His; panel A shows the activity in the presence of a constant amount of BSA, and panel B shows the activity in the presence of optimal concentrations of BA for each substrate.
Figure 8B:
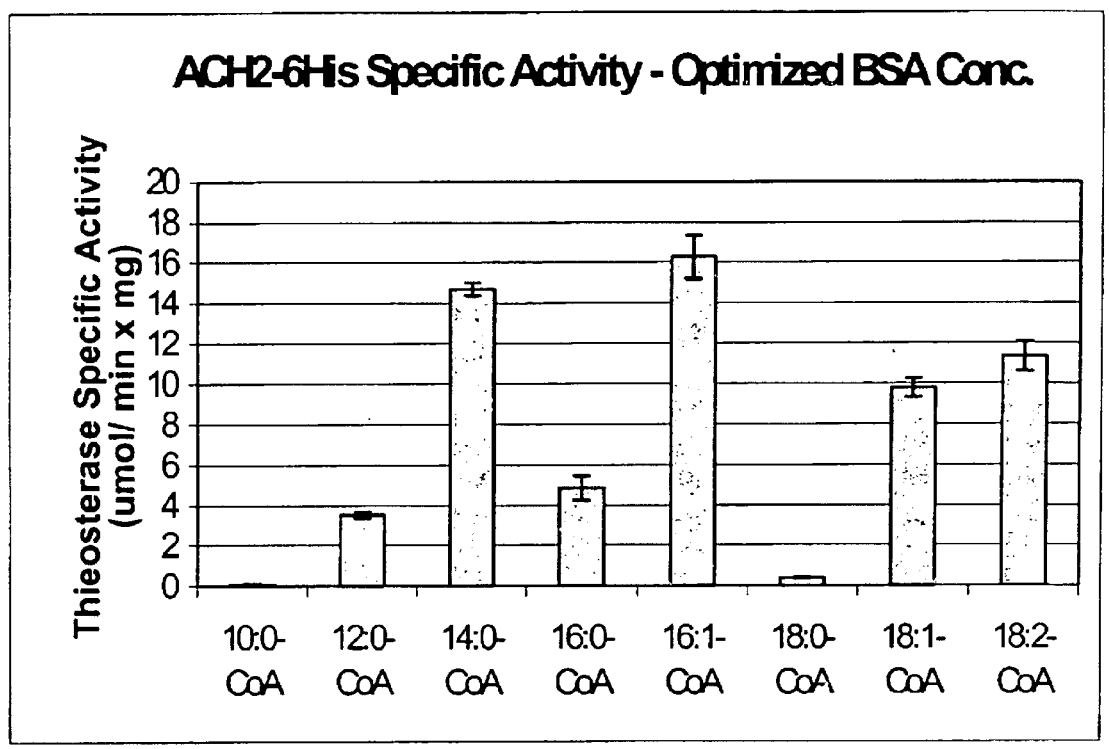

The results of the enzyme assays are shown in FIG. 8. In FIG. 8A, the enzyme assays were conducted with 20 μM acyl-CoA substrate, and 200 μg/ml BSA; in FIG. 8B, the enzyme assays were conducted with 20 μM acyl-CoA substrate and an optimized BSA substrate, as indicated above. The results demonstrate that ACH2/6His possesses acyl Coenzyme A thioesterase activity with acyl-CoA substrates with different chain-lengths. The observed enzyme activity is dependent upon the concentration of BSA present in the assay mixture. When the BSA level is held constant at 200 ug/ml, ACH2/6His exhibits a specificity for longer-chain acyl-CoAs, with 18:1-CoA as the best substrate (see FIG. 8A). When an optimal concentration of BSA is added for each substrate, the preference of the enzyme shifts toward smaller chain-lengths of acyl-CoAs, with 14:0-CoA and 16:1-CoA as the best substrates (see FIG. 8B). The activity of ACH2/6His with the substrate is 20:0-CoA could not be determined, because the optimal BSA concentration is so high that it binders the assays.

Isolation of ACH2 Arabidopsis Mutant

A population of thousands of Arabidopsis lines that carry random genomic T-DNA insertions, housed at the University of Wisconsin, was screened for ACH2 mutants. Using PCR, it is possible to screen through the thousands of plants in order to find a single line that carries a T-DNA insertion in the gene of interest. Primers were constructed that would be appropriate for screening the DNA collection for an ACH2 mutant, in accordance with the recommendations of the Arabidopsis Knockout Facility. The following primer sequences were used for the screening:

GSP2-2: ATTAAGTAGGAGGAAAATCCATCGTGACAG (SEQ ID NO: 31)

GSP2-3: CGAGAAGAAATCACAGAATTGCTCAGAT-TAC (SEQ ID NO: 32)

These primers were provided to the Knock Out facility at Wisconsin, where they were used for screening. PCR reactions that were run at Wisconsin were screened by Southern blotting in order to identify pools of DNA that contained DNA from an ACH2 knockout plant. The preliminary screen showed at least two possible ACH2 T-DNA mutants existed in their BASTA-resistant mutant population. These were in pool #3 and pool #11. The #3 mutant was found using the GSP2-3 primer, while the #11 mutant was identified using the GSP2-2 primer.

The secondary screen was less definite. This secondary screen narrows down the number of plants that could be the ACH2 mutant to only 10 plants, but the PCR results were inconclusive for both candidates. Southern blotting and PCR reamplification of PCR products finally identified the seed pool of 10 in which the mutant in pool #3 resides. This seed pool is designated Plate 20, Row F, Column 9 by the Arabidopsis Knock Out Facility. This seed was planted and the individual ACH2 mutant plant was identified. The T-DNA insertion is at bp 1251 (counting from the start codon) and is situated in the intron between the $8^{th}$ and $9^{th}$ exon. This should give complete inhibition of gene expression.

The T-DNA mutant in pool #11 was also difficult to narrow down to the pool of 10 plants. The Knockout Facility at Wisconsin repeated the PCR screen three times before it was possible to identify the seed pool of 10. The seed pool that was identified is designated Plate 20, Row F, Column 9 by the Knockout Facility. The seeds were sown immediately upon receipt. However, further screening has failed to identify an individual plant that has the T-DNA insertion. This mutant has the T-DNA insertion at bp 2498 (counting from the start codon) in the intron between the $14^{th}$ and $15^{th}$ exon. This should also give complete inhibition of gene expression.

The mutant plants are then grown, and the plants evaluated for the effect of the mutation on the plant. The effect of the mutation is assessed in germinating seedlings, in growing and mature plants, and in flower and seed development. The assessment includes evaluation of phenotypic appearance, growth rate (as determined by parameters such as dry matter accumulation), time to reach different developmental stages, seed set and viability, and biochemical analyses which include lipid and fatty acid analysis of various plant tissues. Since there appears to be a second Acyl-CoA homolog in the putative peroxisomal class of ACHs, it is anticipated that the mutants will not be significantly different from wild-type plants if the two genes in this class serve the same function. However, it is anticipated that these mutants can be transfected with antisense ACH1 and thus useful in further evaluating the function of these genes in vivo, in a manner similar to that described below in Example 5. Any effects of the mutant may be ascribed to the function of the ACH2.

EXAMPLE 5

Cloning and Characterization of ACH4 and ACH5

In this Example, cloning and characterization of ACH4 and ACH5 are described. Initially, the amino acid sequence of a new mouse acyl-CoA thioesterase (Poupon et al. (1999) J. Biol. Chem., 274:19188–19194) was used to BLAST the Arabidopsis database. This resulted in two matches, both of which were large genomic clones. The database predicted a protein for one of the genes, which was eventually demonstrated to be very close to the real ACH5 sequence. No protein was predicted for the other gene, which was tentatively referred to as "ACH4."

ACH4
Cloning

As with ACH5, ACH4 was identified by its homology to mouse thioesterase. The gene was in the Arabidopsis database as a large genomic clone. Initially, the putative sequence of the ACH5 cDNA was compared to the ACH4 gene in order to predict the positions of the open reading frames. However, ACH4 and ACH5 lost their homology towards the end of the genes, which left the real 5' end of ACH4 in doubt. The sequence of the putative ACH4 sequence was designated "GSDB:S:4681120|AP000372|AP000372|*Arabidopsis thaliana* genomic DNA, chromosome 5, TAC clone: K23F3, length 36,824."

Subsequently, a 1.1 kb fragment of cDNA was amplified using total aerial poly-A RNA as a template in RT-PCR, using the Superscript One-Step RT-PCR System (Gibco). These reactions were then reamplified by traditional PCR to obtain a visible product. No further cDNA sequence could be determined despite various attempts at RT-PCR with primers based on genomic sequence.

The ACH4 cDNA present in pSPORT1 (Genome Systems) was sequenced. This clone was designated as "GSDB:S:4959535|A1999441|A1999441|701555896| *Arabidopsis thaliana*, Columbia Co-0, rosette-3 *Arabidopsis thaliana* cDNA clone 701555896, mRNA sequence, length= 449." The ACH4 cDNA in pSPORT1 was then used as a template for amplifying an insert and subcloning ACH4 into pET-24d. The resultant vector was then introduced into DH10B cells. It is further contemplated that binary vectors will find use in transforming plant tissue.

ACH4-Antisense Expression in ACH5 T-DNA Mutant Background

In order to determine the function of both ACH4 and ACH5, an antisense expression vector was created for ACH4 which could be used to transform ACH5 T-DNA mutants (described below). ACH4 and ACH5 represent the two members the second class of acyl-CoA thioesterases of the present invention, and are putatively localized to the mitochondria, where they are thought to be involved in lipid synthesis. There appear to be no other members of this class in Arabidopsis. Therefore, expressing the ACH4 antisense construct in an ACH5 T-DNA mutant would give a complete knockout of this class of enzymes under optimal conditions. Since antisense expression often has variable effectiveness, any phenotype resulting from the experiment will most likely have varying effects, from minimal to severe, and thus shed light on the role of the enzymes in the plant.

The ACH4 cDNA was removed from the pET-24d vector by restriction digest and introduced into a binary vector. The antisense orientation of the cDNA in relation to the promoter in was confirmed by PCR. The promoter, antisense cDNA, and terminator were then placed into a plant transformation plasmid that can be transferred from Agrobacterium and stably integrated into the plant genome. The plasmid also carries a BASTA resistance marker and the T-DNA flanking regions for effective T-DNA transfer and insertion.

The ACH4-antisense plasmid was then introduced into an Agrobacterium strain, which was grown overnight, collected by centrifugation, and used to transform ach5 mutant Arabidopsis plants by floral dip method. The floral dip method involves inverting the plants to dip them into the Agrobacterium/dipping media solution for about 10 seconds. The plants were then grown to maturity and the seed harvested. Seeds from the transformed plant were sown in BASTA-containing soil, and seedlings that survived the BASTA treatment were transferred to regular soil after two weeks. The plants are grown to maturity, and the effect of the antisense expression is assessed in germinating seedlings, growing and mature plants, and in flower and seed development. The assessment includes evaluation of phenotypic appearance, growth rate (as determined by parameters such as dry matter accumulation), time to reach different developmental stages, seed set and viability, and biochemical analyses which include lipid and fatty acid analysis of various plant tissues. It is anticipated that the antisense construct will have varying and detrimental effects upon the plant.

Isolation of ACH4 Arabidopsis Mutant

In addition to the antisense-expression studies, a T-DNA mutant from the BASTA population of T-DNA mutants at the Arabidopsis Knockout Facility at the University of Wisconsin is identified and isolated, in a manner similar to that described for ACH1 and ACH2.

ACH5

Cloning

A genomic clone was identified in the Arabidopsis database which contained the ACH5 gene sequence. The database reference is "GSDB:S:1634607|AC002340|AC002340|*Arabidopsis thaliana* chromosome II section 173 of 225 of the complete sequence. Sequence from clones T6B20, T11J7, length=79676." Genefinder predicted a gene and protein product in this region. Using primers based on the predicted cDNA (Genefinder), the Superscript One-Step RT-PCR System (Gibco) was used to amplify what was believed to be full-length cDNA for ACH5.

The amplified cDNA was subcloned into pPCR-Script AMP (Stratagene), a blunt-end cloning vector. The sequencing of full-length cDNA was then completed. The sequence was found to code for a protein that is nearly identical to the one predicted by Genefinder, with the exception of a small region towards the N-terminus. The ACH5 cDNA was then subcloned into pET-24d in order to add a 6-His tag. The resultant plasmid was then introduced into DH10B cells and BL-21 Gold (DE3) cells. In addition, the vector was also placed into C41 and C43 cells, which are *E. coli* strains that are proficient at expressing typically insoluble proteins in soluble form.

Activity of ACH5

ACH5-6His was over-expressed in *E. coli* using the pET24d expression vector as discussed above and known in the art, and the activity measured by using radiolabeled acyl-CoA substrates, essentially as described previously.

The cells in which ACH5-6His was over-expressed were lysed and the soluble fraction separated from the insoluble fraction by centrifugation. As a control, soluble extract from *E. coli* cells carrying only an empty pET24d vector was collected in the same way. The acyl-CoA thioesterase activity of the soluble extract of the ACH5-6His producing cells was then compared with that of the empty vector soluble extract.

Acyl-CoA thioesterase activity was determined by incubating 0.1 μg of soluble protein (determined using the Bradford assay, as known in the art) incubated with radiolabeled 16:0 CoA. The reaction volume was kept at 32 μl in buffer containing 20 mM Tris-HCl, pH 7.2, 200 mM NaCl, and 1 mM EDTA. The reaction mixture was incubated at room temperature for 25 minutes, then terminated with 100 μl of 90% isopropanol/10% acetic acid. 900 μl of hexane were added, and the mixture vortexed and briefly centrifuged to separate the hexane from the aqueous phase. An 800 μl aliquot of the hexane phase was removed and added to 3 ml BCS. The relative activity of the purified pET24d/ACH5-6His and pET24d soluble extracts was determined by counting the radioactivity in the BCS on a scintillation counter.

Figure 9:
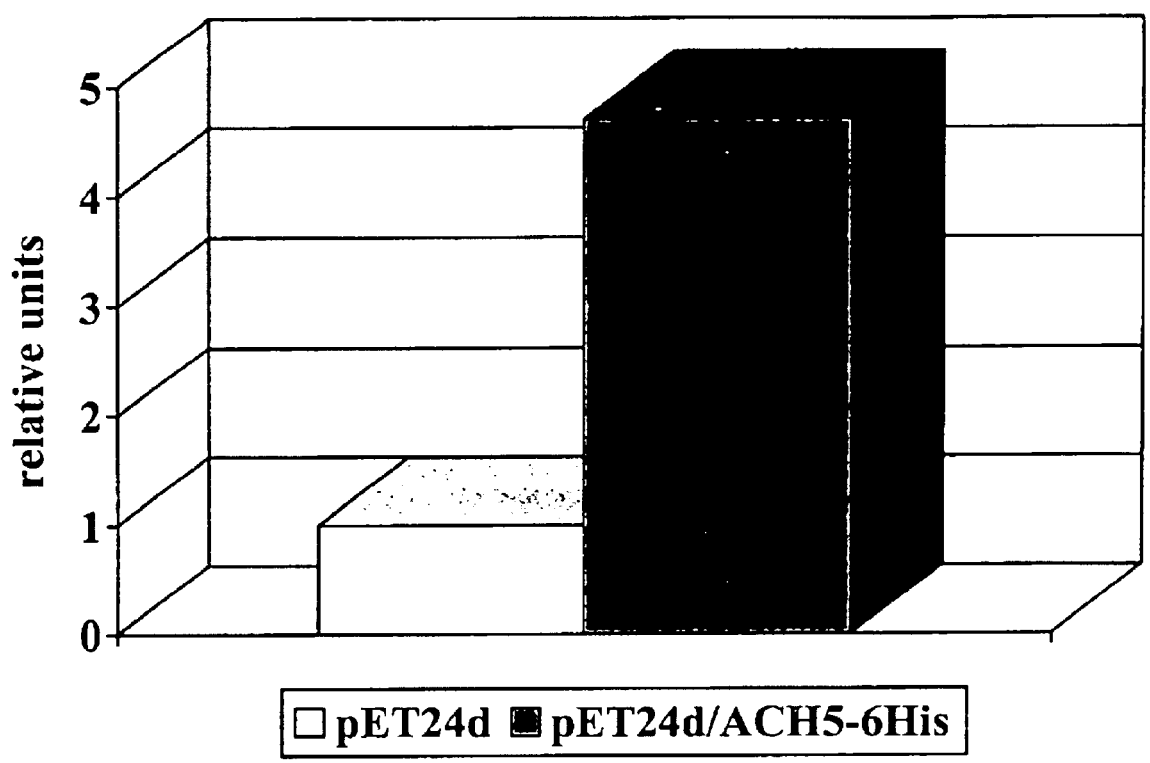
FIG. 9 shows a histogram showing the activity of lysates from cells transformed with either pET24d/ACH5-6His or pT24d.

The results, as shown in FIG. 9, indicate that the pET24d/ACH5-6His soluble extract was 4.7 times more active than the extract from cells containing empty pET24d vector.

These results demonstrate that ACH5-6His functions as an acyl-CoA thioesterase.

Localization of ACH5

The ACH5-His/pET-24d vector is also used as a template to create an insert for subcloning ACH5 into a green fluorescent protein expression. This vector is transfected into DH10B cells. The fusion protein expression product is then localized ultimately in the mitochondria, indicating that ACH5 is a mitochondrial enzyme.

Isolation of ACH5 Arabidopsis Mutant

The ACH5 T-DNA mutant which was used in the ACH4-antisense expression experiment as described above was found in the ALPHA population of the Arabidopsis Knock-out Facility using their protocols and methods. The primers used for the screen were the following:

GSP5-5: ACTAGGCACTACTTAGGCAGGAATGAAAG (SEQ ID NO: 45)

GSP5-6: TCTATCACAGAGGGAAAGAATGATCAAAC (SEQ ID NO: 46)

The rounds of screening were similar to those described for ACH1 and ACH2.

The T-DNA mutant identified was identical to wild-type Arabidopsis in every way examined. This included both the physical characteristics of the plant as well as the lipid profile of the lipids stored in the seeds. These results are not surprising, since there is a close acyl-CoA thioesterase homologue, ACH4, which probably serves a redundant role to ACH5. If these enzymes play an important role in the lipid metabolism of the plant, then a double-knockout in which both genes are impaired, as described above, will be informative.

All publications and patents mentioned in the above specification are herein incorporated by reference. Various modifications and variations of the described compositions and methods of the invention will be apparent to those skilled in the art without departing from the scope and spirit of the invention. Although the invention has been described in connection with particular preferred embodiments, it should be understood that the inventions claimed should not be unduly limited to such specific embodiments. Indeed, various modifications of the described modes for carrying out the invention which are obvious to those skilled in the art and in fields related thereto are intended to be within the scope of the following claims.

---

What is claimed is:

1. An isolated nucleic acid sequence encoding a protein comprising amino acid sequence SEQ ID NO:6.

2. The isolated nucleic acid sequence of claim 1, wherein the nucleic acid sequence is SEQ ID NO:2.

3. The nucleic acid sequence of claim 1, wherein said sequence is operably linked to a heterologous promoter.

4. The nucleic acid sequence of claim 1, wherein said sequence is contained within a vector.

5. The nucleic acid sequence of claim 1, wherein said nucleic acid sequence is within a host cell.

6. A method for assaying acyl-CoA thioesterase activity comprising:

a) providing the nucleic acid sequence of claim 1;

b) expressing said nucleic acid sequence under conditions such that a protein is produced; and c) assaying for acyl-CoA thioesterase activity.

7. The method of claim 6, wherein the nucleic acid sequence is SEQ ID NO:2.

8. The nucleic acid sequence of claim 5, wherein the host cell is a microorganism or a plant cell.

9. A transgenic plant comprising the nucleic acid sequence of claim 1, wherein said nucleic acid sequence is operably linked to a heterologous promoter.

* * * * *

SEQUENCE LISTING

<160> NUMBER OF SEQ ID NOS: 46

<210> SEQ ID NO 1
<211> LENGTH: 1278
<212> TYPE: DNA
<213> ORGANISM: Arabidopsis thaliana

<400> SEQUENCE: 1

```
atgaacactg aatcagttgt cgagttcctt gggaatgtga ccttgttgca gcggttacct      60
agttcctctc tgaagagaat ctccgaagtc gttgtcttca aaggttatga cagaggtgat     120
```

```
tatgtggttc gtgaaaatca aaatgtggat ggagtttatt ttctcttgca aggacaggct    180
caggttctga gatcagccgg agaggaaaac tatcaagagt tcccttttga acgatatgat    240
ttcttcggcc atggtatttt cggggatgtt tactcagcag atgttgttgc tgtgacagag    300
cttacctgct tgctgttgat gtctgatcat cgtgctttac ttgaaataaa gtcagtctcg    360
gattcagata aggaacgctg tcttgtggaa gacatactat atctagaacc attagatttg    420
aatgtatacc gggggttcac cccacctaat gctccaacct atggaaaggt ttatggaggg    480
caattagttg gacaggcact tgccgcagca tcaaaaactg ttgaaactat gaagatagtc    540
cataattttc attgctattt ccttcttgtt ggagatataa atattcccat catatatgat    600
gttaaccgct acgtgacgg caacaacttt gccaccagaa gtgtagatgc tagacagaaa    660
ggaaaaacta tattcacctt gttcgcgtca tttcagaaaa agcaacaagg ttttattcac    720
caggagtcga ccatgcctca tacaccagct cctgaaacgc ttctaccaag ggaggagatg    780
cttgaacggc ttgttactga gcctctgcta cctagggatt accgaaacca gttgcaact    840 gaaattagtg ttccattccc tatagatatt cgattttgtg agccaaatcg ttccactaaa    900
cagaataagt ctcctccaag actaaaatat tggtttagag caaagggaaa actttctgat    960
gatgatcaag ctttgcacag atgtgtggtt gcatttgctt ccgatttgat attcgccact   1020
atcagtttaa accctcaccg gagagagggc atgagtgtag ctgctcttag cctggaccac   1080
tcgatgtggt tccaccgacc tgtaagagca gatgattggt tgttgtttgt gatagtgagt   1140
ccaactgcga ccgaaagccg cggttttgca actggcaaaa tgttcaacag aaaggggagag  1200 ctggtggtat cattgacgca agaagctgtg ttaagagaag ctgtgactat taagccatcc   1260
ttcggggcca agctatga                                                 1278

<210> SEQ ID NO 2
<211> LENGTH: 1284
<212> TYPE: DNA
<213> ORGANISM: Arabidopsis thaliana

<400> SEQUENCE: 2
atgaacaccg agtcagttgt cgagttcctt ggaaacgtcc ctttactcca gaaattaccg     60
agctcttctc tgaagaaaat tgctcaagtt gttgtgccga acgttacgg gaaaggggat    120 tatgtggttc gtgaagatca aacttgggat ggatgttatt ttattttgca aggagaggct    180
caggtttccg gaccagacga agaagataac cgttccgaat tcctcttgaa acagtatgat    240
tacttcggcg ttggtttatc tgggaacgtt cattcagcag acattgttgc tatgtcccag    300
cttacgtgtt tggtgttgcc gcgtgatcac tgtcatttgc ttgagactaa ttccatctgg    360
caatcggata cgtcacttga caaatgctct ttagtggaac gcattttgca actcgaccct    420
ttagaattga atatcttcag ggggatcaca ctacctgatg ctcctatatt tggaaaggtt    480
tttggaggac aatttgtcgg acaggctctt gctgcggcgt caaaaactgt tgattttctc    540
aaggtcgtcc acagtttaca ctcctatttt cttctcgttg gagatattga catccccatt    600
atttatcaag ttcaccgcat acgtgatggg aacaactttg ccacccgaag agttgatgca    660
gtacagaaag gaaatatcat attcatcttg ctggcatcat ttcagaaaga caacaagga    720 tttgagcacc aggagtcaac catgccctct gtaccagatc ctgatacgct tctatcactg    780
gaggagttgc gtgaaagccg tataactgat cctcatttac cgaggagtta tcggaacaaa    840
gttgcaacta gaaactttgt tccatggcct atagagattc gattttgtga gcccagcaat    900
```

| | |
|---|---:|
| tcaacaaatc agacaaagtc tcctccgaga ttgaactatt ggtttagagc aaagggaagg | 960 |
| ctttctgatg atcaagcttt gcaccgatgt gtcgttgcat ttgcctcgga tttaatattt | 1020 |
| tgtggtgttg gtttgaaccc tcaccggaga aagggggtga atccgccgc acttagcctg | 1080 |
| gaccatgcga tgtggtttca ccgacctcta agagccgacg agtggttgct ctatgtgatt | 1140 |
| gtgagtccaa ctgcgcatga acccgtggt tttgtgactg gtcaaatgtt caacaggaaa | 1200 |
| ggagagctgg ttgtatcatt aacgcaagag gccctattaa gagaggctag acctccaaaa | 1260 |
| ccctccggca cgtcgaagct ctga | 1284 |

<210> SEQ ID NO 3
<211> LENGTH: 1317
<212> TYPE: DNA
<213> ORGANISM: Arabidopsis thaliana

<400> SEQUENCE: 3

| | |
|---|---:|
| atgaattccc caagacccat ctccgtcgtc tccaccttcg cttcaccatc ctccacctct | 60 |
| gacccaaccc gaaaacccct taagcttatgg ccaggtatgt accattcacc tgtcaccacc | 120 |
| gctctttggg aagccagatc caaaatcttc gaatctcttc tcgatcctcc taaagacgct | 180 |
| ccaccacaga gccagcttct caccagaact ccttctcata gccgtaccac catttttctac | 240 |
| cctttctcca ctgatttcat tctcagagag caatacagag atccttggaa cgaggtccgt | 300 |
| atcgggatct tgctcgaaga tctcgatgct ttagccggca ctatctccgt caagcattgt | 360 |
| tctgatgatg atagtacaac gaggccactc ttgcttgtta cagcttctgt tcataagatt | 420 |
| gtcttaaaga agccgatttg tgtcgacatt gatctcaaga ttgttgcttc tgtcatttgg | 480 |
| gttggtcgtt catctatcga gattcaactc gaagttatgc aatccgaatt gaaagatgtc | 540 |
| aaggcttctt cagattctgt tgctttaact gcaaatttca ttttttgtgg cgcgtgattct | 600 |
| aagactggta agctgctcc tatcaaccgt ctttctcctg aaaccgaggt tgagaaactt | 660 |
| ctctttgagg aagctgaagc taggaataac ttaaggaaga agaagagagg aggtgacaga | 720 |
| agggaatttg atcacgggga gtgtaagaag cttgaggctt ggttggctga aggaaggatt | 780 |
| ttctctgaca tgccagctct tgctgacaga aacagcattc ttcttaaaga cactcgtctt | 840 |
| gagaattcgc tgtatatgcca accgcagcag aggaacatcc atggtaggat ctttggaggg | 900 |
| tttttaatgc atagagcatt tgagttggct ttctctactg cttatacgtt tgcgggtcta | 960 |
| gtgccttact tcttagaagt tgatcacgtc gatttcctaa gaccggtgga cgtcggggat | 1020 |
| tcttacgtt tcaaatcctg tgttctttac actcaactgg ataaacagga ttgtccgctc | 1080 |
| atcaatatcg aagttgttgc tcatgttaca agtccagaga ttcgctccag tgaggtttca | 1140 |
| aatacattct acttcaagtt cactgtaagg ccagaggcaa aggccagaaa caatgggttt | 1200 |
| aaacttcgaa atgtagttcc tgccacagag gaagaagctc gtcatatcct cgagcgcatg | 1260 |
| gatgcagaag ctttgaagtc aagcaaacaa caatgtgtag gcacaattct tcagtaa | 1317 |

<210> SEQ ID NO 4
<211> LENGTH: 1368
<212> TYPE: DNA
<213> ORGANISM: Arabidopsis thaliana

<400> SEQUENCE: 4

| | |
|---|---:|
| atgagatctt cagcggggaaa gcttctctcc cattctctac ggagaaaccg cgggaaactt | 60 |
| ggtgatggat tttggattcc ggctacgagg tctcagaaga tgtggaattc gacggtaccg | 120 |
| tcagatgaaa atcctgatca aaattcgatc gatgcaggat cttcaatgcg gaaaccaatt | 180 |

```
agcttatggc ctggaatgta tcattctccg gtgactaatg cgctttggga agctcgtcgt      240
aatatgttcg aaattcctac cggagacgac gcttctcagt caaaattgac ggctaaatct      300
ccgtctcgaa gccgaacgtc aattctctat aagttttctt ctgattttgt tcttcgagaa      360
caatatagga atccttggaa tgagattcgt actggtaaat tggttgaaga tcttgacgct      420
cttgctggaa ccatctcctt caagcattgt ggtggtgaca gcagtgcgag atcgatgatt      480
ttggtgactg cttcagtgga taggattatc atgaaaagac ctattcgtgt agatactgac      540
cttagtatag ttggtgctgt tacatgggtt ggtagatcat ccatggagat gcaattacaa      600
gtactccaaa ttcaagatac caacaactcc tctgagtcgg ttgcccttga agcaaacttt      660
acattcgtgg ctcgggatgc tcagacaggc aagtcagctc caattaacca agtcgtgcca      720
gaaactgagc atgaaaaatt tctgtggaaa gaggcagaag agaggaacaa actacgaaaa      780
caaaagagag cacagggtaa agaagagcat gagaagttga aggacttaga gaggctaaat      840
gagttattag cagaaggacg agtattcctg gacatgccag ctcttgcaga tcggaacagc      900
atcctaatta aggatacttc ccatgaaaac tcattgatct gccagccaca gcaacgaaat      960
attcatggca gaattttttgg aggcttcttg atgcgcaaag cttttgagtt ggctttctcc     1020
aatgcttaca ccttcgctgg ggtttcacca cgtttctcg aagttgatcg cgtcgatttt      1080
atcaaaccag tggatgttgg aaatttcctt cgtttcaagt cacgcgtatt gtacacagaa     1140
gcaaccagtt cagctgaacc gctgataaac atcgaggttg tagctcatgt tacaagtcca     1200
gagctcagat ccagcgaagt ctccaacagg ttttacttca ccttcagtgt gagacctgag     1260
gccatgaaag atggattgaa aataagaaat gtggttccag caacagaaga agaagctaga     1320
agagtgatcg agcgcatgga cgcagagaga cccatctcat gccttga                   1368
```

<210> SEQ ID NO 5
<211> LENGTH: 425
<212> TYPE: PRT
<213> ORGANISM: Arabidopsis thaliana

<400> SEQUENCE: 5

```
Met Asn Thr Glu Ser Val Val Glu Phe Leu Gly Asn Val Thr Leu Leu
1               5                   10                  15

Gln Arg Leu Pro Ser Ser Leu Lys Arg Ile Ser Glu Val Val Val
            20                  25                  30

Phe Lys Gly Tyr Asp Arg Gly Asp Tyr Val Val Arg Glu Asn Gln Asn
        35                  40                  45

Val Asp Gly Val Tyr Phe Leu Leu Gln Gly Gln Ala Gln Val Leu Arg
    50                  55                  60

Ser Ala Gly Glu Glu Asn Tyr Gln Glu Phe Pro Leu Lys Arg Tyr Asp
65                  70                  75                  80

Phe Phe Gly His Gly Ile Phe Asp Val Tyr Ser Ala Asp Val Val
                85                  90                  95

Ala Val Thr Glu Leu Thr Cys Leu Leu Leu Met Ser Asp His Arg Ala
            100                 105                 110

Leu Leu Glu Ile Lys Ser Val Ser Asp Ser Asp Lys Glu Arg Cys Leu
        115                 120                 125

Val Glu Asp Ile Leu Tyr Leu Glu Pro Leu Asp Leu Asn Val Tyr Arg
    130                 135                 140

Gly Phe Thr Pro Pro Asn Ala Pro Thr Tyr Gly Lys Val Tyr Gly Gly
145                 150                 155                 160
```

```
Gln Leu Val Gly Gln Ala Leu Ala Ala Ser Lys Thr Val Glu Thr
                165                 170                 175

Met Lys Ile Val His Asn Phe His Cys Tyr Phe Leu Val Gly Asp
                180                 185                 190

Ile Asn Ile Pro Ile Ile Tyr Asp Val Asn Arg Leu Arg Asp Gly Asn
                195                 200                 205

Asn Phe Ala Thr Arg Ser Val Asp Ala Arg Gln Lys Gly Lys Thr Ile
210                 215                 220

Phe Thr Leu Phe Ala Ser Phe Gln Lys Gln Gln Gly Phe Ile His
225                 230                 235                 240

Gln Glu Ser Thr Met Pro His Thr Pro Ala Pro Glu Thr Leu Leu Pro
                245                 250                 255

Arg Glu Glu Met Leu Glu Arg Leu Val Thr Glu Pro Leu Leu Pro Arg
                260                 265                 270

Asp Tyr Arg Asn Gln Val Ala Thr Glu Ile Ser Val Pro Phe Pro Ile
                275                 280                 285

Asp Ile Arg Phe Cys Glu Pro Asn Arg Ser Thr Lys Gln Asn Lys Ser
                290                 295                 300

Pro Pro Arg Leu Lys Tyr Trp Phe Arg Ala Lys Gly Lys Leu Ser Asp
305                 310                 315                 320

Asp Asp Gln Ala Leu His Arg Cys Val Val Ala Phe Ala Ser Asp Leu
                325                 330                 335

Ile Phe Ala Thr Ile Ser Leu Asn Pro His Arg Arg Glu Gly Met Ser
                340                 345                 350

Val Ala Ala Leu Ser Leu Asp His Ser Met Trp Phe His Arg Pro Val
                355                 360                 365

Arg Ala Asp Asp Trp Leu Leu Phe Val Ile Val Ser Pro Thr Ala Thr
370                 375                 380

Glu Ser Arg Gly Phe Ala Thr Gly Lys Met Phe Asn Arg Lys Gly Glu
385                 390                 395                 400

Leu Val Val Ser Leu Thr Gln Glu Ala Val Leu Arg Glu Ala Val Thr
                405                 410                 415

Ile Lys Pro Ser Phe Gly Ala Lys Leu
                420                 425

<210> SEQ ID NO 6
<211> LENGTH: 427
<212> TYPE: PRT
<213> ORGANISM: Arabidopsis thaliana

<400> SEQUENCE: 6

Met Asn Thr Glu Ser Val Val Glu Phe Leu Gly Asn Val Pro Leu Leu
1               5                   10                  15

Gln Lys Leu Pro Ser Ser Leu Lys Lys Ile Ala Gln Val Val
                20                  25                  30

Pro Lys Arg Tyr Gly Lys Gly Asp Tyr Val Val Arg Glu Asp Gln Thr
                35                  40                  45

Trp Asp Gly Cys Tyr Phe Ile Leu Gln Gly Glu Ala Gln Val Ser Gly
                50                  55                  60

Pro Asp Glu Glu Asp Asn Arg Ser Glu Phe Leu Leu Lys Gln Tyr Asp
65                  70                  75                  80

Tyr Phe Gly Val Gly Leu Ser Gly Asn Val His Ser Ala Asp Ile Val
                85                  90                  95

Ala Met Ser Gln Leu Thr Cys Leu Val Leu Pro Arg Asp His Cys His
                100                 105                 110
```

```
Leu Leu Glu Thr Asn Ser Ile Trp Gln Ser Asp Thr Ser Leu Asp Lys
            115                 120                 125

Cys Ser Leu Val Glu Arg Ile Leu Gln Leu Asp Pro Leu Glu Leu Asn
    130                 135                 140

Ile Phe Arg Gly Ile Thr Leu Pro Asp Ala Pro Ile Phe Gly Lys Val
145                 150                 155                 160

Phe Gly Gln Phe Val Gly Gln Ala Leu Ala Ala Ser Lys Thr
                165                 170                 175

Val Asp Phe Leu Lys Val Val His Ser Leu His Ser Tyr Phe Leu Leu
            180                 185                 190

Val Gly Asp Ile Asp Ile Pro Ile Ile Tyr Gln Val His Arg Ile Arg
            195                 200                 205

Asp Gly Asn Asn Phe Ala Thr Arg Arg Val Asp Ala Val Gln Lys Gly
            210                 215                 220

Asn Ile Ile Phe Ile Leu Leu Ala Ser Phe Gln Lys Glu Gln Gln Gly
225                 230                 235                 240

Phe Glu His Gln Glu Ser Thr Met Pro Ser Val Pro Asp Pro Asp Thr
                245                 250                 255

Leu Leu Ser Leu Glu Glu Leu Arg Glu Ser Arg Ile Thr Asp Pro His
            260                 265                 270

Leu Pro Arg Ser Tyr Arg Asn Lys Val Ala Thr Arg Asn Phe Val Pro
            275                 280                 285

Trp Pro Ile Glu Ile Arg Phe Cys Glu Pro Ser Asn Ser Thr Asn Gln
            290                 295                 300

Thr Lys Ser Pro Pro Arg Leu Asn Tyr Trp Phe Arg Ala Lys Gly Arg
305                 310                 315                 320

Leu Ser Asp Asp Gln Ala Leu His Arg Cys Val Val Ala Phe Ala Ser
                325                 330                 335

Asp Leu Ile Phe Cys Gly Val Gly Leu Asn Pro His Arg Arg Lys Gly
            340                 345                 350

Val Lys Ser Ala Ala Leu Ser Leu Asp His Ala Met Trp Phe His Arg
            355                 360                 365

Pro Leu Arg Ala Asp Glu Trp Leu Leu Tyr Val Ile Val Ser Pro Thr
370                 375                 380

Ala His Glu Thr Arg Gly Phe Val Thr Gly Gln Met Phe Asn Arg Lys
385                 390                 395                 400

Gly Glu Leu Val Val Ser Leu Thr Gln Glu Ala Leu Leu Arg Glu Ala
                405                 410                 415

Arg Pro Pro Lys Pro Ser Gly Thr Ser Lys Leu
                420                 425
```

<210> SEQ ID NO 7
<211> LENGTH: 438
<212> TYPE: PRT
<213> ORGANISM: Arabidopsis thaliana

<400> SEQUENCE: 7

```
Met Asn Ser Pro Arg Pro Ile Ser Val Val Ser Thr Phe Ala Ser Pro
1               5                   10                  15

Ser Ser Thr Ser Asp Pro Thr Arg Lys Pro Leu Ser Leu Trp Pro Gly
                20                  25                  30

Met Tyr His Ser Pro Val Thr Thr Ala Leu Trp Glu Ala Arg Ser Lys
            35                  40                  45

Ile Phe Glu Ser Leu Leu Asp Pro Pro Lys Asp Ala Pro Pro Gln Ser
```

```
            50                  55                  60
Gln Leu Leu Thr Arg Thr Pro Ser His Ser Arg Thr Thr Ile Phe Tyr
 65                  70                  75                  80

Pro Phe Ser Thr Asp Phe Ile Leu Arg Glu Gln Tyr Arg Asp Pro Trp
                 85                  90                  95

Asn Glu Val Arg Ile Gly Ile Leu Glu Asp Leu Asp Ala Leu Ala
                100                 105                 110

Gly Thr Ile Ser Val Lys His Cys Ser Asp Asp Ser Thr Thr Arg
                115                 120                 125

Pro Leu Leu Val Thr Ala Ser Val His Lys Ile Val Leu Lys Lys
130                 135                 140

Pro Ile Cys Val Asp Ile Asp Leu Lys Ile Val Ala Ser Val Ile Trp
145                 150                 155                 160

Val Gly Arg Ser Ser Ile Glu Ile Gln Leu Glu Val Met Gln Ser Glu
                165                 170                 175

Leu Lys Asp Val Lys Ala Ser Ser Asp Ser Val Ala Leu Thr Ala Asn
                180                 185                 190

Phe Ile Phe Val Ala Arg Asp Ser Lys Thr Gly Lys Ala Ala Pro Ile
                195                 200                 205

Asn Arg Leu Ser Pro Glu Thr Glu Val Glu Lys Leu Leu Phe Glu Glu
                210                 215                 220

Ala Glu Ala Arg Asn Asn Leu Arg Lys Lys Lys Arg Gly Gly Asp Arg
225                 230                 235                 240

Arg Glu Phe Asp His Gly Glu Cys Lys Lys Leu Glu Ala Trp Leu Ala
                245                 250                 255

Glu Gly Arg Ile Phe Ser Asp Met Pro Ala Leu Ala Asp Arg Asn Ser
                260                 265                 270

Ile Leu Leu Lys Asp Thr Arg Leu Glu Asn Ser Leu Ile Cys Gln Pro
                275                 280                 285

Gln Gln Arg Asn Ile His Gly Arg Ile Phe Gly Gly Phe Leu Met His
                290                 295                 300

Arg Ala Phe Glu Leu Ala Phe Ser Thr Ala Tyr Thr Phe Ala Gly Leu
305                 310                 315                 320

Val Pro Tyr Phe Leu Glu Val Asp His Val Asp Phe Leu Arg Pro Val
                325                 330                 335

Asp Val Gly Asp Phe Leu Arg Phe Lys Ser Cys Val Leu Tyr Thr Gln
                340                 345                 350

Leu Asp Lys Gln Asp Cys Pro Leu Ile Asn Ile Glu Val Val Ala His
                355                 360                 365

Val Thr Ser Pro Glu Ile Arg Ser Ser Glu Val Ser Asn Thr Phe Tyr
                370                 375                 380

Phe Lys Phe Thr Val Arg Pro Glu Ala Lys Ala Arg Asn Asn Gly Phe
385                 390                 395                 400

Lys Leu Arg Asn Val Val Pro Ala Thr Glu Glu Ala Arg His Ile
                405                 410                 415

Leu Glu Arg Met Asp Ala Glu Ala Leu Lys Ser Ser Lys Gln Gln Cys
                420                 425                 430

Val Gly Thr Ile Leu Gln
                435

<210> SEQ ID NO 8
<211> LENGTH: 455
<212> TYPE: PRT
<213> ORGANISM: Arabidopsis thaliana
```

<400> SEQUENCE: 8

```
Met Arg Ser Ser Ala Gly Lys Leu Leu Ser His Ser Leu Arg Arg Asn
1               5                   10                  15

Arg Gly Lys Leu Gly Asp Gly Phe Trp Ile Pro Ala Thr Arg Ser Gln
            20                  25                  30

Lys Met Trp Asn Ser Thr Val Pro Ser Asp Glu Asn Pro Asp Gln Asn
                35                  40                  45

Ser Ile Asp Ala Gly Ser Ser Met Arg Lys Pro Ile Ser Leu Trp Pro
    50                  55                  60

Gly Met Tyr His Ser Pro Val Thr Asn Ala Leu Trp Glu Ala Arg Arg
65                  70                  75                  80

Asn Met Phe Glu Ile Pro Thr Gly Asp Ala Ser Gln Ser Lys Leu
                85                  90                  95

Thr Ala Lys Ser Pro Ser Arg Ser Arg Thr Ser Ile Leu Tyr Lys Phe
            100                 105                 110

Ser Ser Asp Phe Val Leu Arg Glu Gln Tyr Arg Asn Pro Trp Asn Glu
        115                 120                 125

Ile Arg Thr Gly Lys Leu Val Glu Asp Leu Asp Ala Leu Ala Gly Thr
    130                 135                 140

Ile Ser Phe Lys His Cys Gly Gly Asp Ser Ser Ala Arg Ser Met Ile
145                 150                 155                 160

Leu Val Thr Ala Ser Val Asp Arg Ile Ile Met Lys Arg Pro Ile Arg
                165                 170                 175

Val Asp Thr Asp Leu Ser Ile Val Gly Ala Val Thr Trp Val Gly Arg
            180                 185                 190

Ser Ser Met Glu Met Gln Leu Gln Val Leu Gln Ile Gln Asp Thr Asn
        195                 200                 205

Asn Ser Ser Glu Ser Val Ala Leu Glu Ala Asn Phe Thr Phe Val Ala
    210                 215                 220

Arg Asp Ala Gln Thr Gly Lys Ser Ala Pro Ile Asn Gln Val Val Pro
225                 230                 235                 240

Glu Thr Glu His Glu Lys Phe Leu Trp Lys Ala Glu Glu Arg Asn
                245                 250                 255

Lys Leu Arg Lys Gln Lys Arg Ala Gln Gly Lys Glu Glu His Glu Lys
            260                 265                 270

Leu Lys Asp Leu Glu Arg Leu Asn Glu Leu Leu Ala Glu Gly Arg Val
        275                 280                 285

Phe Leu Asp Met Pro Ala Leu Ala Asp Arg Asn Ser Ile Leu Ile Lys
    290                 295                 300

Asp Thr Ser His Glu Asn Ser Leu Ile Cys Gln Pro Gln Gln Arg Asn
305                 310                 315                 320

Ile His Gly Arg Ile Phe Gly Gly Phe Leu Met Arg Lys Ala Phe Glu
                325                 330                 335

Leu Ala Phe Ser Asn Ala Tyr Thr Phe Ala Gly Val Ser Pro Arg Phe
            340                 345                 350

Leu Glu Val Asp Arg Val Asp Phe Ile Lys Pro Val Asp Val Gly Asn
        355                 360                 365

Phe Leu Arg Phe Lys Ser Arg Val Leu Tyr Thr Glu Ala Thr Ser Ser
    370                 375                 380

Ala Glu Pro Leu Ile Asn Ile Glu Val Val Ala His Val Thr Ser Pro
385                 390                 395                 400

Glu Leu Arg Ser Ser Glu Val Ser Asn Arg Phe Tyr Phe Thr Phe Ser
```

```
                     405                 410                 415
Val Arg Pro Glu Ala Met Lys Asp Gly Leu Lys Ile Arg Asn Val Val
            420                 425                 430

Pro Ala Thr Glu Glu Ala Arg Arg Val Ile Glu Arg Met Asp Ala
            435                 440                 445

Glu Arg Pro Ile Ser Leu Pro
    450                 455

<210> SEQ ID NO 9
<211> LENGTH: 56
<212> TYPE: PRT
<213> ORGANISM: Arabidopsis thaliana

<400> SEQUENCE: 9

Thr Ile Asp His Ser Met Trp Phe His Arg Pro Phe Asn Leu Asn Glu
1               5                   10                  15

Trp Leu Leu Tyr Ser Val Glu Ser Thr Ser Ala Ser Ser Ala Arg Gly
                20                  25                  30

Phe Val Arg Gly Glu Phe Tyr Thr Gln Asp Gly Val Leu Val Ala Ser
            35                  40                  45

Thr Val Gln Glu Gly Val Met Arg
    50                  55

<210> SEQ ID NO 10
<211> LENGTH: 56
<212> TYPE: PRT
<213> ORGANISM: Arabidopsis thaliana

<400> SEQUENCE: 10

Ser Leu Asp His Ala Met Trp Phe Thr Asp Pro Leu Arg Ala Asp Glu
1               5                   10                  15

Trp Leu Leu Tyr Val Ile Val Ser Pro Thr Ala His Glu Thr Arg Gly
                20                  25                  30

Phe Val Thr Gly Gln Met Phe Asn Arg Lys Gly Glu Leu Val Val Ser
            35                  40                  45

Leu Thr Gln Glu Ala Leu Leu Arg
    50                  55

<210> SEQ ID NO 11
<211> LENGTH: 106
<212> TYPE: PRT
<213> ORGANISM: Arabidopsis thaliana

<400> SEQUENCE: 11

Met Asn Thr Glu Ser Val Val Glu Phe Leu Gly Asn Val Thr Leu Leu
1               5                   10                  15

Gln Arg Leu Pro Ser Ser Ser Leu Lys Arg Ile Ser Glu Val Val Val
                20                  25                  30

Phe Lys Gly Tyr Asp Arg Gly Tyr Val Val Arg Glu Asn Gln Asn
            35                  40                  45

Val Asp Gly Val Tyr Phe Leu Leu Gln Gly Gln Ala Gln Val Leu Arg
    50                  55                  60

Ser Ala Gly Glu Glu Asn Tyr Gln Glu Phe Pro Leu Lys Arg Tyr Asp
65                  70                  75                  80

Phe Phe Gly His Gly Ile Phe Gly Asp Val Tyr Ser Ala Asp Val Val
                85                  90                  95

Ala Val Thr Glu Leu Thr Cys Leu Leu Leu
            100                 105
```

<210> SEQ ID NO 12
<211> LENGTH: 106
<212> TYPE: PRT
<213> ORGANISM: Arabidopsis thaliana

<400> SEQUENCE: 12

```
Met Asn Thr Glu Ser Val Val Glu Phe Leu Gly Asn Val Pro Leu Leu
1               5                  10                  15

Gln Lys Leu Pro Ser Ser Ser Leu Lys Lys Ile Ala Gln Val Val Val
            20                  25                  30

Pro Lys Arg Tyr Gly Lys Gly Asp Tyr Val Val Arg Glu Asp Gln Thr
        35                  40                  45

Trp Asp Gly Cys Tyr Phe Ile Leu Gln Gly Glu Ala Gln Val Ser Gly
    50                  55                  60

Pro Asp Glu Glu Asp Asn Arg Ser Glu Phe Leu Leu Lys Gln Tyr Asp
65                  70                  75                  80

Tyr Phe Gly Val Gly Leu Ser Gly Asn Val His Ser Ala Asp Ile Val
                85                  90                  95

Ala Met Ser Gln Leu Thr Cys Leu Val Leu
            100                 105
```

<210> SEQ ID NO 13
<211> LENGTH: 20
<212> TYPE: DNA
<213> ORGANISM: Artificial Sequence
<220> FEATURE:
<223> OTHER INFORMATION: Synthetic

<400> SEQUENCE: 13
ggaagacata ctatatctag                                               20

<210> SEQ ID NO 14
<211> LENGTH: 20
<212> TYPE: DNA
<213> ORGANISM: Artificial Sequence
<220> FEATURE:
<223> OTHER INFORMATION: Synthetic

<400> SEQUENCE: 14
gtacctctcc ctttctgttg                                               20

<210> SEQ ID NO 15
<211> LENGTH: 23
<212> TYPE: DNA
<213> ORGANISM: Artificial Sequence
<220> FEATURE:
<223> OTHER INFORMATION: Synthetic

<400> SEQUENCE: 15
catgaacact gaatcagttg tcg                                           23

<210> SEQ ID NO 16
<211> LENGTH: 21
<212> TYPE: DNA
<213> ORGANISM: Artificial Sequence
<220> FEATURE:
<223> OTHER INFORMATION: Synthetic

<400> SEQUENCE: 16
aacactgaat cagttgtcga g                                             21

```
<210> SEQ ID NO 17
<211> LENGTH: 22
<212> TYPE: DNA
<213> ORGANISM: Artificial Sequence
<220> FEATURE:
<223> OTHER INFORMATION: Synthetic

<400> SEQUENCE: 17
tcgagggctt catagcttgg cc                                          22

<210> SEQ ID NO 18
<211> LENGTH: 20
<212> TYPE: DNA
<213> ORGANISM: Artificial Sequence
<220> FEATURE:
<223> OTHER INFORMATION: Synthetic

<400> SEQUENCE: 18
gggcttcata gcttggcccc                                             20

<210> SEQ ID NO 19
<211> LENGTH: 33
<212> TYPE: DNA
<213> ORGANISM: Artificial Sequence
<220> FEATURE:
<223> OTHER INFORMATION: Synthetic

<400> SEQUENCE: 19
atccggtaag tactcatatg aacactgaat cag                              33

<210> SEQ ID NO 20
<211> LENGTH: 33
<212> TYPE: DNA
<213> ORGANISM: Artificial Sequence
<220> FEATURE:
<223> OTHER INFORMATION: Synthetic

<400> SEQUENCE: 20
atcctatggc ttcactcgag cttggccccg aag                              33

<210> SEQ ID NO 21
<211> LENGTH: 28
<212> TYPE: DNA
<213> ORGANISM: Artificial Sequence
<220> FEATURE:
<223> OTHER INFORMATION: Synthetic

<400> SEQUENCE: 21
acccaagcag tacacacatt caagtaca                                    28

<210> SEQ ID NO 22
<211> LENGTH: 28
<212> TYPE: DNA
<213> ORGANISM: Artificial Sequence
<220> FEATURE:
<223> OTHER INFORMATION: Synthetic

<400> SEQUENCE: 22
cgtcgttaac ctgtaaaatg aaccactg                                    28

<210> SEQ ID NO 23
<211> LENGTH: 18
<212> TYPE: DNA
<213> ORGANISM: Artificial Sequence
<220> FEATURE:
<223> OTHER INFORMATION: Synthetic
```

```
<400> SEQUENCE: 23
accgaccctc taagagcc                                                18

<210> SEQ ID NO 24
<211> LENGTH: 18
<212> TYPE: DNA
<213> ORGANISM: Artificial Sequence
<220> FEATURE:
<223> OTHER INFORMATION: Synthetic

<400> SEQUENCE: 24 tgatctttt attcgtcg                                                 18

<210> SEQ ID NO 25
<211> LENGTH: 20
<212> TYPE: DNA
<213> ORGANISM: Artificial Sequence
<220> FEATURE:
<223> OTHER INFORMATION: Synthetic

<400> SEQUENCE: 25
cgccatgaac accgagtcag                                              20

<210> SEQ ID NO 26
<211> LENGTH: 21
<212> TYPE: DNA
<213> ORGANISM: Artificial Sequence
<220> FEATURE:
<223> OTHER INFORMATION: Synthetic

<400> SEQUENCE: 26
gagccattca gagcttcgac g                                            21

<210> SEQ ID NO 27
<211> LENGTH: 19
<212> TYPE: DNA
<213> ORGANISM: Artificial Sequence
<220> FEATURE:
<223> OTHER INFORMATION: Synthetic

<400> SEQUENCE: 27
atcagagctt cgacgtgcc                                               19

<210> SEQ ID NO 28
<211> LENGTH: 21
<212> TYPE: DNA
<213> ORGANISM: Artificial Sequence
<220> FEATURE:
<223> OTHER INFORMATION: Synthetic

<400> SEQUENCE: 28
ctagatcaga gcttcgacgt g                                            21

<210> SEQ ID NO 29
<211> LENGTH: 20
<212> TYPE: DNA
<213> ORGANISM: Artificial Sequence
<220> FEATURE:
<223> OTHER INFORMATION: Synthetic

<400> SEQUENCE: 29
catgaacacc gagtcagttg                                              20

<210> SEQ ID NO 30
<211> LENGTH: 21
```

```
<212> TYPE: DNA
<213> ORGANISM: Artificial Sequence
<220> FEATURE:
<223> OTHER INFORMATION: Synthetic

<400> SEQUENCE: 30
aattcatgaa caccgagtca g                                          21

<210> SEQ ID NO 31
<211> LENGTH: 30
<212> TYPE: DNA
<213> ORGANISM: Artificial Sequence
<220> FEATURE:
<223> OTHER INFORMATION: Synthetic

<400> SEQUENCE: 31
attaagtagg aggaaaatcc atcgtgacag                                 30

<210> SEQ ID NO 32
<211> LENGTH: 31
<212> TYPE: DNA
<213> ORGANISM: Artificial Sequence
<220> FEATURE:
<223> OTHER INFORMATION: Synthetic

<400> SEQUENCE: 32
cgagaagaaa tcacagaatt gctcagatta c                               31

<210> SEQ ID NO 33
<211> LENGTH: 22
<212> TYPE: DNA
<213> ORGANISM: Artificial Sequence
<220> FEATURE:
<223> OTHER INFORMATION: Synthetic

<400> SEQUENCE: 33
ccaggtatgt accattcacc tg                                         22

<210> SEQ ID NO 34
<211> LENGTH: 23
<212> TYPE: DNA
<213> ORGANISM: Artificial Sequence
<220> FEATURE:
<223> OTHER INFORMATION: Synthetic

<400> SEQUENCE: 34
gatatgacga gcttcttcct ctg                                        23

<210> SEQ ID NO 35
<211> LENGTH: 20
<212> TYPE: DNA
<213> ORGANISM: Artificial Sequence
<220> FEATURE:
<223> OTHER INFORMATION: Synthetic

<400> SEQUENCE: 35
aattatgaat tccccaagac                                            20

<210> SEQ ID NO 36
<211> LENGTH: 18
<212> TYPE: DNA
<213> ORGANISM: Artificial Sequence
<220> FEATURE:
<223> OTHER INFORMATION: Synthetic

<400> SEQUENCE: 36
```

|  |  |
|---|---|
| atgaattccc caagaccc | 18 |

<210> SEQ ID NO 37
<211> LENGTH: 19
<212> TYPE: DNA
<213> ORGANISM: Artificial Sequence
<220> FEATURE:
<223> OTHER INFORMATION: Synthetic

<400> SEQUENCE: 37

|  |  |
|---|---|
| gatcctgaag aattgtgcc | 19 |

<210> SEQ ID NO 38
<211> LENGTH: 18
<212> TYPE: DNA
<213> ORGANISM: Artificial Sequence
<220> FEATURE:
<223> OTHER INFORMATION: Synthetic

<400> SEQUENCE: 38

|  |  |
|---|---|
| ctgaagaatt gtgcctac | 18 |

<210> SEQ ID NO 39
<211> LENGTH: 21
<212> TYPE: DNA
<213> ORGANISM: Artificial Sequence
<220> FEATURE:
<223> OTHER INFORMATION: Synthetic

<400> SEQUENCE: 39

|  |  |
|---|---|
| aattatgaga tcttcagcgg g | 21 |

<210> SEQ ID NO 40
<211> LENGTH: 18
<212> TYPE: DNA
<213> ORGANISM: Artificial Sequence
<220> FEATURE:
<223> OTHER INFORMATION: Synthetic

<400> SEQUENCE: 40

|  |  |
|---|---|
| atgagatctt cagcggga | 18 |

<210> SEQ ID NO 41
<211> LENGTH: 19
<212> TYPE: DNA
<213> ORGANISM: Artificial Sequence
<220> FEATURE:
<223> OTHER INFORMATION: Synthetic

<400> SEQUENCE: 41

|  |  |
|---|---|
| gatcaggcaa tgagatggg | 19 |

<210> SEQ ID NO 42
<211> LENGTH: 19
<212> TYPE: DNA
<213> ORGANISM: Artificial Sequence
<220> FEATURE:
<223> OTHER INFORMATION: Synthetic

<400> SEQUENCE: 42

|  |  |
|---|---|
| aggcaatgag atgggtctc | 19 |

<210> SEQ ID NO 43
<211> LENGTH: 21
<212> TYPE: DNA
<213> ORGANISM: Artificial Sequence

```
<220> FEATURE:
<223> OTHER INFORMATION: Synthetic

<400> SEQUENCE: 43
atgagatctt cagcgggaaa g                                      21

<210> SEQ ID NO 44
<211> LENGTH: 20
<212> TYPE: DNA
<213> ORGANISM: Artificial Sequence
<220> FEATURE:
<223> OTHER INFORMATION: Synthetic

<400> SEQUENCE: 44
tcaaggcaat gagatgggtc                                        20

<210> SEQ ID NO 45
<211> LENGTH: 29
<212> TYPE: DNA
<213> ORGANISM: Artificial Sequence
<220> FEATURE:
<223> OTHER INFORMATION: Synthetic

<400> SEQUENCE: 45
actaggcact acttaggcag gaatgaaag                              29

<210> SEQ ID NO 46
<211> LENGTH: 29
<212> TYPE: DNA
<213> ORGANISM: Artificial Sequence
<220> FEATURE:
<223> OTHER INFORMATION: Synthetic

<400> SEQUENCE: 46
tctatcacag agggaaagaa tgatcaaac                              29
```